(12) United States Patent
Dowling et al.

(10) Patent No.: US 9,605,004 B2
(45) Date of Patent: Mar. 28, 2017

(54) CHEMICAL COMPOUNDS

(71) Applicants: SYNGENTA LIMITED, Guildford, Surrey (GB); SYNGENTA PARTICIPATIONS AG, Basel (CH)

(72) Inventors: Alan John Dowling, Bracknell (GB); Timothy Robert Desson, Bracknell (GB); William Guy Whittingham, Bracknell (GB); Anne Jacqueline Dalencon, Bracknell (GB); James Alan Morris, Bracknell (GB); Jutta Elisabeth Boehmer, Bracknell (GB); Mangala Phadte, Ilhas (IN); Adrian Longstaff, Bracknell (GB); Matthew Brian Hotson, Bracknell (GB); Paul John De Fraine, Bracknell (GB); Alison Jane Thompson, Bracknell (GB); Shuji Hachisu, Bracknell (GB)

(73) Assignees: Syngenta Limited, Guildford, Surrey (GB); Syngenta Participations AG, Basel (CH)

(*) Notice: Subject to any disclaimer, the term of this patent is extended or adjusted under 35 U.S.C. 154(b) by 0 days.

(21) Appl. No.: 14/906,621

(22) PCT Filed: Aug. 5, 2013

(86) PCT No.: PCT/EP2013/066394
§ 371 (c)(1),
(2) Date: Jan. 21, 2016

(87) PCT Pub. No.: WO2015/018433
PCT Pub. Date: Feb. 12, 2015

(65) Prior Publication Data
US 2016/0159819 A1  Jun. 9, 2016

(51) Int. Cl.
| | |
|---|---|
| *C07D 513/04* | (2006.01) |
| *C07D 403/04* | (2006.01) |
| *A01N 43/56* | (2006.01) |
| *C07D 471/04* | (2006.01) |
| *A01N 43/90* | (2006.01) |
| *C07D 487/04* | (2006.01) |
| *C07D 403/12* | (2006.01) |
| *G02B 7/02* | (2006.01) |

(52) U.S. Cl.
CPC ........... *C07D 513/04* (2013.01); *A01N 43/56* (2013.01); *A01N 43/90* (2013.01); *C07D 403/04* (2013.01); *C07D 403/12* (2013.01); *C07D 471/04* (2013.01); *C07D 487/04* (2013.01); *G02B 7/025* (2013.01); *G02B 7/026* (2013.01); *G02B 7/027* (2013.01)

(58) Field of Classification Search
CPC ........ A01N 43/56; A01N 43/90; C07D 403/04; C07D 403/12; C07D 471/04; C07D 487/04; C07D 513/04
USPC .......... 504/103, 130, 131, 139; 544/48; 548/359.1, 360.1, 364.1
See application file for complete search history.

(56) References Cited

FOREIGN PATENT DOCUMENTS

| | | | |
|---|---|---|---|
| CH | 633678 A5 | 12/1982 | |
| DE | EP 0334133 A1 * | 9/1989 | ............ A01N 43/56 |
| EP | 0334133 A1 | 9/1989 | |

OTHER PUBLICATIONS

International Search Report for International Application PCT/EP2013/066394 mailed Nov. 4, 2013.

\* cited by examiner

*Primary Examiner* — Janet Epps-Smith
*Assistant Examiner* — Courtney Brown
(74) *Attorney, Agent, or Firm* — James Cueva

(57) ABSTRACT

The invention relates to pyrrolone compounds of the formula (I), wherein X, $R^a$, $R^b$, $R^c$, $R^1$, $R^2$ and $R^3$ are as defined in the specification. Furthermore, the present invention relates to processes and intermediates for making compounds of formula (I), to herbicidal compositions comprising these compounds and to methods of using these compounds to control plant growth.

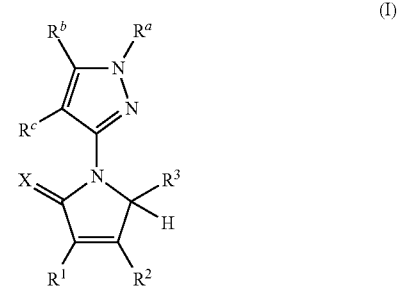

(I)

12 Claims, No Drawings

CHEMICAL COMPOUNDS

RELATED APPLICATION INFORMATION

This application is a 371 national stage entry of International Application No. PCT/EP2013/066394, filed Aug. 5, 2013.

The present invention relates to certain substituted pyrrolone derivatives, to processes for their preparation, herbicidal compositions comprising them, and their use in controlling plants or inhibiting plant growth.

Herbicidal pyrrolones of the formula

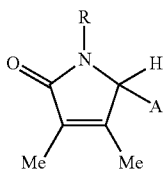

wherein A is hydroxy, halogen or OAcyl; and R is an optionally substituted aryl, aralkyl or heteroaryl group are taught in Swiss patent application CH633678.

Further herbicidal pyrrolones of the formula

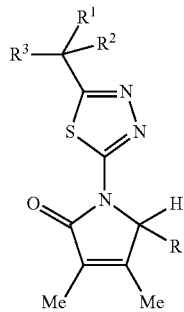

wherein R is inter alia OH, $R^1$ is H or alkyl, and $R^2$ and $R^3$ are alkyl, haloalkyl, or alkylene are taught in EP0286816A1.

Further herbicidal pyrrolones of the formula

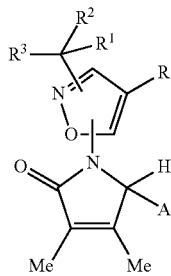

wherein A is e.g. OH, R is H, halogen, alkyl, haloalkyl, or alkoxyl, $R^1$ to $R^3$ are each H, halogen, alkyl, haloalkyl, alkyoxyalkyl, or $R^2$ and $R^3$ together form a 3 to 7 membered ring; are disclosed in EP0297378A2.

Further herbicidal pyrrolones of the formula

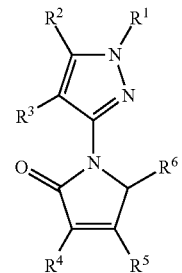

wherein $R^1$ is H, alkyl, haloalkyl, alkenyl, haloalkenyl, alkynyl, alkoxyalkyl or optionally substituted aryl or aralkyl, $R^2$ is H, alkyl, haloalkyl, alkenyl, haloalkenyl, alkynyl, alkoxyalkyl, alkylthioalkyl or optionally substituted cycloalkyl or aryl, $R^3$, $R^4$ and $R^5$ are, inter alia, H or alkyl and $R^6$ is, inter alia, OH are disclosed in EP0334133.

A problem that remains is the provision of alternative herbicidal pyrrolones.

A further problem that remains is the provision of herbicidal compounds having improved potency relative to known compounds.

A further problem that remains is the provision of herbicidal compounds having an improved spectrum of activity relative to known compounds.

A further problem that remains is the provision of herbicidal compounds having enhanced selectivity relative to known compounds.

These and other problems of the art are addressed by the present invention.

SUMMARY OF THE INVENTION

In a first aspect, the invention provides compounds of the formula (I)

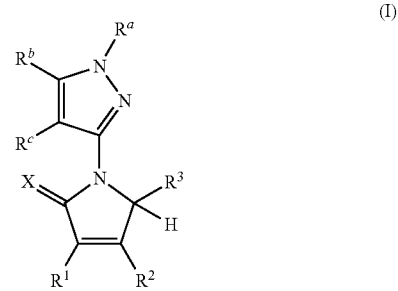

wherein
X is selected from S and O;
$R^a$ is selected from hydrogen, $C_1$-$C_6$ alkyl and $C_1$-$C_6$ haloalkyl;
$R^b$ is selected from hydrogen, formyl, hydroxyl, halogen, nitro, cyano, $C_1$-$C_6$ alkyl, $C_1$-$C_6$ cyanoalkyl, $C_3$-$C_6$ cycloalkyl, $C_3$-$C_6$ cyanocycloalkyl, $C_1$-$C_6$ haloalkyl, $C_1$-$C_6$ alkylthio, $C_1$-$C_6$ alkoxy, $C_1$-$C_6$ alkoxy $C_1$-$C_6$ alkyl, $C_1$-$C_6$ alkthio $C_1$-$C_6$ alkyl, $C_1$-$C_6$ cyanoalkoxy, $C_1$-$C_6$ haloalkoxy, $C_1$-$C_6$ alkoxy $C_1$-$C_6$ alkoxy, $C_2$-$C_6$ alkenyl, $C_2$-$C_6$ alkynyl, $C_2$-$C_6$ cyanoalkenyl, $C_2$-$C_6$ cyanoalkynyl, $C_2$-$C_6$ alkenyloxy, $C_2$-$C_6$ alkynyloxy, $C_2$-$C_6$ haloalkenyl, $C_2$-$C_6$ haloalkynyl, $C_2$-$C_6$ haloalkenyloxy, $C_2$-$C_6$ haloalkynyloxy, $C_1$-$C_6$ alkoxy $C_2$-$C_6$ alkenyl, $C_1$-$C_6$ alkoxy $C_2$-$C_6$ alkynyl, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylsulfonyloxy, $C_1$-$C_6$ alkylcarbonyl, $C_1$-$C_6$ haloalkylcarbonyl, $C_2$-$C_6$ alkenylcarbonyl, $C_2$-$C_6$ alkynylcarbonyl, $C_2$-$C_6$ haloalkenylcarbonyl, $C_2$-$C_6$ haloalkynylcarbonyl, tri $C_1$-$C_6$ alkylsilyl $C_2$-$C_6$ alkynyl, a group $R^5R^6N-$, a group $R^5C(O)N(R^6)-$, a group $R^5S(O_2)N(R^6)-$, a group $R^5R^6NSO_2-$, a $C_6$-$C_{10}$ aryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ aryloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ benzyl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ benzyloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_3$-$C_6$ heterocyclyl group optionally substituted by from 1 to 3 groups independently selected from $C_1$-$C_4$ alkyl, a $C_3$-$C_6$ cycloalkyl group optionally substituted with from 1 to 3 groups independently selected from halogen or $C_1$-$C_6$ alkyl and a $C_3$-$C_6$ cycloalkenyl group optionally substituted with from 1 to 3 groups independently selected from halogen or $C_1$-$C_6$ alkyl;

$R^c$ is selected from hydrogen, halogen, cyano, $C_1$-$C_6$ alkyl or $C_1$-$C_6$ haloalkyl;

or $R^a$ and $R^b$ together with the nitrogen and carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl;

or $R^b$ and $R^c$ together with the carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl;

$R^1$ is halogen or $C_1$-$C_3$ alkoxy;
$R^2$ is $C_1$-$C_6$ alkyl or $C_1$-$C_3$ alkoxy;
$R^3$ is selected from halogen, hydroxyl, or any one of the following groups

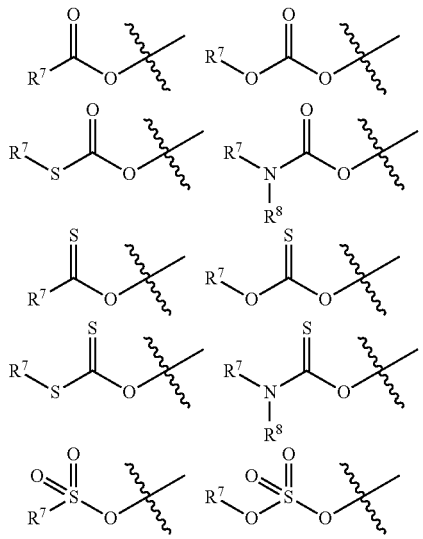

-continued

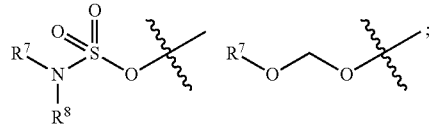

$R^5$ and $R^6$ are independently selected from hydrogen, $C_1$-$C_6$ alkyl, $C_1$-$C_6$ haloalkyl, $C_2$-$C_6$ alkenyl, $C_2$-$C_6$ alkynyl, or $R^5$ and $R^6$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen or $C_1$-$C_6$ alkyl;

$R^7$ and $R^8$ are independently selected from hydrogen, $C_1$-$C_6$ alkyl, $C_1$-$C_6$ haloalkyl, $C_2$-$C_6$ alkenyl, $C_2$-$C_6$ alkynyl, a $C_5$-$C_{10}$ heteroaryl group which can be mono- or bicyclic comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy, a $C_6$-$C_{10}$ aryl group optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, or $R^7$ and $R^8$ together with the atoms to which they are attached form a 3-6 membered saturated or partially unsaturated ring optionally comprising from 1 to 3 heteroatoms independently selected from S, O and N and optionally substituted with from 1 to 3 groups independently selected from halogen or $C_1$-$C_6$ alkyl;

$R^9$ is selected from $C_1$-$C_6$ alkyl or benzyl optionally substituted with 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy;

or an N-oxide or salt form thereof.

In a second aspect, the invention provides herbicidal compositions comprising a compound of the invention together with at least one agriculturally acceptable adjuvant or diluent.

In a third aspect, the invention provides the use of a compound or a composition of the invention for use as a herbicide.

In a fourth aspect, the invention provides a method of controlling weeds in crops of useful plants, comprising applying to said weeds or to the locus of said weeds, or to said useful crop plants, a compound or a composition of the invention.

In a fifth aspect, the invention relates to processes useful in the preparation of compounds of the invention.

In a sixth aspect, the invention relates to intermediates useful in the preparation of compounds of the invention.

DETAILED DESCRIPTION

Preferably, X is O.
Preferably, $R^a$ is selected from hydrogen, methyl, ethyl, iso-propyl or $C_1$-$C_3$ haloalkyl or $R^a$ and $R^b$ together with the nitrogen and carbon atoms to which they are attached form a 3-7 membered ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl. More preferably, $R^a$ is selected from hydrogen, methyl, ethyl or $R^a$ and $R^b$ together with the nitrogen and carbon atoms to which they are attached form a 3-7 membered ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl. Most preferably, $R^a$ is selected from hydrogen or methyl or $R^a$ and $R^b$ together with the nitrogen and carbon atoms to which they are attached form a 5 or 6 membered saturated ring optionally substituted with 1 to 3 groups independently selected from $C_1$-$C_3$ alkyl.

Preferably, $R^b$ is as defined above with the proviso that when $R^b$ is $C_2$-$C_6$ alkynyl, $C_2$-$C_6$ cyanoalkynyl, $C_2$-$C_6$ haloalkynyl or $C_1$-$C_6$ alkoxy $C_2$-$C_6$ alkynyl, the alkynyl group is not directly attached to the pyrazole ring.

More preferably, $R^b$ is selected from hydrogen, halogen, cyano, $C_1$-$C_6$ alkyl, $C_3$-$C_6$ cycloalkyl, $C_1$-$C_6$ haloalkyl, $C_2$-$C_6$ alkenyl, $C_1$-$C_6$ cyanoalkyl, $C_1$-$C_6$ alkylthio, $C_1$-$C_6$ alkylsulfinyl, $C_1$-$C_6$ alkylsulfonyl, $C_1$-$C_6$ alkoxy $C_1$-$C_6$ alkyl, $C_2$-$C_6$ alkynyl, $C_1$-$C_6$ alkoxy $C_2$-$C_6$ alkenyl, a $C_6$-$C_{10}$ benzyl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ aryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_3$-$C_6$ heteroaryl group optionally substituted by from 1 to 3 groups independently selected from $C_1$-$C_4$ alkyl, a $C_3$-$C_6$ cycloalkenyl group optionally substituted with from 1 to 3 groups independently selected from halogen or $C_1$-$C_6$ alkyl, or $R^a$ and $R^b$ together with the nitrogen and carbon atoms to which they are attached form a 3-7 membered ring optionally comprising 1 to 3 heteroatoms independently selected from S, O and N and optionally substituted with 1 to 3 groups independently selected from $C_1$-$C_6$ alkyl or $R^b$ and $R^c$ together with the carbon atoms to which they are attached form a 3-7 membered ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl.

More preferably, $R^b$ is selected from hydrogen, halogen, $C_1$-$C_6$ alkyl, $C_3$-$C_6$ cycloalkyl, $C_1$-$C_6$ haloalkyl, $C_2$-$C_6$ alkenyl, a $C_6$-$C_{10}$ aryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_3$-$C_6$ heteroaryl group optionally substituted by from 1 to 3 groups independently selected from $C_1$-$C_4$ alkyl, a $C_3$-$C_6$ cycloalkenyl group optionally substituted with from 1 to 3 groups independently selected from halogen or $C_1$-$C_6$ alkyl, or $R^a$ and $R^b$ together with the nitrogen and carbon atoms to which they are attached form a 3-7 membered ring optionally comprising 1 to 3 heteroatoms independently selected from S, O and N and optionally substituted with 1 to 3 groups independently selected from $C_1$-$C_6$ alkyl or $R^b$ and $R^c$ together with the carbon atoms to which they are attached form a 3-7 membered ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl.

Even more preferably, $R^b$ is selected from hydrogen, halogen, $C_1$-$C_4$ alkyl, $C_1$-$C_4$ haloalkyl, $C_2$-$C_4$ alkenyl or $C_1$-$C_4$ alkoxy or $R^a$ and $R^b$ together with the nitrogen and carbon atoms to which they are attached form a 3-7 membered ring optionally comprising 1 to 3 heteroatoms independently selected from S, O and N and optionally substituted with 1 to 3 groups independently selected from $C_1$-$C_6$ alkyl or $R^b$ and $R^c$ together with the carbon atoms to which they are attached form a 3-7 membered ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl.

Even more preferably, $R^b$ is selected from halogen, $C_1$-$C_4$ alkyl or $C_1$-$C_4$ haloalkyl or $R^a$ and $R^b$ together with the nitrogen and carbon atoms to which they are attached form a 5 or 6 membered saturated ring optionally substituted with 1 to 3 groups independently selected from $C_1$-$C_3$ alkyl, or $R^b$ and $R^c$ together with the carbon atoms to which they are attached form a 5 or 6 membered saturated ring optionally substituted with from 1 to 3 groups independently selected from halogen, $C_1$-$C_3$ alkyl and $C_1$-$C_3$ haloalkyl.

Even more preferably $R^b$ is selected from bromo, chloro, fluoro, iso-propyl, tert-butyl or trifluoromethyl or $R^a$ and $R^b$ together with the nitrogen and carbon atoms to which they are attached form a 5 or 6 membered saturated ring optionally substituted with 1 to 3 groups independently selected from $C_1$-$C_3$ alkyl, or $R^b$ and $R^c$ together with the carbon atoms to which they are attached form a 5 or 6 membered saturated ring optionally substituted with from 1 to 3 groups independently selected from halogen, $C_1$-$C_3$ alkyl and $C_1$-$C_3$ haloalkyl.

Most preferably, $R^b$ is selected from iso-propyl, tert-butyl or trifluoromethyl or $R^a$ and $R^b$ together with the nitrogen and carbon atoms to which they are attached form a 5 or 6 membered saturated ring optionally substituted with 1 to 3 groups independently selected from $C_1$-$C_3$ alkyl, or $R^b$ and $R^c$ together with the carbon atoms to which they are attached form a 5 or 6 membered saturated ring optionally substituted with from 1 to 3 groups independently selected from halogen, $C_1$-$C_3$ alkyl and $C_1$-$C_3$ haloalkyl.

Preferably, $R^c$ is selected from hydrogen, methyl, chloro, bromo or cyano or $R^b$ and $R^c$ together with the carbon atoms to which they are attached form a 3-7 membered ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl. More preferably, $R^c$ is selected from hydrogen, methyl or cyano or $R^b$ and $R^c$ together with the carbon atoms to which they are attached form a 3-7 membered ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl. Most preferably, $R^c$ is hydrogen or $R^b$ and $R^c$ together with the carbon atoms to which they are attached form a 5 or 6 membered saturated ring optionally substituted with from 1 to 3 groups independently selected from halogen, $C_1$-$C_3$ alkyl and $C_1$-$C_3$ haloalkyl.

In a preferred embodiment, the pyrazole ring is 5-tert-butyl-1-methyl-pyrazol-3-yl.

In a preferred embodiment, the pyrazole ring is 5-isopropyl-1-methyl-pyrazol-3-yl.

In a preferred embodiment, the pyrazole ring is 1-methyl-5-(trifluoromethyl)pyrazol-3-yl.

In a preferred embodiment, the pyrazole ring is 5-tert-butyl-1H-pyrazol-3-yl.

In a preferred embodiment, the pyrazole ring is 5-isopropyl-1H-pyrazol-3-yl.

In a preferred embodiment, the pyrazole ring is 5-(trifluoromethyl)-1H-pyrazol-3-yl.

In a preferred embodiment, the pyrazole ring is 5-(1,1-dimethylbut-3-enyl)-1-methyl-pyrazol-3-yl.

In a preferred embodiment, the pyrazole ring is 4,4-dimethyl-5,6-dihydropyrrolo[1,2-b]pyrazol-2-yl.

In a preferred embodiment, the pyrazole ring is 4,4-dimethyl-6,7-dihydro-5H-pyrazolo[1,5-a]pyridin-2-yl.

In a preferred embodiment, the pyrazole ring is 4,4-dimethyl-6,7-dihydropyrazolo[5,1-c][1,4]thiazin-2-yl.

In a preferred embodiment, the pyrazole ring is 5-(1-methoxy-1-methyl-propyl)-1-methyl-pyrazol-3-yl.

In a preferred embodiment, the pyrazole ring is 5-tert-butyl-4-chloro-1-methyl-pyrazol-3-yl.

In a preferred embodiment, the pyrazole ring is 5-tert-butyl-4-cyano-1-methyl-pyrazol-3-yl.

In a preferred embodiment, the pyrazole ring is 5-(1,1-dimethylbut-3-enyl)-1-methyl-pyrazol-3-yl.

In a preferred embodiment, the pyrazole ring is 4-ethyl-5,6-dihydro-4H-pyrrolo[1,2-b]pyrazol-2-yl.

In a preferred embodiment, the pyrazole ring is 5-chloro-1-methyl-pyrazol-3-yl.

In a preferred embodiment, the pyrazole ring is 5-iodo-1-methyl-pyrazol-3-yl.

In a preferred embodiment, the pyrazole ring is 4-methyl-5,6-dihydro-4H-pyrrolo[1,2-b]pyrazol-2-yl.

In a preferred embodiment, the pyrazole ring is 4,4-dimethyl-6,7-dihydro-5H-pyrazolo[1,5-a]pyridin-2-yl.

In a preferred embodiment, the pyrazole ring is 1-ethyl-5-(trifluoromethyl)pyrazol-3-yl.

In a preferred embodiment, the pyrazole ring is 1-methyl-5-(1,1,2,2,2-pentafluoroethyl)pyrazol-3-yl.

In a preferred embodiment, the pyrazole ring is 5-cyclopropyl-1H-pyrazol-3-yl.

In a preferred embodiment, the pyrazole ring is 5-(1,1,2,2,2-pentafluoroethyl)-1H-pyrazol-3-yl.

In a preferred embodiment, the pyrazole ring is 4,4-dimethyl-5,6-dihydropyrrolo[1,2-b]pyrazol-2-yl.

In a preferred embodiment, the pyrazole ring is 1-ethyl-6,6-dimethyl-4,5-dihydrocyclopenta[c]pyrazol-3-yl.

In a preferred embodiment, the pyrazole ring is 4-ethyl-4,5,6,7-tetrahydropyrazolo[1,5-a]pyridin-2-yl.

In a preferred embodiment, the pyrazole ring is 5-isopropenyl-1-methyl-pyrazol-3-yl.

In a preferred embodiment, the pyrazole ring is 4,4-dimethyl-5,5-dioxo-6,7-dihydropyrazolo[5,1-c][1,4]thiazin-2-yl.

In a preferred embodiment, the pyrazole ring is 5-(1-cyano-1-methyl-ethyl)-1-methyl-pyrazol-3-yl.

In a preferred embodiment, the pyrazole ring is 1-methyl-5-(2,2,2-trifluoro-1-methyl-ethyl)pyrazol-3-yl.

In a preferred embodiment, the pyrazole ring is 1-methyl-5-methylsulfonyl-pyrazol-3-yl.

In a preferred embodiment, the pyrazole ring is 1,6,6-trimethyl-4,5-dihydrocyclopenta[c]pyrazol-3-yl.

In a preferred embodiment, the pyrazole ring is 1-methyl-5-sec-butyl-pyrazol-3-yl.

In a preferred embodiment, the pyrazole ring is 5-(1-ethoxy-1-methyl-propyl)-1-methyl-pyrazol-3-yl.

Preferably, $R^1$ is bromo, chloro, methoxy or ethoxy.

Preferably, $R^2$ is methyl, ethyl, methoxy or ethoxy.

Preferably, (i) $R^1$ is bromo and $R^2$ is methyl, (ii) $R^1$ is bromo and $R^2$ is methoxy, (iii) $R^1$ is chloro and $R^2$ is methyl, (iv) $R^1$ is methoxy and $R^2$ is methyl. Most preferably, (i) $R^1$ is chloro and $R^2$ is methyl or (ii) $R^1$ is methoxy and $R^2$ is methyl.

Preferably, $R^3$ is selected from halogen, hydroxyl, $C_1$-$C_6$ alkoxycarbonyloxy or aryloxycarbonyloxy wherein the aryl group may be substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy. More preferably, $R^3$ is selected from hydroxyl or halogen. Most preferably, $R^3$ is hydroxyl.

The compounds of formula (I) may exist as different geometric isomers, or in different tautomeric forms. This invention covers all such isomers and tautomers, and mixtures thereof in all proportions, as well as isotopic forms such as deuterated compounds. For example, compounds of formula (II) may exist in equilibrium with the tautomeric form (III).

(II) (III)

The compounds of this invention may contain an asymmetric carbon atom and some of the compounds of this invention may contain one or more asymmetric centers and may thus give rise to optical isomers and diastereomers. While shown without respect to stereochemistry, the present invention includes such optical isomers and diastereomers; as well as the racemic and resolved, enantiomerically pure R and S stereoisomers; as well as other mixtures of the R and S stereoisomers and agrochemically acceptable salts thereof. It is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

Alkyl, as used herein refers to an aliphatic hydrocarbon chain and includes straight and branched chains e. g. of 1 to 6 carbon atoms such as methyl, ethyl, n-propyl, isopropyl, n-butyl, isobutyl, sec-butyl, t-butyl, n-pentyl, isopentyl, neopentyl, n-hexyl, and isohexyl.

Alkenyl, as used herein, refers to an aliphatic hydrocarbon chain having at least one double bond, and preferably one double bond, and includes straight and branched chains e. g. of 2 to 6 carbon atoms such as ethenyl(vinyl), prop-1-enyl, prop-2-enyl(allyl), isopropenyl, but-1-enyl, but-2-enyl, but-3-enyl, 2-methypropenyl.

Alkynyl, as used herein, refers to an aliphatic hydrocarbon chain having at least one triple bond, and preferably one triple bond, and includes straight and branched chains e. g. of 2 to 6 carbon atoms such as ethynyl, prop-1-ynyl, prop-2-ynyl (propargyl) but-1-ynyl, but-2-ynyl and but-3-ynyl.

Cycloalkyl, as used herein, refers to a cyclic, saturated hydrocarbon group having from 3 to 6 ring carbon atoms. Examples of cycloalkyl groups are cyclopropyl, cyclobutyl, cyclopentyl and cyclohexyl.

Cycloalkenyl, as used herein, refers to a cyclic, partially unsaturated hydrocarbon group having from 3 to 6 ring carbon atoms.

Alkoxy as used herein refers to the group —OR, wherein R is alkyl as defined above. Examples of alkoxy groups include methoxy, ethoxy, n-propoxy, isopropoxy, n-butoxy, isobutoxy, sec-butoxy, t-butoxy, n-pentoxy, isopentoxy, neopentoxy, n-hexyloxy, and isohexyloxy.

Alkenyloxy refers to the group —OR, wherein R is alkenyl as defined above. Examples of alkenyloxy groups are ethenyloxy, propenyloxy, isopropenyloxy, but-1-enyloxy, but-2-enyloxy, but-3-enyloxy, 2-methypropenyloxy etc.

Alkynyloxy refers to the group —OR, wherein R is alkynyl is as defined above. Examples of alkynyloxy groups are ethynyloxy, propynyloxy, but-1-ynyloxy, but-2-ynyloxy and but-3-ynyloxy.

Alkoxyalkyl as used herein refers to the group —ROR, wherein each R is, independently, an alkyl group as defined above.

Alkoxyalkenyl as used herein refers to the group —ROR', wherein R is an alkyl group as defined above and R' is an alkenyl group as defined above.

Alkoxyalkynyl as used herein refers to the group —ROR', wherein R is an alkyl group as defined above and R' is an alkynyl group as defined above.

Alkoxyalkoxy, as used herein, refers to the group —OROR, wherein each R is, independently, an alkyl group as defined above.

Cyanoalkyl as used herein refers to an alkyl group substituted with one or more cyano groups.

Cyanoalkenyl as used herein refers to an alkenyl group substituted with one or more cyano groups.

Cyanoalkynyl as used herein refers to an alkynyl group substituted with one or more cyano groups.

Cyanocycloalkyl as used herein refers to an cycloalkyl group substituted with one or more cyano groups.

Cyanoalkoxy as used herein refers to the group —OR, wherein R is cyanoalkyl as defined above.

Halogen, halide and halo refer to iodine, bromine, chlorine and fluorine.

Haloalkyl as used herein refers to an alkyl group as defined above wherein at least one hydrogen atom has been replaced with a halogen atom as defined above. Examples of haloalkyl groups include chloromethyl, dichloromethyl, trichloromethyl, fluoromethyl, difluoromethyl and trifluoromethyl. Preferred haloalkyl groups are fluoroalkyl groups {i.e. haloalkyl groups, containing fluorine as the only halogen). More highly preferred haloalkyl groups are perfluoroalkyl groups, i.e. alkyl groups wherein all the hydrogen atoms are replaced with fluorine atoms.

Haloalkenyl as used herein refers to an alkenyl group as defined above wherein at least one hydrogen atom has been replaced with a halogen atom as defined above.

Haloalkynyl as used herein refers to an alkynyl group as defined above wherein at least one hydrogen atom has been replaced with a halogen atom as defined above.

Haloalkoxy as used herein refers to the group —OR, wherein R is haloalkyl as defined above.

Haloalkenyloxy as used herein refers to the group —OR, wherein R is haloalkenyl as defined above.

Haloalkynyloxy as used herein refers to the group —OR, wherein R is haloalkynyl as defined above.

Alkylthio as used herein refers to the group —SR, wherein R is an alkyl group as defined above. Alkylthio groups include, but are not limited to, methylthio, ethylthio, propylthio, tert-butylthio, and the like.

Alkylthioalkyl as used herein refers to the group —RSR, wherein each R is, independently, an alkyl group as defined above.

Haloalkylthio as used herein refers to the group —SR, wherein R is a haloalkyl group as defined above.

Alkylsulfinyl as used herein refers to the group —S(O)R, wherein R is an alkyl group as defined above.

Alkylsulfonyl as used herein refers to the group —S(O)$_2$R, wherein R is an alkyl group as defined above.

Haloalkylsulfinyl as used herein refers to the group —S(O)R, wherein R is a haloalkyl group as defined above.

Haloalkylsulfonyl as used herein refers to the group —S(O)$_2$R, wherein R is a haloalkyl group as defined above.

Alkylsulfonyloxy, as used herein refers to the group —OSO$_2$R, wherein R is an alkyl group as defined above.

Alkylcarbonyl, as used herein refers to the group —COR, wherein R is an alkyl group as defined above. Examples of alkylcarbonyl groups include ethanoyl, propanoyl, n-butanoyl, etc.

Alkenylcarbonyl, as used herein, refers to the group —COR, wherein R is an alkenyl group as defined above.

Alkynylcarbonyl, as used herein refers to the group —COR, wherein R is an alkynyl group as defined above.

Haloalkylcarbonyl, as used herein refers to the group —COR, wherein R is a haloalkyl group as defined above.

Haloalkenylcarbonyl, as used herein refers to the group —COR, wherein R is a haloalkenyl group as defined above.

Haloalkynylcarbonyl, as used herein refers to the group —COR, wherein R is a haloalkynyl group as defined above.

Alkoxycarbonyloxy as used herein, refers to the group —OC(O)OR, wherein R is an alkyl group as defined above. Examples of alkoxycarbonyloxy groups are methoxycarbonyloxy, ethoxycarbonyloxy, propoxycarbonyloxy, but-1-oxycarbonyloxy, but-2-oxycarbonyloxy and but-3-oxycarbonyloxy.

Trialkylsilylalkynyl, as used herein, refers to the group —RSi(R')$_3$, wherein R is an alkynyl group as defined above and each R' is, independently, selected from an alkyl group as defined above.

Formyl, as used herein, refers to the group —C(O)H.

Hydroxy or hydroxyl, as used herein, refers to the group —OH.

Nitro, as used herein, refers to the group —NO$_2$.

Cyano as used herein, refers to the group —CN.

Aryl, as used herein, refers to an unsaturated aromatic carbocyclic group of from 6 to 10 carbon atoms having a single ring (e. g., phenyl) or multiple condensed (fused) rings, at least one of which is aromatic (e.g., indanyl, naphthyl). Preferred aryl groups include phenyl, naphthyl and the like. Most preferably, an aryl group is a phenyl group.

Aryloxy, as used herein, refers to the group —O-aryl, wherein aryl is as defined above. Preferred aryloxy groups include phenoxy, naphthyloxy and the like.

Aryloxycarbonyloxy, as used herein, refers to the group —OC(O)O-aryl wherein aryl is a as defined above.

Benzyl, as used herein, refers to the group —CH$_2$C$_6$H$_5$. Benzyl groups may be substituted on the alkyl linker or on the ring.

Benzyloxy, as used herein, refers to the group —OCH$_2$C$_6$H$_5$. Benzyloxy groups may be substituted on the linker or on the ring.

Heterocyclyl, as used herein, refers to a non-aromatic ring system containing 3 to 10 ring atoms, at least one ring heteroatom and consisting either of a single ring or of two or more fused rings. Preferably, single rings will contain up to three and bicyclic systems up to four heteroatoms which will preferably be chosen from nitrogen, oxygen and sulfur. When a ring system contains a sulphur atom, the sulphur atom may be present in any one of its oxidation states e.g. —S—, —S(=O)— or —S(=O$_2$)—. Examples of such groups include pyrrolidinyl, imidazolinyl, pyrazolidinyl, piperidyl, piperazinyl, quinuclidinyl, morpholinyl, together with unsaturated or partially unsaturated analogues such as 4,5,6,7-tetrahydro-benzothiophenyl, chromen-4-onyl, 9H-fluorenyl, 3,4-dihydro-2H-benzo-1,4-dioxepinyl, 2,3-dihydro-benzofuranyl, piperidinyl, 1,3-dioxolanyl, 1,3-dioxanyl, 4,5-dihydro-isoxazolyl, tetrahydrofuranyl and morpholinyl.

Heteroaryl, as used herein, refers to a ring system containing 5 to 10 ring atoms, 1 to 4 ring heteroatoms and consisting either of a single aromatic ring or of two or more fused rings, at least one of which is aromatic. Preferably, single rings will contain up to three and bicyclic systems up to four heteroatoms which will preferably be independently chosen from nitrogen, oxygen and sulfur. When a ring system contains a sulphur atom, the sulphur atom may be present in any one of its oxidation states e.g. —S—, —S(=O)— or —S(=O$_2$)—. Examples of such groups include pyridyl, pyridazinyl, pyrimidinyl, pyrazinyl, triazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. Examples of bicyclic groups are benzothiophenyl, benzimidazolyl, benzothiadiazolyl, quinolinyl, cinnolinyl, quinoxalinyl and pyrazolo[1,5-a]pyrimidinyl.

'Saturated ring', as used herein, refers to a ring system in which the atoms in the ring are linked by single bonds and may consist of either a single ring or two or more fused rings.

'Partially unsaturated ring', as used herein, refers to a ring system in which at least two atoms in the ring are linked by a double bond and may consist of either a single ring or two or more fused rings. Partially unsaturated ring systems do not include aromatic rings.

"Optionally substituted" as used herein means the group referred to can be substituted at one or more positions by any one or any combination of the radicals listed thereafter. For most groups, one or more hydrogen atoms are replaced by the radicals listed thereafter. For halogenated groups, for example, haloalkyl groups, one or more halogen atoms are replaced by the radicals listed thereafter.

Suitable salts include those derived from alkali or alkaline earth metals and those derived from ammonia and amines. Preferred cations include sodium, potassium, magnesium, and ammonium cations of the formula $N^+(R^{19}R^{20}R^{21}R^{22})$ wherein $R^{19}$, $R^{20}$, $R^{21}$ and $R^{22}$ are independently selected from hydrogen, $C_1$-$C_6$ alkyl and $C_1$-$C_6$ hydroxyalkyl. Salts of the compounds of Formula I can be prepared by treatment of compounds of Formula I with a metal hydroxide, such as sodium hydroxide, or an amine, such as ammonia, trimethylamine, diethanolamine, 2-methylthiopropylamine, bisallylamine, 2-butoxyethylamine, morpholine, cyclododecylamine, or benzylamine. Amine salts are often preferred forms of the compounds of Formula I because they are water-soluble and lend themselves to the preparation of desirable aqueous based herbicidal compositions.

Acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety.

In another aspect the present invention provides intermediates useful in the preparation of compounds of the invention.

In one embodiment, there are provided intermediates of the formula (IV)

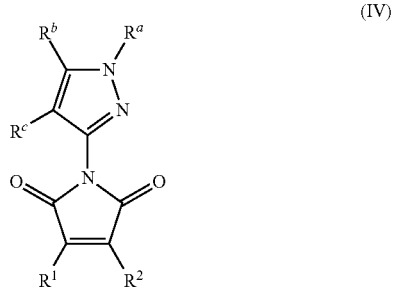

(IV)

wherein $R^a$, $R^b$, $R^c$, $R^1$ and $R^2$ are as defined above.

Compounds of the invention may be prepared by techniques known to the person skilled in the art of organic chemistry. General methods for the production of compounds of formula (I) are described below. Unless otherwise stated in the text, the substituents X, A, $R^1$, $R^2$, $R^3$, $R^a$, $R^b$ and $R^c$ are as defined hereinbefore. The starting materials used for the preparation of the compounds of the invention may be purchased from usual commercial suppliers or may be prepared by known methods. The starting materials as well as the intermediates may be purified before use in the next step by state of the art methodologies such as chromatography, crystallization, distillation and filtration.

For example, compounds of formula (I) wherein $R^3$ is a hydroxyl group may be prepared by reaction of substituted maleic anhydride (V) with amine (VI) in acetic acid to give maleimide (IV), and subsequent reduction with e.g. sodium borohydride to give compound (VII) (compound (I) wherein $R^3$ is hydroxyl), together with regioisomer (VIII) as a side-product (Scheme 1). Suitable conditions for achieving these transformations are disclosed in CH633678. Maleic anhydrides (IV) can be prepared by literature methods (Journal of the Chemical Society, Perkin Transactions 1: Organic and Bio-Organic Chemistry (1972-1999), 1982, p. 215-222, EP1426365 A1, 2004, Journal of Organic Chemistry, 1998, vol. 63, 8, p. 2646-2655).

Scheme 1

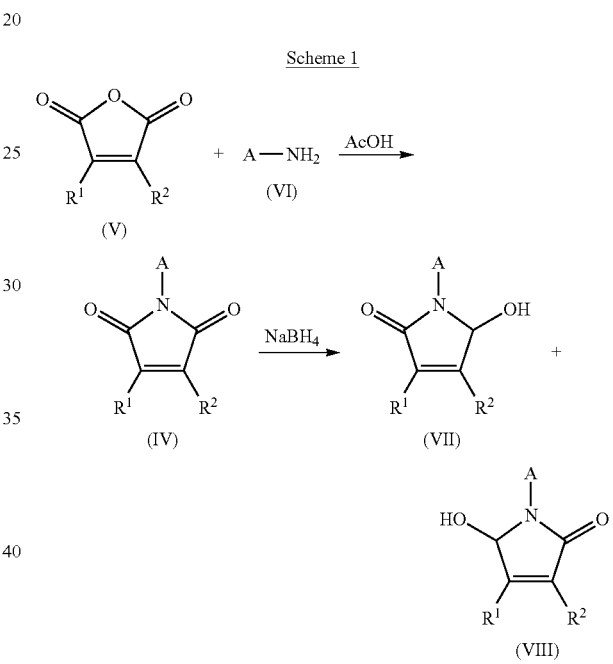

wherein A is an optionally substituted pyrazole ring.

Alternatively compounds of formula (I) wherein $R^3$ is a hydroxyl group may be prepared by reaction of bromolactone (IX) with the appropriate amino pyrazole (VI), in a solvent, such as toluene with a suitable base, such as triethylamine to afford intermediate (X). Heating (X) in acetic anhydride and pyridine affords (XI). Heating (XI) in an acetic acid/water solution affords the desired final compounds (XII) (Scheme 2)

Scheme 2

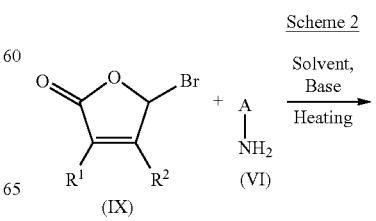

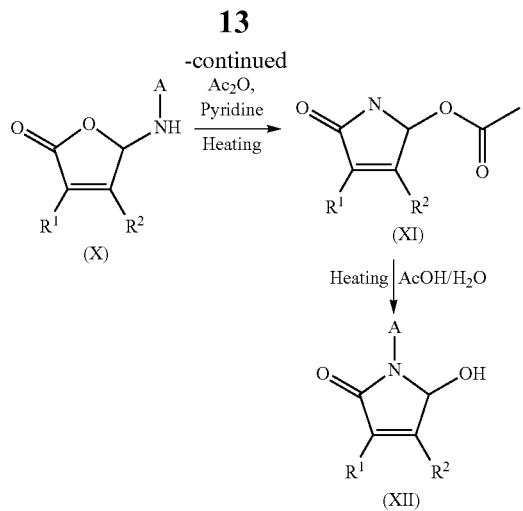

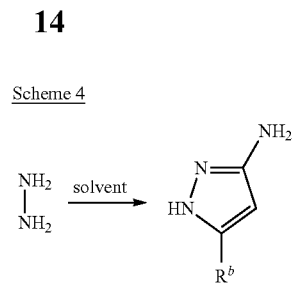

Scheme 4

Alternatively, the hydroxypyrrolones, or indeed compounds of formula (I), can be prepared as shown in Scheme 3, wherein $R^1$, $R^2$ and A are described above.

Alternatively, reaction of an alkyl hydrazine, or an appropriate salt, with a nitrile vinyl chloride (XIII), or its isomers (XIII), in a solvent such as ethanol, with an appropriate base, such as $K_2CO_3$, affords the desired amino pyrazoles (XIV) and undesired isomer (XV) (Scheme 5) as described in *Pharmazie*, 1989, vol. 44, No. 8 p. 535-539 or *Journal of Heterocyclic Chemistry*, 1982, vol. 19, p. 1267-1273.

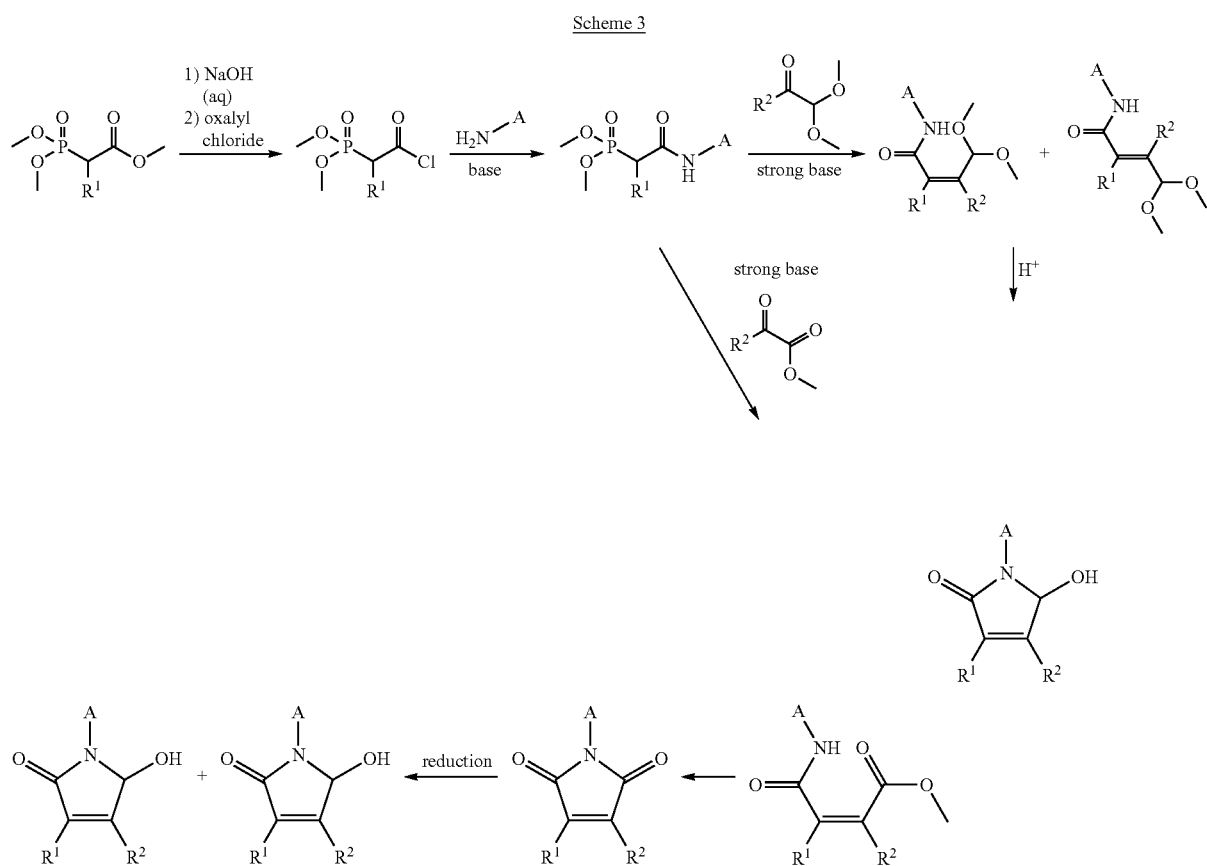

Scheme 3

The relevant amino pyrazoles can be prepared as shown in Schemes 4 to 13.

Reaction of hydrazine, or an appropriate salt, with a β-ketonitrile in a solvent such as ethanol affords the desired amino pyrazoles (VI) where $R^a$ and $R^c$ =H (Scheme 4) as described in *Journal of Medicinal Chemistry*, 2008, vol. 51, No. 15 p. 4672-4684.

Scheme 5

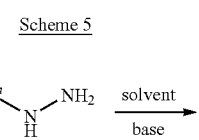

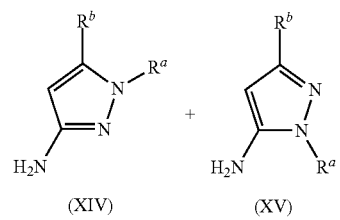

(XIV) + (XV)

Nitrile vinyl chlorides (XIII) can be prepared from the corresponding β-ketonitrile and a suitable chlorination reagent such as PCl₅ or POCl₃, in a suitable solvent, such as dichlormethane as shown in Scheme 5. Alternatively the nitrile vinyl chlorides (XIII) can be prepared from the corresponding ketone (Scheme 6).

Scheme 6

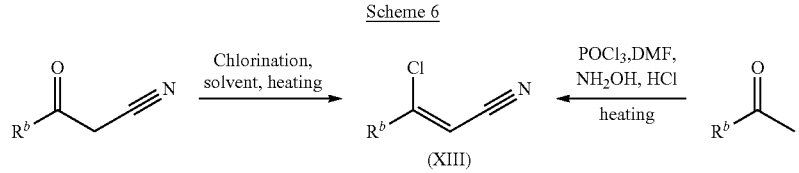

(XIII)

Alternatively nitrile vinyl chlorides (XVII) can be prepared from the corresponding aldehyde and phosphonate (XVI), with an appropriate base, such as LiN(TMS)₂ in an appropriate solvent, such as THF (Scheme 7). Phosphonate (XVI) can be prepared as described in *J. Chem. Soc., Perkin Trans.* 1, 2000, 3311-3316.

Scheme 7

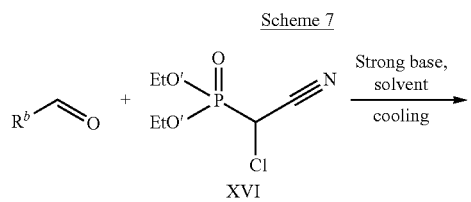

XVI

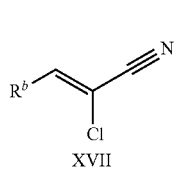

XVII

Alternatively the amino pyrazoles can be prepared from the corresponding pyrazole 3-carboxylates (XVIII). N-alkylation employing an appropriate base, such as tBuOK, in the appropriate solvent, such as THF, with the relevant alkyl halide, followed by ester hydrolysis affords the pyrazole 3-carboxylic acids (XIX). Reaction of (XIX) with DPPA in a solvent, such as tBuOH, and triethylamine affords a mixture of the urea (XX) and the desired amino pyrazole (XXI). (XX) may be further converted into (XXI) under hydrolysis conditions (Scheme 8).

Scheme 8

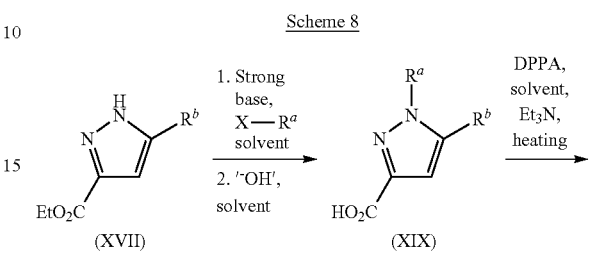

(XVII) → (XIX)

-continued

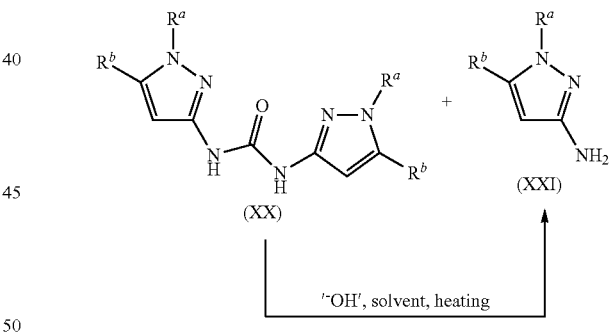

(XX) + (XXI)

Alternatively deprotonation of pyrazole (XXII) with an appropriate base, such as BuLi, followed by quenching with an electrophile, such as halogens, alkyl halides, aldehydes, ketones etc as described in *Journal of Organic Chemistry*, 1984, vol. 49, No. 7 p. 1224-1227, affords (XXIII). Deprotection of the pyrrole masked amine (XXIII), also described in the above reference, affords the desired amino pyrazoles (XXI). Alternatively, further functional group transformations of (XXIII), which will be know to those skilled in the art, can be used to further vary the pyrazole 5-position ($R^b$) before deprotection to (XXI) (Scheme 9).

Scheme 9

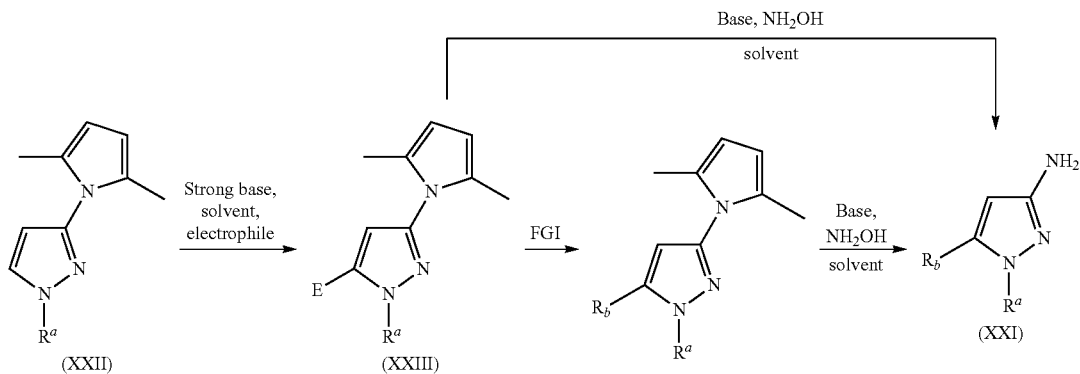

Phthalimide protected pyrazoles (XXIV) can be akylated with an appropriate base such as K$_2$CO$_3$, tBuOK, NaH, NaOH, in an appropriate solvent, such as THF and ether, with the appropriate alkyl halide, to afford (XXV) and varying amounts of undesired (XXVI). Removal of the protecting group, employing, propane-1,2-diamine affords the the desired amino pyrazoles (XXI) (Scheme 10).

Scheme 10

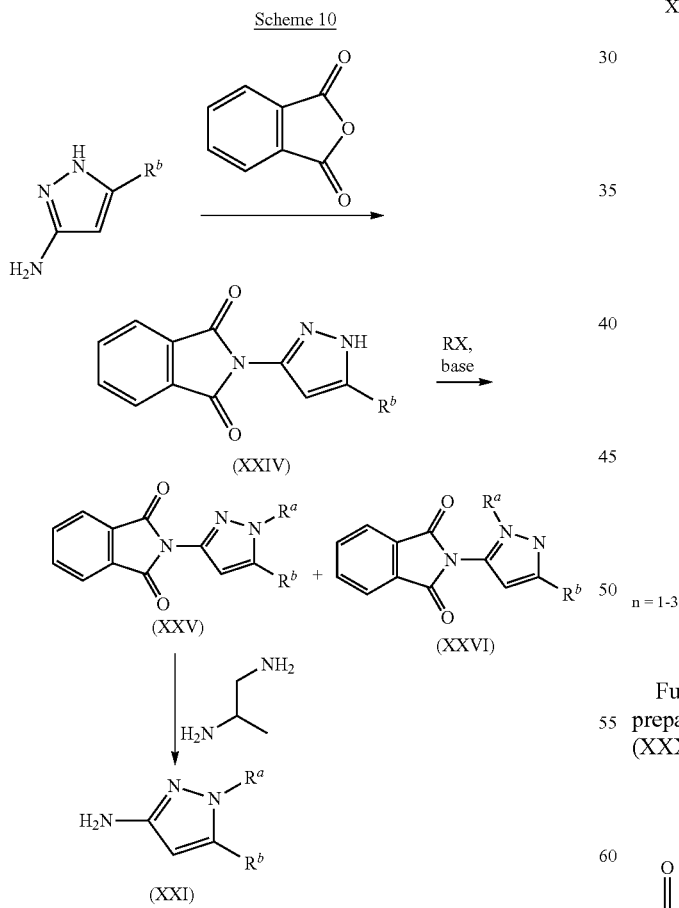

Fused bycyclic amino pyrazoles of type (XXIX) can be prepared from Lactam intermediates (XXVIII) as shown in Scheme 11, wherein R$^{10}$ and R$^{11}$ are, for example, H or C$_1$-C$_6$ alkyl.

Scheme 11

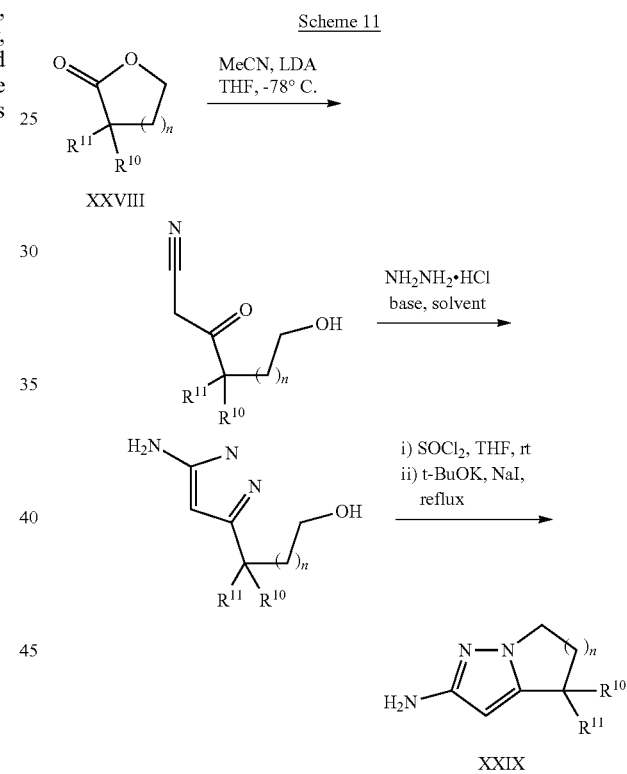

Fused bycyclic amino pyrazoles of type (XXXI) can be prepared from cyclic ketone intermediates intermediates (XXX) as shown in Scheme 12.

Scheme 12

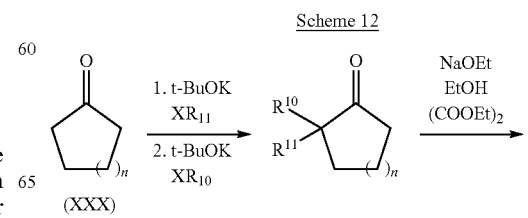

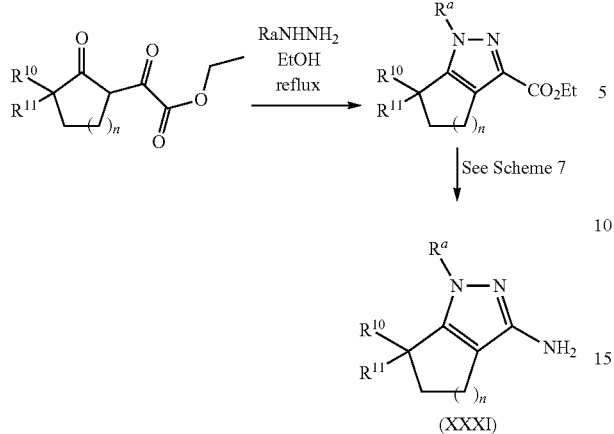
n = 1-3
3-amino-4-nitrile substituted pyrazoles may be prepared as shown in Scheme 13, as reported in the literature. Journal of Heterocyclic Chemistry, 1982, vol. 19, p. 1267-1273.
Scheme 13
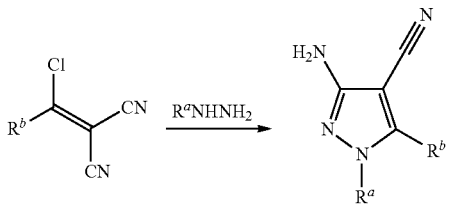
Compound (XXXII) may be halogenated (i), alkylated (ii), acylated (iii), sulfonylated (iv) or alkoxyacylated (v), under standard conditions to access other compounds having different values of $R^3$ (Scheme 14).
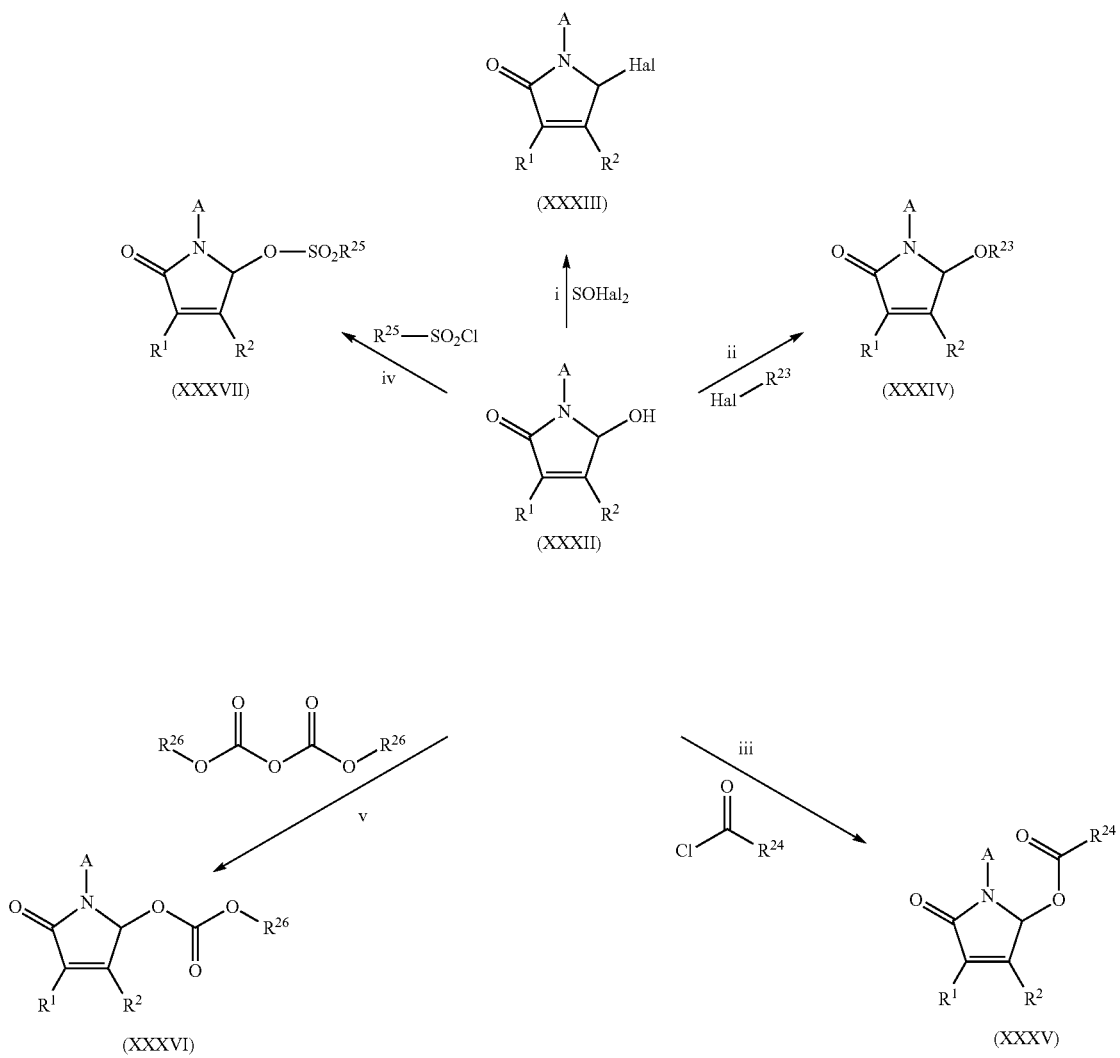

wherein $R^1$ and $R^2$ are as defined above, A is an optionally substituted pyrazole ring, Hal is halogen as defined above, $R^{23}$ is selected from $C_1$-$C_6$ alkyl, $C_2$-$C_6$ alkenyl, $C_2$-$C_6$ alkynyl; $R^{24}$ is selected from H and $C_1$-$C_5$ alkyl, $R^{25}$ is selected from $C_1$-$C_6$ alkyl and $C_6$-$C_{10}$ aryl optionally substituted with 1 to 3 groups independently selected from halogen, $C_1$-$C_3$ alkyl, and $C_1$-$C_3$ alkoxy and $R^{26}$ is selected from $C_1$-$C_5$ alkyl.

Suitable conditions for effecting transformations i to v will be known to those skilled in the art, and are set out for example in J. March, Advanced Organic Chemistry, 4th ed. Wiley, N.Y., 1992, and references cited therein.

The compounds of formula (I) according to the invention can be used as herbicides in unmodified form, as obtained in the synthesis, but they are generally formulated into herbicidal compositions in various ways using formulation adjuvants, such as carriers, solvents and surface-active substances. Therefore, the invention also relates to a herbicidal composition which comprises a herbicidally effective amount of a compound of formula (I) in addition to formulation adjuvants. The formulations can be in various physical forms, e.g. in the form of dusting powders, gels, wettable powders, water-dispersible granules, water-dispersible tablets, effervescent pellets, emulsifiable concentrates, micro-emulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO Specifications for Plant Protection Products, 5th Edition, 1999. Such formulations can either be used directly or they are diluted prior to use. The dilutions can be made, for example, with water, liquid fertilizers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof. The active ingredients can also be contained in very fine microcapsules consisting of a polymer. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art in this connection. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydro-furfuryl alcohol, hexanol, octanol, ethylene glycol, propylene glycol, glycerol, N-methyl-2-pyrrolidone and the like. Water is generally the carrier of choice for diluting the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances, as described, for example, in CFR 180.1001. (c) & (d).

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecyl-benzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in "McCutcheon's Detergents and Emulsifiers Annual" MC Publishing Corp., Ridgewood N.J., 1981.

Further adjuvants that can usually be used in pesticidal formulations include crystallization inhibitors, viscosity modifiers, suspending agents, dyes, anti-oxidants, foaming agents, light absorbers, mixing auxiliaries, antifoams, complexing agents, neutralizing or pH-modifying substances and buffers, corrosion inhibitors, fragrances, wetting agents, take-up enhancers, micronutrients, plasticisers, glidants, lubricants, dispersants, thickeners, antifreezes, microbicides, and also liquid and solid fertilizers.

The compositions according to the invention can additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being of importance. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combination with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyloxide-modified heptamethyltrilsoxanes which are commercially available e.g. as Silwet L-77®, and also perfluorinated surfactants. The concentration of the surface-active substances in relation to the total additive is generally from 1 to 30% by weight. Examples of oil additives consisting of mixtures of oil or mineral oils or derivatives thereof with surfactants are Edenor ME SU®, Turbocharge® (Syngenta AG, CH) or ActipronC (BP Oil UK Limited, GB).

If desired, it is also possible for the mentioned surface-active substances to be used in the formulations on their own, that is to say, without oil additives.

Furthermore, the addition of an organic solvent to the oil additive/surfactant mixture may contribute to an additional enhancement of action. Suitable solvents are, for example, Solvesso® (ESSO) or Aromatic Solvent® (Exxon Corporation). The concentration of such solvents can be from 10 to 80% by weight of the total weight. Oil additives that are present in admixture with solvents are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, for the purpose of enhancing the action of the compositions according to the invention it is also possible for formulations of alkylpyrrolidones (e.g. Agrimax®) to be added to the spray mixture. Formulations of synthetic lattices, e.g. polyacrylamide, polyvinyl compounds or poly-1-p-menthene (e.g. Bond®, Courier® or Emerald®) may also be used. It is also possible for solutions that contain propionic acid, for example Eurogkem Pen-e-trate®, to be added to the spray mixture as action-enhancing agent.

The herbicidal compositions generally comprise from 0.1 to 99% by weight, especially from 0.1 to 95% by weight, compounds of formula (I) and from 1 to 99.9% by weight of a formulation adjuvant which preferably includes from 0 to 25% by weight of a surface-active substance. Whereas commercial products will preferably be formulated as concentrates, the end user will normally employ dilute formulations.

The rates of application of compounds of formula (I) may vary within wide limits and depend on the nature of the soil, the method of application (pre- or post-emergence; seed dressing; application to the seed furrow; no tillage application etc.), the crop plant, the grass or weed to be controlled, the prevailing climatic conditions, and other factors governed by the method of application, the time of application and the target crop. The compounds of formula (I) according to the invention are generally applied at a rate of from 10 to 2000 g/ha, especially from 50 to 1000 g/ha.

Preferred formulations have especially the following compositions (% =percent by weight):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
Granules:
active ingredient: 0.1 to 30%, preferably 0.1 to 15%
solid carrier: 99.5 to 70%, preferably 97 to 85%
The following Examples further illustrate, but do not limit, the invention.
Formulation Examples for Herbicides of Formula (I) (%=% by weight)

| F1. Emulsifiable concentrates | | | | |
|---|---|---|---|---|
| | a) | b) | c) | d) |
| active ingredient | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |

F1. Emulsifiable concentrates

|  | a) | b) | c) | d) |
|---|---|---|---|---|
| octylphenol polyglycol ether (7-8 mol of ethylene oxide) | — | 4% | — | 2% |
| NMP | — | — | 10% | 20% |
| arom. hydrocarbon mixture ($C_9$-$C_{12}$) | 85% | 78% | 55% | 16% |

Emulsions of any desired concentration can be obtained from such concentrates by dilution with water.

F2. Solutions

|  | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture ($C_9$-$C_{12}$) | 75% | 60% | — | — |

The solutions are suitable for use in the form of microdrops.

F3. Wettable powders

|  | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

F4. Coated granules

|  | a) | b) | c) |
|---|---|---|---|
| active ingredient | 0.1% | 5% | 15% |
| highly dispersed silicic acid | 0.9% | 2% | 2% |
| inorganic carrier (diameter 0.1-1 mm) e.g., $CaCO_3$ or $SiO_2$ | 99.0% | 93% | 83% |

The active ingredient is dissolved in methylene chloride and applied to the carrier by spraying, and the solvent is then evaporated off in vacuo.

F5. Coated granules

|  | a) | b) | c) |
|---|---|---|---|
| active ingredient | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g., $CaCO_3$ or $SiO_2$ | 98.0% | 92% | 80% |

The finely ground active ingredient is uniformly applied, in a mixer, to the carrier moistened with polyethylene glycol. Non-dusty coated granules are obtained in this manner.

F6. Extruder granules

|  | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

F7. Dusts

|  | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

F8. Suspension concentrates

|  | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

The invention also provides a method of controlling plants which comprises applying to the plants or to the locus thereof a herbicidally effective amount of a compound of formula (I).

The invention also provides a method of inhibiting plant growth which comprises applying to the plants or to the locus thereof a herbicidally effective amount of a compound of formula (I).

The invention also provides a method of controlling weeds in crops of useful plants, comprising applying to said weeds or to the locus of said weeds, or to said useful plants or to the locus of said useful plants, a compound or a composition of the invention.

The invention also provides a method of selectively controlling grasses and/or weeds in crops of useful plants which comprises applying to the useful plants or locus thereof or to the area of cultivation a herbicidally effective amount of a compound of formula (I).

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example: killing, retardation, leaf burn, albinism, dwarfing and the like. The term "plants" refers to all physical parts of a plant, including seeds, seedlings, saplings, roots, tubers, stems, stalks, foliage, and fruits. The term "locus" is intended to include soil, seeds, and seedlings, as well as established vegetation and includes not only areas where weeds may already be growing, but also areas where weeds have yet to emerge, and also to areas under cultivation with respect to crops of useful plants. "Areas under cultivation" include land on which the crop plants are already growing and land intended for cultivation with such crop plants. The term "weeds" as used herein means any undesired plant, and thus includes not only agronomically important weeds as described below, but also volunteer crop plants.

The compounds of the invention can be applied before or after planting of the crops, before weeds emerge (pre-emergence application) or after weeds emerge (post-emergence application), and are particularly effective when applied post-emergence to the weeds.

Crops of useful plants in which the composition according to the invention can be used include, but are not limited to, perennial crops, such as citrus fruit, grapevines, nuts, oil palms, olives, pome fruit, stone fruit and rubber, and annual arable crops, such as cereals, for example barley and wheat, cotton, oilseed rape, maize, rice, soy beans, sugar beet, sugar cane, sunflowers, ornamentals, switchgrass, turf and vegetables, especially cereals, maize and soy beans.

The grasses and weeds to be controlled may be both monocotyledonous species, for example *Agrostis, Alopecurus, Avena, Brachiaria, Bromus, Cenchrus, Cyperus, Digitaria, Echinochloa, Eriochloa, Lolium, Monochoria, Panicum, Poa, Rottboellia, Sagittaria, Scirpus, Setaria, Sida* and *Sorghum*, and dicotyledonous species, for example *Abutilon, Amaranthus, Chenopodium, Chrysanthemum, Euphorbia, Galium, Ipomoea, Kochia, Nasturtium, Polygonum, Sida, Sinapis, Solanum, Stellaria, Veronica, Viola* and *Xanthium*.

Crops are to be understood as also including those crops which have been rendered tolerant to herbicides or classes of herbicides (e.g. auxins or ALS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®, respectively.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesize such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

Any method of application to weeds/crop of useful plant, or locus thereof, which is routinely used in agriculture may be used, for example application by spray or broadcast method typically after suitable dilution of a compound of formula (I) (whether said compound is formulated and/or in combination with one or more further active ingredients and/or safeners, as described herein).

The compounds of formula (I) according to the invention can also be used in combination with other active ingredients, e.g. other herbicides, and/or insecticides, and/or acaricides, and/or nematocides, and/or molluscicides, and/or fungicides, and/or plant growth regulators. Such mixtures, and the use of such mixtures to control weeds and/or undesired plant growth, form yet further aspects of the invention. For the avoidance of doubt, mixtures of invention also include mixtures of two or more different compounds of formula (I). In particular, the present invention also relates to a composition of the invention which comprises at least one further herbicide in addition to the compound of formula (I).

When a compound of formula (I) is combined with at least one additional herbicide, the following mixtures of the compound of formula (I) are preferred. Compound of formula (I)+acetochlor, compound of formula (I)+acifluorfen, compound of formula (I)+acifluorfen-sodium, compound of formula (I)+aclonifen, compound of formula (I)+acrolein, compound of formula (I)+alachlor, compound of formula (I)+alloxydim, compound of formula (I)+allyl alcohol, compound of formula (I)+ametryn, compound of formula (I)+amicarbazone, compound of formula (I)+amidosulfuron, compound of formula (I)+aminocyclopyrachlor, compound of formula (I)+aminopyralid, compound of formula (I)+amitrole, compound of formula (I)+ammonium sulfamate, compound of formula (I)+anilofos, compound of formula (I)+asulam, compound of formula (I)+atrazine, formula (I)+aviglycine, formula (I)+azafenidin, compound of formula (I)+azimsulfuron, compound of formula (I)+BCPC, compound of formula (I)+beflubutamid, compound of formula (I)+benazolin, formula (I)+bencarbazone, compound of formula (I)+benfluralin, compound of formula (I)+benfuresate, compound of formula (I)+bensulfuron, compound of formula (I)+bensulfuron-methyl, compound of formula (I)+bensulide, compound of formula (I)+bentazone, compound of formula (I)+benzfendizone, compound of formula (I)+benzobicyclon, compound of formula (I)+benzofenap, compound of formula (I)+bicyclopyrone, compound of formula (I)+bifenox, compound of formula (I)+bilanafos, compound of formula (I)+bispyribac, compound of formula (I)+bispyribac-sodium, compound of formula (I)+borax, compound of formula (I)+bromacil, compound of formula (I)+bromobutide, formula (I)+bromophenoxim, compound of formula (I)+bromoxynil, compound of formula (I)+butachlor, compound of formula (I)+butafenacil, compound of formula (I)+butamifos, compound of formula (I)+butralin, compound of formula (I)+butroxydim, compound of formula (I)+butylate, compound of formula (I)+cacodylic acid, compound of formula (I)+calcium chlorate, compound of formula (I)+cafenstrole, compound of formula (I)+carbetamide, compound of formula (I)+carfentrazone, compound of formula (I)+carfentrazone-ethyl, compound of formula (I)+CDEA, compound of formula (I)+CEPC, compound of formula (I)+chlorflurenol, compound of formula (I)+chlorflurenol-methyl, compound of formula (I)+chloridazon, compound of formula (I)+chlorimuron, compound of formula (I)+chlorimuron-ethyl, compound of formula (I)+chloroacetic acid, compound of formula (I)+chlorotoluron, compound of formula (I)+chlorpropham, compound of formula (I)+chlorsulfuron, compound of formula (I)+chlorthal, compound of formula (I)+chlorthal-dimethyl, compound of formula (I)+cinidon-ethyl, compound of formula (I)+cinmethylin, compound of formula (I)+cinosulfuron, compound of formula (I)+cisanilide, compound of formula (I)+clethodim, compound of formula (I)+clodinafop, compound of formula (I)+clodinafop-propargyl, compound of formula (I)+clomazone, compound of formula (I)+clomeprop, compound of formula (I)+clopyralid, compound of formula (I)+cloransulam, compound of formula (I)+cloransulam-methyl, compound of formula (I)+CMA, compound of formula (I)+4-CPB, compound of formula (I)+CPMF, compound of formula (I)+4-CPP, compound of formula (I)+CPPC, compound of formula (I)+cresol, compound of formula (I)+cumyluron, compound of formula (I)+cyanamide, compound of formula (I)+cyanazine, compound of formula (I)+cycloate, compound of formula (I)+cyclosulfamuron, compound of formula (I)+cycloxydim, compound of formula (I)+cyhalofop, compound of formula (I)+cyhalofop-butyl, compound of formula (I)+2,4-D, compound of formula (I)+3,4-DA, compound of formula (I)+daimuron, compound of formula (I)+dalapon, compound of formula (I)+dazomet, compound of formula (I)+2,4-DB, compound of formula (I)+3,4-DB, compound of formula (I)+2,4-DEB, compound of formula (I)+desmedipham, formula (I)+desmetryn, compound of formula (I)+dicamba, compound of formula (I)+dichlobenil, compound of formula (I)+ortho-dichlorobenzene, compound of formula (I)+para-dichlorobenzene, compound of formula (I)+dichlorprop, compound of formula (I)+dichlorprop-P, compound of formula (I)+diclofop, compound of formula (I)+diclofop-methyl, compound of formula (I)+diclosulam, compound of formula (I)+difenzoquat, compound of formula (I)+difenzoquat metilsulfate, compound of formula (I)+diflufenican, compound of formula (I)+diflufenzopyr, compound of formula (I)+dimefuron, compound of formula (I)+dimepiperate, compound of formula (I)+dimethachlor, compound of formula (I)+dimethametryn, compound of formula (I)+dimethenamid, compound of formula (I)+dimethenamid-P, compound of formula (I)+dimethipin, compound of formula (I)+dimethylarsinic acid, compound of formula (I)+dinitramine, compound of formula (I)+dinoterb, compound of formula (I)+diphenamid, formula (I)+dipropetryn, compound of formula (I)+diquat, compound of formula (I)+diquat dibromide, compound of formula (I)+dithiopyr, compound of formula (I)+diuron, compound of formula (I)+DNOC, compound of formula (I)+3,4-DP, compound of formula (I)+DSMA, compound of formula (I)+EBEP, compound of formula (I)+endothal, compound of formula (I)+EPTC, compound of formula (I)+esprocarb, compound of formula (I)+ethalfluralin, compound of formula (I)+ethametsulfuron, compound of formula (I)+ethametsulfuron-methyl, formula (I)+ethephon, compound of formula (I)+ethofumesate, compound of formula (I)+ethoxyfen, compound of formula (I)+ethoxysulfuron, compound of formula (I)+etobenzanid, compound of formual (I)+fenoxaprop, compound of formula (I)+fenoxaprop-P, compound of formula (I)+fenoxaprop-ethyl, compound of formula (I)+fenoxaprop-P-ethyl, compound of formula (I)+fentrazamide, compound of formula (I)+ferrous sulfate, compound of formula (I)+flamprop-M, compound of formula (I)+flazasulfuron, compound of formula (I)+florasulam, compound of formula (I)+fluazifop, compound of formula (I)+fluazifop-butyl, compound of formula (I)+fluazifop-P, compound of formula (I)+fluazifop-P-butyl, formula (I)+fluazolate, compound of formula (I)+flucarbazone, compound of formula (I)+flucarbazone-sodium, compound of formula (I)+flucetosulfuron, compound of formula (I)+fluchloralin, compound of formula (I)+flufenacet, compound of formula (I)+flufenpyr, compound of formula (I)+flufenpyr-ethyl, formula (I)+flumetralin, compound of formula (I)+flumetsulam, compound of formula (I)+flumiclorac, compound of formula (I)+flumiclorac-pentyl, compound of formula (I)+flumioxazin, formula (I)+flumipropin, compound of formula (I)+fluometuron, compound of formula (I)+fluoroglycofen, compound of formula (I)+fluoroglycofen-ethyl, formula (I)+fluoxaprop, formula (I)+flupoxam, formula (I)+flupropacil, compound of formula (I)+flupropanate, compound of formula (I)+flupyrsulfuron, compound of formula (I)+flupyrsulfuron-methyl-sodium, compound of formula (I)+flurenol, compound of formula (I)+fluridone, compound of formula (I)+flurochloridone, compound of formula (I)+fluroxypyr, compound of formula (I)+flurtamone, compound of formula (I)+fluthiacet, compound of formula (I)+fluthiacet-methyl, compound of formula (I)+fomesafen, compound of formula (I)+foramsulfuron, compound of formula (I)+fosamine, compound of formula (I)+glufosinate, compound of formula (I)+glufosinate-ammonium, compound of formula (I)+glyphosate, compound of formula (I)+haluauxifen, compound of formula (I)+halauxifen-methyl, compound of formula (I)+halosulfuron, compound of formula (I)+halosulfuron-methyl, compound of formula (I)+haloxyfop, compound of formula (I)+haloxyfop-P, compound of formula (I)+HC-252, compound of formula (I)+hexazinone, compound of formula (I)+imazamethabenz, compound of formula (I)+imazamethabenz-methyl, compound of formula (I)+imazamox, compound of formula (I)+imazapic, compound of formula (I)+imazapyr, compound of formula (I)+imazaquin, compound of formula (I)+imazethapyr, compound of formula (I)+imazosulfuron, compound of formula (I)+indanofan, compound of formula (I) and indaziflam, compound of formula (I)+iodomethane, compound of formula (I)+iodosulfuron, compound of formula (I)+iodosulfuron-methyl-sodium, compound of formula (I)+ioxynil, compound of formula (I) and ipfencarbazone, compound of formula (I)+isoproturon, compound of formula (I)+isouron, compound of formula (I)+isoxaben, compound of formula (I)+isoxachlortole, compound of formula (I)+isoxaflutole, formula (I)+isoxapyrifop, compound of formula (I)+karbutilate, compound of formula (I)+lactofen, compound of formula (I)+lenacil, compound of formula (I)+linuron, compound of formula (I)+MAA, compound of formula (I)+MAMA, compound of formula (I)+MCPA, compound of formula (I)+MCPA-thioethyl, compound of formula (I)+MCPB, compound of formula (I)+mecoprop, compound of formula (I)+mecoprop-P, compound of formula (I)+mefenacet, compound of formula (I)+mefluidide, compound of formula (I)+mesosulfuron, compound of formula (I)+mesosulfuron-methyl, compound of formula (I)+mesotrione, compound of formula (I)+metam, compound of formula (I)+metamifop, compound of formula (I)+metamitron, compound of formula (I)+metazachlor, compound of formula (I) and metazosulfuron, compound of formula (I)+methabenzthiazuron, formula (I)+methazole, a compound of formula (I) and methiozolin, compound of formula (I)+methylarsonic acid, compound of formula (I)+methyldymron, compound of formula (I)+methyl isothiocyanate, compound of formula (I)+metobenzuron, formula (I)+metobromuron, compound of formula (I)+metolachlor, compound of formula (I)+S-metolachlor, compound of formula (I)+metosulam, compound of formula (I)+metoxuron, compound of formula (I)+metribuzin, compound of formula (I)+metsulfuron, compound of formula (I)+metsulfuron-methyl, compound of formula (I)+MK-616, compound of formula (I)+molinate, compound of formula (I)+monolinuron, a compound of formula (I) and monosulfuron, a compound of formula (I) and monosulfuron-ester compound of formula (I)+MSMA, compound of formula (I)+naproanilide, compound of formula (I)+napropamide, compound of formula (I)+naptalam, formula (I)+NDA-402989, compound of formula (I)+nebuoron, compound of formula (I)+nicosulfuron, formula (I)+nipyraclofen, formula (I)+n-methyl glyphosate, compound of formula (I)+nonanoic acid, compound of formula (I)+norflurazon, compound of formula (I)+oleic acid (fatty acids), compound of formula (I)+orbencarb, compound of formula (I)+orthosulfamuron, compound of formula (I)+oryzalin, compound of formula (I)+oxadiargyl, compound of formula (I)+oxadiazon, compound of formula (I)+oxasulfuron, compound of formula (I)+oxaziclomefone, compound of formula (I)+oxyfluorfen, compound of formula (I)+paraquat, compound of formula (I)+paraquat dichloride, compound of formula (I)+pebulate, compound of formula (I)+pendimethalin, compound of formula (I)+penoxsulam, compound of formula (I)+pentachlorophenol, compound of formula (I)+pentanochlor, compound of formula (I)+pentoxazone, compound of formula (I)+pethoxamid, compound of formula (I)+petrolium oils, compound of formula (I)+phenmedipham, compound of formula (I)+phenmedipham-ethyl, compound of formula (I)+picloram, compound of formula (I)+picolinafen, compound of formula (I)+pinoxaden, compound of formula (I)+piperophos, compound of formula (I)+potassium arsenite, compound of formula (I)+potassium azide, compound of formula (I)+pretilachlor, compound of formula (I)+primisulfuron, compound of formula (I)+primisulfuron-methyl, compound of formula (I)+prodiamine, compound of formula (I)+profluazol, compound of formula (I)+profoxydim, formula (I)+prohexadione-calcium, compound of formula (I)+prometon, compound of formula (I)+prometryn, compound of formula (I)+propachlor, compound of formula (I)+propanil, compound of formula (I)+propaquizafop, compound of formula (I)+propazine, compound of formula (I)+propham, compound of formula (I)+propisochlor, compound of formula (I)+propoxycarbazone, compound of formula (I)+propoxycarbazone-sodium, compound of formula (I)+propyzamide, compound of formula (I)+prosulfocarb, compound of formula (I)+prosulfuron, compound of formula (I)+pyraclonil, compound of formula (I)+pyraflufen, compound of formula (I)+pyraflufen-ethyl, formula (I)+pyrasulfotole, compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyributicarb, compound of formula (I)+pyridafol, compound of formula (I)+pyridate, compound of formula (I)+pyriftalid, compound of formula (I)+pyriminobac, compound of formula (I)+pyriminobac-methyl, compound of formula (I)+pyrimisulfan, compound of formula (I)+pyrithiobac, compound of formula (I)+pyrithiobac-sodium, formula (I)+pyroxasulfone, formula (I)+pyroxulam, compound of formula (I)+quinclorac, compound of formula (I)+quinmerac, compound of formula (I)+quinoclamine, compound of formula (I)+quizalofop, compound of formula (I)+quizalofop-P, compound of formula (I)+quizalofop-ethyl, compound of formula (I)+quizalofop-P-ethyl, compound of formula (I)+rimsulfuron, compound of formula (I)+saflufenacil, compound of formula (I)+sethoxydim, compound of formula (I)+siduron, compound of formula (I)+simazine, compound of formula (I)+simetryn, compound of formula (I)+SMA, compound of formula (I)+sodium arsenite, compound of formula (I)+sodium azide, compound of formula (I)+sodium chlorate, compound of formula (I)+sulcotrione, compound of formula (I)+sulfentrazone, compound of formula (I)+sulfometuron, compound of formula (I)+sulfometuron-methyl, compound of formula (I)+sulfosate, compound of formula (I)+sulfosulfuron, compound of formula (I)+sulfuric acid, compound of formula (I)+tar oils, compound of formula (I)+2,3,6-TBA, compound of formula (I)+TCA, compound of formula (I)+TCA-sodium, formula (I)+tebutam, compound of formula (I)+tebuthiuron, formula (I)+tefuryltrione, compound of formula 1+tembotrione, compound of formula (I)+tepraloxydim, compound of formula (I)+terbacil, compound of formula (I)+terbumeton, compound of formula (I)+terbuthylazine, compound of formula (I)+terbutryn, compound of formula (I)+thenylchlor, compound of formula (I)+thiazafluron, compound of formula (I)+thiazopyr, compound of formula (I)+thifensulfuron, compound of formula (I)+thiencarbazone, compound of formula (I)+thifensulfuron-methyl, compound of formula (I)+thiobencarb, compound of formula (I)+tiocarbazil, compound of formula (I)+topramezone, compound of formula (I)+tralkoxydim, a compound of formula (I) and triafamone compound of formula (I)+tri-allate, compound of formula (I)+triasulfuron, compound of formula (I)+triaziflam, compound of formula (I)+tribenuron, compound of formula (I)+tribenuron-methyl, compound of formula (I)+tricamba, compound of formula (I)+triclopyr, compound of formula (I)+trietazine, compound of formula (I)+trifloxysulfuron, compound of formula (I)+trifloxysulfuron-sodium, compound of formula (I)+trifluralin, compound of formula (I)+triflusulfuron, compound of formula (I)+triflusulfuron-methyl, compound of formula (I)+trifop, compound of formula (I)+trifop-methyl, compound of formula (I)+trihydroxytriazine, compound of formula (I)+trinexapac-ethyl, compound of formula (I)+tritosulfuron, compound of formula (I)+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6) and the compound of formula (I)+VX-573.

In particular, the following mixtures are important:
mixtures of a compound of formula (I) with an acetanilide (e.g. compound of formula (I)+acetochlor, compound of formula (I)+dimethenamid, compound of formula (I)+metolachlor, compound of formula (I)+S-metolachlor, or compound of formula (I)+pretilachlor) or with other inhibitors of VLCFAE (e.g. compound of formala (I)+pyroxasulfone);

mixtures of a compound of formula (I) with an HPPD inhibitor (e.g. compound of formula (I)+isoxaflutole, compound of formula (I)+mesotrione, compound of formula (I)+pyrasulfotole, compound of formula (I)+sulcotrione, compound of formula (I)+tembotrione, compound of formula (I)+topramezone, compound of formula (I)+bicyclopyrone;

mixtures of a compound of formula (I) with a PSII inhibitor (e.g. compound of formula (I)+atrazine, compound of formula (I)+terbuthylazine, compound of formula (I)+ametrin, compound of formula (I)+bromoxinyl);

mixtures of a compound of formula (I) with glyphosate;

mixtures of a compound of formula (I) with glufosinate-ammonium;

mixtures of a compound of formula (I) with a PPO inhibitor (e.g. compound of formula (I)+acifluorfen-sodium, compound of formula (I)+butafenacil, compound of formula (I)+carfentrazone-ethyl, compound of formula (I)+cinidon-ethyl, compound of formula (I)+flumioxazin, compound of formula (I)+fomesafen, compound of formula (I)+lactofen, or compound of formula (I)+SYN 523 ([3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester) (CAS RN 353292-31-6)).

Whilst two-way mixtures of a compound of formula (I) and another herbicide are explicitly disclosed above, the skilled man will appreciate that the invention extends to three-way, and further multiple combinations comprising the above two-way mixtures. In particular, the invention extends to:

mixtures of a compound of formula (I) with a PSII inhibitor and an HPPD inhibitor (e.g. compound of formula (I)+PSII inhibitor+isoxaflutole, compound of formula (I)+PSII inhibitor+mesotrione, compound of formula (I)+PSII inhibitor +pyrasulfotole, compound of formula (I)+PSII inhibitor+sulcotrione, compound of formula (I)+PSII inhibitor+tembotrione, compound of formula (I)+PSII inhibitor+topramezone, compound of formula (I)+PSII inhibitor+bicyclopyrone;

mixtures of a compound of formula (I) with glyphosate and an HPPD inhibitor (e.g. compound of formula (I)+glyphosate+isoxaflutole, compound of formula (I)+glyphosate+mesotrione, compound of formula (I)+glyphosate+pyrasulfotole, compound of formula (I)+glyphosate+sulcotrione, compound of formula (I)+glyphosate+tembotrione, compound of formula (I)+glyphosate+topramezone, compound of formula (I)+glyphosate+bicyclopyrone;

mixtures of a compound of formula (I) with glufosinate-ammonium and an HPPD inhibitor (e.g. compound of formula (I)+glufosinate-ammonium+isoxaflutole, compound of formula (I)+glufosinate-ammonium+mesotrione, compound of formula (I)+glufosinate-ammonium+pyrasulfotole, compound of formula (I)+glufosinate-ammonium+sulcotrione, compound of formula (I)+glufosinate-ammonium+tembotrione, compound of formula (I)+glufosinate-ammonium+topramezone, compound of formula (I)+glufosinate-ammonium+bicyclopyrone;

mixtures of a compound of formula (I) with a VLCFAE inhibitor and an HPPD inhibitor (e.g. compound of formula (I)+S-metolachlor+isoxaflutole, compound of formula (I)+S-metolachlor+mesotrione, compound of formula (I)+S-metolachlor+pyrasulfotole, compound of formula (I)+S-metolachlor+sulcotrione, compound of formula (I)+S-metolachlor+tembotrione, compound of formula (I)+S-metolachlor+topramezone, compound of formula (I)+S-metolachlor+bicyclopyrone, compound of formula (I)+acetochlor+isoxaflutole, compound of formula (I)+acetochlor+mesotrione, compound of formula (I)+acetochlor+pyrasulfotole, compound of formula (I)+acetochlor+sulcotrione, compound of formula (I)+acetochlor+tembotrione, compound of formula (I)+acetochlor+topramezone, compound of formula (I)+acetochlor+bicyclopyrone, compound of formula (I)+pyroxasulfone+isoxaflutole, compound of formula (I)+pyroxasulfone+mesotrione, compound of formula (I)+pyroxasulfone+pyrasulfotole, compound of formula (I)+pyroxasulfone+sulcotrione, compound of formula (I)+pyroxasulfone+tembotrione, compound of formula (I)+pyroxasulfone+topramezone, compound of formula (I)+pyroxasulfone +bicyclopyrone.

Particularly preferred are mixtures of the compound of formula (I) with mesotrione, bicyclopyrone, isoxaflutole, tembotrione, topramezone, sulcotrione, pyrasulfotole, metolachlor, S-metolachlor, acetochlor, pretilachlor, pyroxasulfone, P-dimethenamid, dimethenamid, flufenacet, pethoxamid, atrazine, terbuthylazine, bromoxynil, metribuzin, amicarbazone, bentazone, ametryn, hexazinone, diuron, tebuthiuron, glyphosate, paraquat, diquat, glufosinate, acifluorfen-sodium, butafenacil, carfentrazone-ethyl, cinidon-ethyl, flumioxazin, fomesafen, lactofen, [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester.

The mixing partners of the compound of formula (I) may also be in the form of esters or salts, as mentioned e.g. in The Pesticide Manual, 14th Edition (BCPC), 2006. The reference to acifluorfen-sodium also applies to acifluorfen, the reference to dimethenamid also applies to dimethenamid-P, the reference to glufosinate-ammonium also applies to glufosinate, the reference to bensulfuron-methyl also applies to bensulfuron, the reference to cloransulam-methyl also applies to cloransulam, the reference to flamprop-M also applies to flamprop, and the reference to pyrithiobac-sodium also applies to pyrithiobac, etc.

The mixing ratio of the compound of formula (I) to the mixing partner is preferably from 1:100 to 1000:1.

The mixtures can advantageously be used in the above-mentioned formulations (in which case "active ingredient" relates to the respective mixture of compound of formula (I) with the mixing partner).

The compounds of formula (I) according to the invention can also be used in combination with one or more safeners. Likewise, mixtures of a compound of formula (I) according to the invention with one or more further active ingredients, in particular with one or more further herbicides, can also be used in combination with one or more safeners. The term "safener" as used herein means a chemical that when used in combination with a herbicide reduces the undesirable effects of the herbicide on non-target organisms, for example, a safener protects crops from injury by herbicides but does not prevent the herbicide from killing the weeds. Where a compound of formula (I) is combined with a safener, the following combinations of the compound of formula (I) and the safener are particularly preferred. Compound of formula (I)+AD 67 (MON 4660), compound of formula (I)+benoxacor, compound of formula (I)+cloquintocetmexyl, compound of formula (I)+cyometrinil and a compound of formula (I)+the corresponding (Z) isomer of cyometrinil, compound of formula (I)+cyprosulfamide (CAS RN 221667-31-8), compound of formula (I)+dichlormid, compound of formula (I) and dicyclonon, compound of formula (I) and dietholate, compound of formula (I)+fenchlorazole-ethyl, compound of formula (I) +fenclorim, compound of formula (I)+flurazole, compound of formula (I)+fluxofenim, compound of formula (I)+furilazole and a compound of formula (I)+the corresponding R isomer or furilazome, compound of formula (I)+isoxadifen-ethyl, compound of formula (I)+mefenpyrdiethyl, compound of formula (I) and mephenate, compound of formula (I)+oxabetrinil, compound of formula (I)+naphthalic anhydride (CAS RN 81-84-5), compound of formula (I) and TI-35, compound of formula (I)+N-isopropyl-4-(2-methoxy-benzoylsulfamoyl)-benzamide (CAS RN 221668-34-4) and a compound of formula (I)+N-(2-methoxybenzoyl)-4-[(methylaminocarbonyl)amino]benzenesulfonamide. Particularly preferred are mixtures of a compound of formula (I) with benoxacor, a compound of formula (I) with cloquintocet-mexyl, a compound of formula (I)+cyprosulfamide and a compound of formula (I) with N-(2-methoxybenzoyl)-4-[(methylaminocarbonyl)amino]benzenesulfonamide.

The safeners of the compound of formula (I) may also be in the form of esters or salts, as mentioned e.g. in The Pesticide Manual, 14th Edition (BCPC), 2006. The reference to cloquintocet-mexyl also applies to cloquintocet and to a lithium, sodium, potassium, calcium, magnesium, aluminium, iron, ammonium, quaternary ammonium, sulfonium or phosphonium salt thereof as disclosed in WO02/34048 and the reference to fenchlorazole-ethyl also applies to fenchlorazole, etc.

Preferably the mixing ratio of compound of formula (I) to safener is from 100:1 to 1:10, especially from 20:1 to 1:1.

The mixtures can advantageously be used in the above-mentioned formulations (in which case "active ingredient" relates to the respective mixture of compound of formula (I) and any further active ingredient, in particular a further herbicide, with the safener).

It is possible that the safener and a compound of formula (I) and one or more additional herbicide(s), if any, are applied simultaneously. For example, the safener, a compound of formula (I) and one or more additional herbicide(s), if any, might be applied to the locus pre-emergence or might be applied to the crop post-emergence. It is also possible that the safener and a compound of formula (I) and one or more additional herbicide(s), if any, are applied sequentially. For example, the safener might be applied before sowing the seeds as a seed treatment and a compound of formula (I) and one or more additional herbicides, if any, might be applied to the locus pre-emergence or might be applied to the crop post-emergence.

Preferred mixtures of a compound of formula (I) with further herbicides and safeners include:

Mixtures of a compound of formula (I) with S-metolachlor and a safener, particularly benoxacor.

Mixtures of a compound of formula (I) with isoxaflutole and a safener.

Mixtures of a compound of formula (I) with mesotrione and a safener.

Mixtures of a compound of formula (I) with sulcotrione and a safener.

Mixtures of a compound of formula (I) with tembotrione and a safener.

Mixtures of a compound of formula (I) with topramezone and a safener.

Mixtures of a compound of formula (I) with bicyclopyrone and a safener.

Mixtures of a compound of formula (I) with a PSII inhibitor and a safener.

Mixtures of a compound of formula (I) with a PSII inhibitor and isoxaflutole and a safener.

Mixtures of a compound of formula (I) with a PSII inhibitor and mesotrione and a safener.

Mixtures of a compound of formula (I) with a PSII inhibitor and sulcotrione and a safener.

Mixtures of a compound of formula (I) with a PSII inhibitor and tembotrione and a safener.

Mixtures of a compound of formula (I) with a PSII inhibitor and topramezone and a safener.

Mixtures of a compound of formula (I) with a PSII inhibitor and bicyclopyrone and a safener.

Mixtures of a compound of formula (I) with glyphosate and a safener.

Mixtures of a compound of formula (I) with glyphosate and isoxaflutole and a safener.

Mixtures of a compound of formula (I) with glyphosate and mesotrione and a safener.

Mixtures of a compound of formula (I) with glyphosate and sulcotrione and a safener.

Mixtures of a compound of formula (I) with glyphosate and tembotrione and a safener.

Mixtures of a compound of formula (I) with glyphosate and topramezone and a safener.

Mixtures of a compound of formula (I) with glyphosate and bicyclopyrone and a safener.

Mixtures of a compound of formula (I) with glufosinate-ammonium and a safener.

Mixtures of a compound of formula (I) with glufosinate-ammonium and isoxaflutole and a safener.

Mixtures of a compound of formula (I) with glufosinate-ammonium and mesotrione and a safener.

Mixtures of a compound of formula (I) with glufosinate-ammonium and sulcotrione and a safener.

Mixtures of a compound of formula (I) with glufosinate-ammonium and tembotrione and a safener.

Mixtures of a compound of formula (I) with glufosinate-ammonium and topramezone and a safener.

Mixtures of a compound of formula (I) with glufosinate-ammonium and bicyclopyrone and a safener.

Mixtures of a compound of formula (I) with S-metolachlor and a safener.

Mixtures of a compound of formula (I) with S-metolachlor and isoxaflutole and a safener.

Mixtures of a compound of formula (I) with S-metolachlor and mesotrione and a safener.

Mixtures of a compound of formula (I) with S-metolachlor and sulcotrione and a safener.

Mixtures of a compound of formula (I) with S-metolachlor and tembotrione and a safener.

Mixtures of a compound of formula (I) with S-metolachlor and topramezone and a safener.

Mixtures of a compound of formula (I) with S-metolachlor and bicyclopyrone and a safener.

Mixtures of a compound of formula (I) with pyroxasulfone and a safener.

Mixtures of a compound of formula (I) with pyroxasulfone and isoxaflutole and a safener.

Mixtures of a compound of formula (I) with pyroxasulfone and mesotrione and a safener.

Mixtures of a compound of formula (I) with pyroxasulfone and sulcotrione and a safener.

Mixtures of a compound of formula (I) with pyroxasulfone and tembotrione and a safener.

Mixtures of a compound of formula (I) with pyroxasulfone and topramezone and a safener.

Mixtures of a compound of formula (I) with pyroxasulfone and bicyclopyrone and a safener.

Mixtures of a compound of formula (I) with acetochlor and a safener.

Mixtures of a compound of formula (I) with acetochlor and isoxaflutole and a safener.

Mixtures of a compound of formula (I) with acetochlor and mesotrione and a safener.

Mixtures of a compound of formula (I) with acetochlor and sulcotrione and a safener.

Mixtures of a compound of formula (I) with acetochlor and tembotrione and a safener.

Mixtures of a compound of formula (I) with acetochlor and topramezone and a safener.

Mixtures of a compound of formula (I) with acetochlor and bicyclopyrone and a safener.

Various aspects and embodiments of the present invention will now be illustrated in more detail by way of example. It will be appreciated that modification of detail may be made without departing from the scope of the invention.

For the avoidance of doubt, where a literary reference, patent application, or patent, is cited within the text of this application, the entire text of said citation is herein incorporated by reference.

EXAMPLES

Preparation Examples

The following abbreviations were used in this section: s=singlet; bs=broad singlet; d=doublet; dd=double doublet; dt=double triplet; t=triplet; tt=triple triplet, q=quartet, sept=septet; m=multiplet; RT=retention time, MH$^+$=molecular mass of the molecular cation.

1H NMR spectra were recorded at 400 MHz on a Varian Unity Inova instrument.

Example 1

Preparation of 4-chloro-1-[5-(1,1-dimethylbut-3-enyl)-1-methyl-pyrazol-3-yl]-2-hydroxy-3-methyl-2H-pyrrol-5-one (B6)

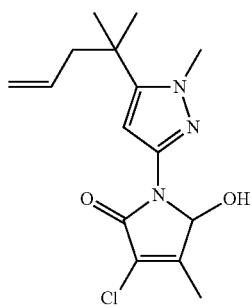 [SMILES: C=CCC(C)(C)c1cc(N2C(=O)C(Cl)=C(C)C2O)nn1C]

Preparation of (2Z)-2-chloro-4,4-dimethyl-hepta-2,6-dienenitrile and (2E)-2-chloro-4,4-dimethyl-hepta-2,6-dienenitrile (Step 1)

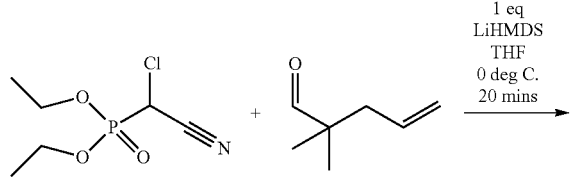

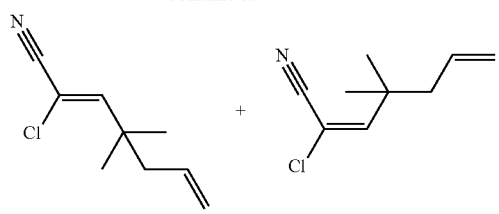

2-chloro-2-diethoxyphosphoryl-acetonitrile (3.80 g, 18.0 mM) was dissolved in 15 ml dry THF then cooled to −10° C. with stirring. Lithium bis(trimethylsilyl)amide (1M in THF, 18.0 ml, 18.0 mM) was added dropwise over 15 minutes to give an amber solution then 2,2-dimethylpent-4-enal (2.12 g, 18.9 mM) was added over 5 minutes and stirred at 0° C. After 20 minutes at 0° C. the reaction was diluted with isohexane (200 ml) then washed sequentially with 2N HCl (aq, 20 ml), water (20 ml), saturated NaHCO$_3$ (aq, 20 ml), water (10 ml), saturated brine (aq, 10 ml), then passed through phase separation cartridge to remove any droplets of water and evaporated to give an amber oil (2.58 g, 84%). $^1$H NMR (CDCl$_3$) showed a 73:27 mixture of geometric isomers:

Major isomer 6.53 (s, 1H), 5.72 (m, 1H), 5.13 (m, 1H), 5.09 (m, 1H), 2.22 (dm, 2H), 1.28 (s, 6H)

Minor isomer 6.56 (s, 1H), 5.72 (m, 1H), 5.17 (m, 1H), 5.14 (m, 1H), 2.27 (dm, 2H), 1.25 (s, 6H)

Preparation of 4,4-dimethylhept-6-en-2-ynenitrile (Step 2)

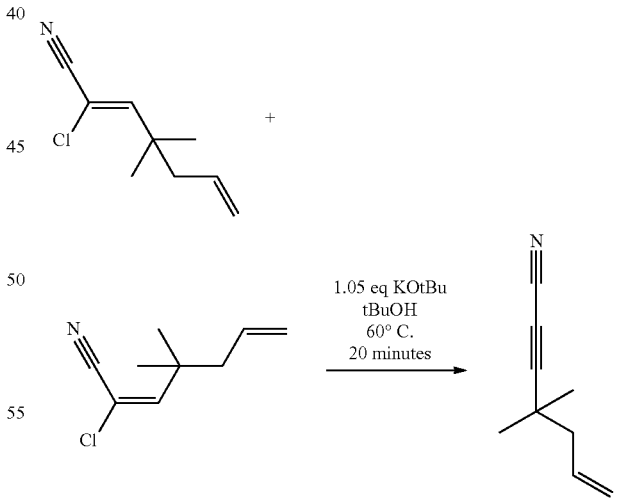

Potassium tert butoxide (1 M in tert butanol, 6.0 ml, 5.97 mM) was added all at once to a mixture of 2-chloro-4,4-dimethyl-hepta-2,6-dienenitrile (73:27 mix of 2-E and 2-Z isomers, 0.965 g, 5.69 mM) and was heated at 60° C. with stirring. After 20 minutes gc showed 4,4-dimethylhept-6-en-2-ynenitrile had formed and was reacted further directly in step 3.

Preparation of 5-(1,1-dimethylbut-3-enyl)-1-methyl-pyrazol-3-amine (Step 3)

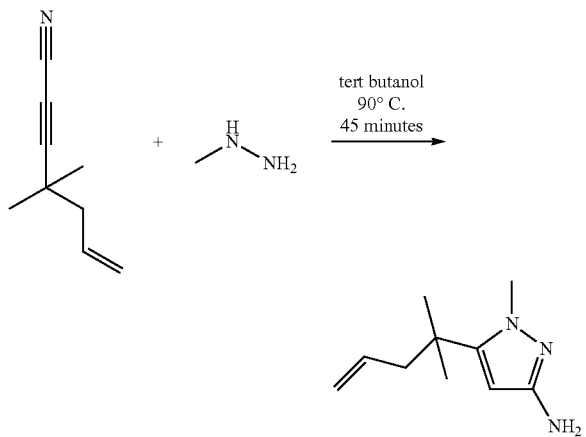

Methyl hydrazine (0.288 g, 6.26 mM) was added to the reaction mixture from step 2 and the reaction was heated at 88° C. with stirring with a reflux condenser fitted. After 45 minutes, the reaction was evaporated and partitioned between water (5 ml), saturated brine (3 ml) and ethyl acetate (20 ml), shaken, then the layers were separated and the aqueous layer was extracted with more ethyl acetate (2×15 ml). The combined ethyl acetate extracts were dried with $Na_2SO_4$, filtered and the filtrate was evaporated to give a brown gum (1.045 g) which was chromatographed to give an amber gum (0.175 g, 17%). $^1$H NMR (CDCl$_3$) 5.60 (m, 1H), 5.40 (s, 1H), 5.04 (dm, 1H), 5.01 (m, 1H), 3.77 (s, 3H), 3.48 (br s, 2H), 2.39 (dm, 2H), 1.30 (s, 6H)

Preparation of 3-chloro-1-[5-(1,1-dimethylbut-3-enyl)-1-methyl-pyrazol-3-yl]-4-methyl-pyrrole-2,5-dione (Step 4)

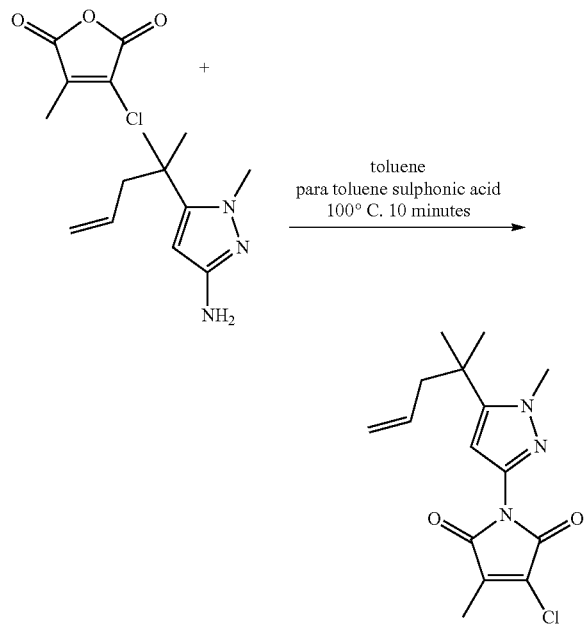

3-chloro-4-methyl-furan-2,5-dione (0.233 g, 1.589 mM) and 5-(1,1-dimethylbut-3-enyl)-1-methyl-pyrazol-3-amine (0.259 g, 1.445 mM) and para toluene sulphonic acid monohydrate (0.003 g, 0.014 mM) were dissolved in toluene (1 ml) and heated with stirring in a microwave at 100° C. for 10 minutes. Ethyl acetate (5 ml) and saturated sodium hydrogen carbonate (aqueous, 1 ml) were added and shaken. The layers were separated and the aqueous layer was extracted with more ethyl acetate (2×2 ml), The combined ethyl acetate extracts were dried with $Na_2SO_4$, filtered and the filtrate was evaporated to give a pale yellow solid (0.470 g) which was chromatographed to give a pale yellow solid (0.356 g, 80%) $^1$H NMR (CDCl$_3$) 6.07 (s, 1H), 5.61 (m, 1H), 5.07 (dm, 1H), 5.04 (m, 1H), 3.98 (s, 3H), 2.45 (dm, 2H), 2.14 (s, 3H), 1.37 (s, 6H).

Preparation of 4-chloro-1-[5-(1,1-dimethylbut-3-enyl)-1-methyl-pyrazol-3-yl]-2-hydroxy-3-methyl-2H-pyrrol-5-one(B6) and 3-chloro-1-[5-(1,1-dimethylbut-3-enyl)-1-methyl-pyrazol-3-yl]-2-hydroxy-4-methyl-2H-pyrrol-5-one (Step 5)

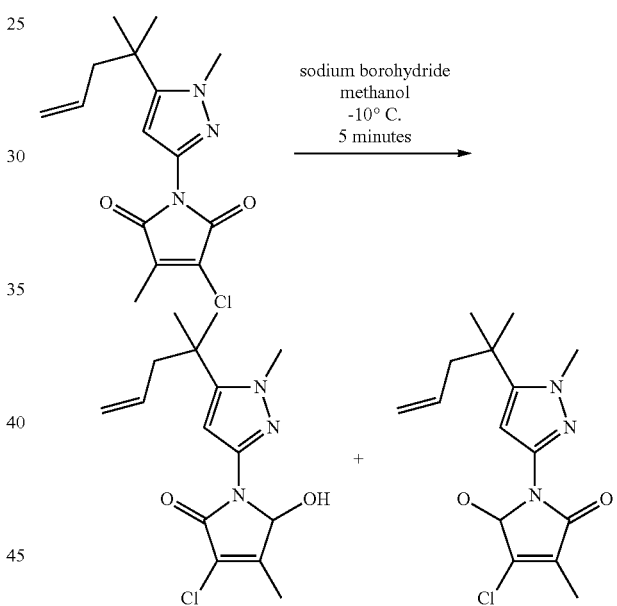

3-chloro-1-[5-(1,1-dimethylbut-3-enyl)-1-methyl-pyrazol-3-yl]-4-methyl-pyrrole-2,5-dione (0.317 g, 1.030 mM) was dissolved in methanol (6 ml) and was cooled to −10° C. with stirring. Sodium borohydride (0.029 g, 0.775 mM) was added. After 5 minutes, acetone was added (0.5 ml) to quench any remaining sodium borohydride. The reaction was evaporated to a give a gum which was partitioned between ethyl acetate (20 ml), water (4 ml) and saturated brine (4 ml) and shaken. The layers were separated and the aqueous layer was extracted with more ethyl acetate (2×10 ml). The combined ethyl acetate extracts were dried with $Na_2SO_4$, filtered and the filtrate was evaporated to give a pale amber gum (0.410 g) which was chromatographed to give an amber gum, 4-chloro-1-[5-(1,1-dimethylbut-3-enyl)-1-methyl-pyrazol-3-yl]-2-hydroxy-3-methyl-2H-pyrrol-5-one,(B6) (0.206 g, 65%). $^1$H NMR (CDCl$_3$) 6.52 (s, 1H), 5.84 (m, 1H), 5.59 (m, 1H), 5.07 (m, 1H), 5.03 (m, 1H), 4.95 (d, 1H), 3.88 (s, 3H), 2.44 (d, 2H), 2.14 (s, 3H), 1.37 (s, 6H) and 3-chloro-1-[5-(1,1-dimethylbut-3-enyl)-1-m ethyl-pyrazol-3-yl]-2-hydroxy-4-methyl-2H-pyrrol-5-one as an amber gum (0.092 g, 29%). ¹H NMR (CDCl₃) 6.49 (s, 1H), 5.87 (m, 1H), 5.59 (m, 1H), 5.07 (m, 1H), 5.03 (m, 1H), 4.97 (d, 1H), 3.87 (s, 3H), 2.44 (d, 2H), 1.95 (s, 3H), 1.37 (s, 6H).

Example 2

Preparation of 4,4-dimethyl-6,7-dihydro-5H-pyrazolo[1,5-a]pyridin-2-amine

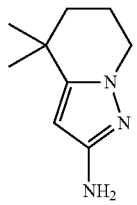

Preparation of 3,3-dimethyltetrahydropyran-2-one (Step 1)

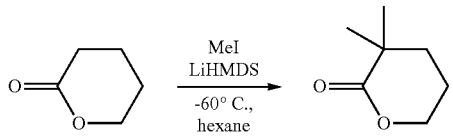

To a solution of δ-valerolactone (0.9279 mL, 10 mmol) and iodomethane (2.49 mL, 40 mmol) in THF (20 mL) at −78° C., was slowly added a solution of LiHMDS (1.0 mol/L) in HEXANE (22 mL, 22 mmol). The addition was complete in 30 minutes keeping the temperature around −60° C. all the time. The reaction was left to slowly warm up and was stirred at rt overnight. Acetic acid (~2 ml) was added to the reaction (causing the precipitation of white solid) and the whole mixture was concentrated. The residue was purified by column chromatography (gradient of EtOAc in hexane) (860 mg). ¹H NMR (CDCl₃) 4.35 (t, 2H); 1.91 (quint, 2H); 1.76 (t, 2H); 1.30 (s, 6H).

Preparation of 7-hydroxy-4,4-dimethyl-3-oxo-heptanenitrile (Step 2)

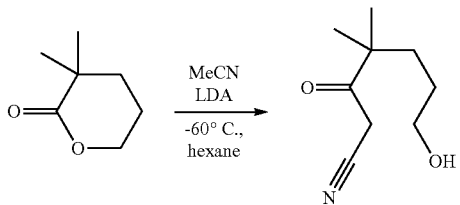

To a solution of N-isopropylpropan-2-amine (1.04 mL, 7.38 mmol) in tetrahydrofuran (13.4 mL) at −78° C., was slowly added a solution of n-butyllithium (3.4 mL, 8.39 mmol). This mixture was stirred for 5 min before adding acetonitrile (0.386 mL, 7.38 mmol) and 10 min later a solution 3,3-dimethyltetrahydropyran-2-one (0.860 g, 6.71 mmol) in THF (6.71 mL). The reaction was then left to slowly warm up and was quenched with NH4Cl after 6 h (~5° C.). The reaction was left sitting at rt overnight. The aqueous layer was then extracted with EtOAc. The combined organic layers were washed with brine, dried over MgSO4 and concentrated. (578 mg) ¹H NMR (CDCl₃) 3.92 (dt, 1H); 3.70 (dd, 1H); 2.73 (d, 1H); 2.67 (d, 1H); 2.42 (br s, 1H); 1.92 (dt, 1H); 1.88-1.77 (m, 1H); 1.42-1.37 (m, 1H); 1.29-1.23 (m, 1H); 1.05 (s, 3H); 1.00 (s, 3H).

Preparation of 3-(5-amino-1H-pyrazol-3-yl)-3-methyl-butan-1-ol (Step 3)

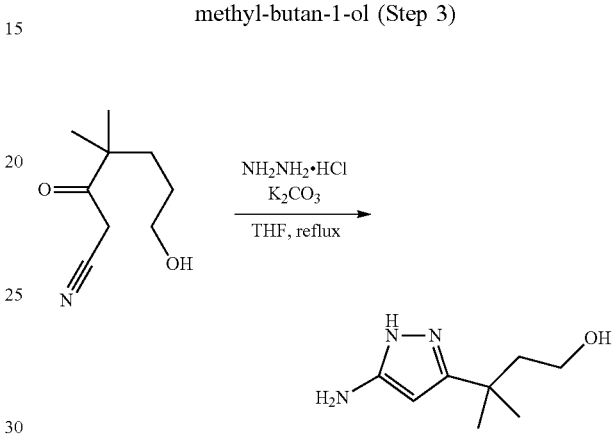

To a solution of 7-hydroxy-4,4-dimethyl-3-oxo-heptanenitrile (0.578 g, 3.42 mmol) in ethanol (6.83 mL) was added hydrazine hydrochloride (0.351 g, 5.12 mmol) followed by K₂CO₃ (0.708 g, 5.12 mmol). The reaction mixture was refluxed under N₂ overnight. The reaction was concentrated in vacuo. The residue was purified by column chromatography (gradient of MeOH in DCM). (300 mg). ¹H NMR (CDCl₃) 7.43 (br s, 1H); 5.43 (s, 1H); 3.85 (br s, 2H); 3.62-3.54 (m, 2H); 1.69-1.60 (m, 2H); 1.54-1.38 (m, 2H); 1.26 (s, 3H); 1.18 (s, 3H).

Preparation of 4,4-dimethyl-6,7-dihydro-5H-pyrazolo[1,5-a]pyridin-2-amine (Step 5)

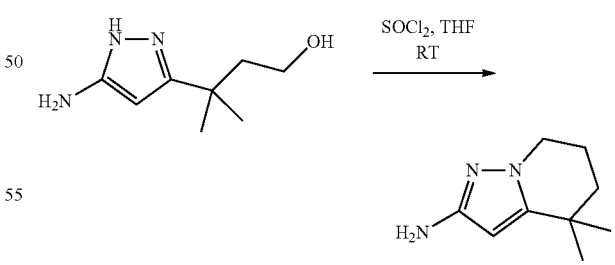

To a solution of 3-(5-amino-1H-pyrazol-3-yl)-3-methyl-butan-1-ol (0.300 g, 1.64 mmol) in tetrahydrofuran (9.82 mL) at rt was added thionyl chloride (0.597 mL, 8.19 mmol). The reaction mixture was stirred at rt for 2 h and checked by LCMS. Only the cyclic material was detected. The reaction was then quenched with water and extracted with EtOAc. The combined organic layer was washed with brine, then dried over MgSO₄ and concentrated. ¹H NMR (CDCl₃) (142 mg). 5.38 (s, 1H); 3.88 (t, 2H); 3.63 (br s, 2H); 2.06-1.98 (m, 2H); 1.68-1.61 (m, 2H); 1.25 (s, 6H).

Example 3

Preparation of 1-ethyl-6,6-dimethyl-4,5-dihydrocyclopenta[c]pyrazol-3-amine

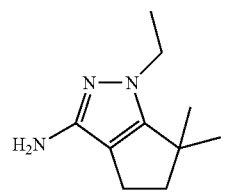

Preparation of ethyl 2-(3,3-dimethyl-2-oxo-cyclopentyl)-2-oxo-acetate (Step 1)

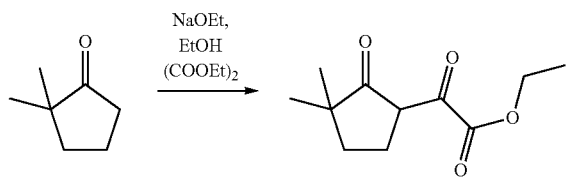

To a solution of sodium ethoxide (3 g, 44.1 mmol) in ethanol (15 ml) at −15° C. under $N_2$ was added slowly a solution of 2,2-dimethylcyclopentanone (5 g, 44.6 mmol) and diethyl oxalate (6.514192 g, 6.048 mL, 44.6 mmol) in ethanol (15 mL). The resulting mixture was stirred at −15° C. for 15 min and then the cold bath was removed. The reaction was then stirred at rt overnight. The reaction was quenched with HCl. It was then extracted with DCM. The combined chlorinated layers were washed with water, dried over $MgSO_4$ and concentrated. (8.2 g) $^1$H NMR ($CDCl_3$) 4.36 (q, 2H); 2.88 (t, 2H); 1.81 (t, 2H); 1.41 (t, 3H); 1.16 (s, 6H).

Preparation of 1-ethyl-3,6,6-trimethyl-4,5-dihydro-cyclopenta[c]pyrazole (Step 2)

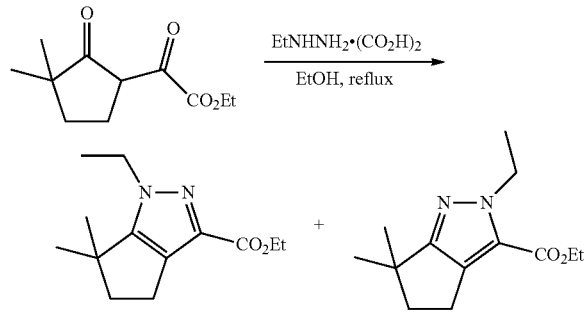

To a solution of ethyl 2-(3,3-dimethyl-2-oxo-cyclopentyl)-2-oxo-acetate (7.7 g, 36.3 mmol) in ethanol (150 ml) was added ethylhydrazine oxalate (6.0 g, 40 mmol). The resulting mixture was heated at reflux for 3.5 h. It was then cooled down and concentrated in vacuo. The residue was taken into DCM and washed with $NaHCO_3$. The chlorinated layer was then dried over $MgSO_4$ and concentrated. The residue was then purified by column chromatography (gradient of EtOAc in hexane)

Pure regioisomer 1-Et-5-COOEt: (1.9 g). $^1$H NMR ($CDCl_3$) 4.53 (q, 2H); 4.33 (q, 2H); 2.76 (m, 2H); 2.21 (m, 3H); 1.38 (t, 3H); 1.34 (t, 3H); 1.21 (s, 6H)

Pure regioisomer 1-Et-3-COOEt: (5.2 g). $^1$H NMR ($CDCl_3$) 4.38 (q, 2H); 4.18 (q, 2H); 2.73 (t, 2H); 2.38 (t, 3H); 1.48 (t, 3H); 1.38 (t, 3H); 1.33 (s, 6H).

Preparation of 1-ethyl-6,6-dimethyl-4,5-dihydrocyclopenta[c]pyrazole-3-carboxylic acid (Step 3)

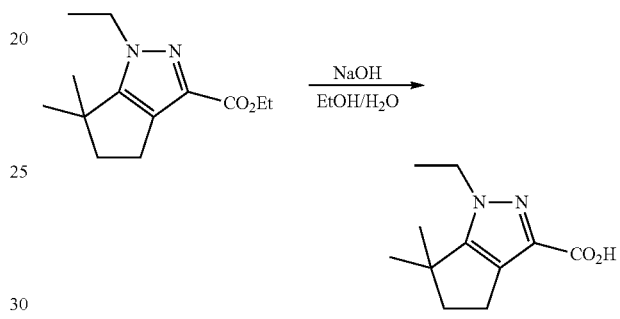

To a solution of pyrazole-3-ethyl-carboxylic ester (5.2 g, 22 mmol) in ethanol (150 ml) was added a 2N solution of sodium hydroxide (25 ml). The resulting mixture was stirred at rt for 7 h. It was concentrated in vacuo and the residue was taken into water. It was then cooled into an ice bath and acidified with 2N HCl. A white solid precipitated out and was filtered off, washed with water and air dried. $^1$H NMR ($CDCl_3$) (4.58 g) 4.13 (q, 2H); 2.76 (t, 2H); 2.39 (t, 3H); 1.48 (t, 3H); 1.38 (s, 6H).

Preparation of 1-ethyl-6,6-dimethyl-4,5-dihydrocyclopenta[c]pyrazol-3-amine (Step 4)

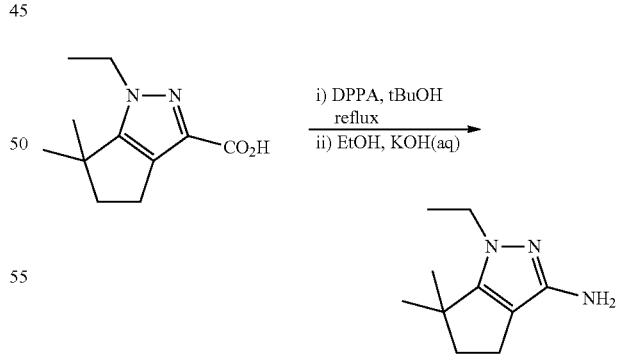

To a suspension of 1-ethyl-6,6-dimethyl-4,5-dihydrocyclopenta[c]pyrazole-3-carboxylic acid (625 mg, 3 mmol) in t-BuOH (15 mL) was added DPPA (0.712 mL, 3.3 mmol) and then $Et_3N$ (0.250 mL, 3.6 mmol). The reaction mixture was heated to reflux. No exotherm was noticed (or controlled by reflux) and a small amount of $N_2$ bubbled away. After several LCMS checks, the reaction was heated at reflux overnight. The reaction was then checked by LCMS.

The reaction was quenched with K$_2$CO$_3$ and extracted with EtOAc. The combined organic layers were washed with brine, then dried over MgSO$_4$ and concentrated. (1.526 g) (contained (PhO)$_2$POOH). $^1$H NMR (CDCl$_3$) 3.94 (q, 2H); 2.66 (br t, 2H); 2.29 (t, 2H); 1.40 (t, 3H); 1.31 (s, 6H).

To a solution of the crude urea, from above, (192 mg, 0.5 mmol) in ethanol (0.2 mL) at rt was added a solution of potassium hydroxide 20 wt % in water (2 mL) in a microwave vial. The vial was then was irradiated at 160° C. for 30 min, generating 15-20 bars of pressure. The reaction was then checked by LCMS, quenched with water and extracted with EtOAc. The combined organics were washed with brine, dried over MgSO$_4$ and concentrated.

(65 mg). $^1$H NMR (CDCl$_3$) 3.85 (q, 2H); 3.45 (br s, 2H); 2.41 (t, 2H); 2.27 (t, 2H); 1.38 (t, 3H); 1.29 (s, 6H).

Example 4

4-chloro-2-hydroxy-1-(5-iodo-1-methyl-pyrazol-3-yl)-3-methyl-2H-pyrrol-5-one (B8)

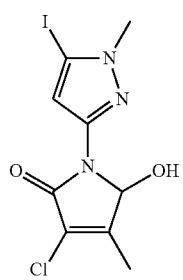 [SMILES: CC1=C(Cl)C(=O)N(c2cc(I)n(C)n2)C1O]

Preparation of 3-(2,5-dimethylpyrrol-1-yl)-5-iodo-1-methyl-pyrazole (Step 1)

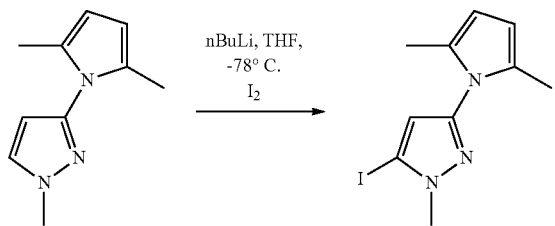

A stirred solution of 3-(2,5-dimethylpyrrol-1-yl)-1-methyl-pyrazole (2.500 g, 14.27 mmol) in tetrahydrofuran (40 mL) was cooled to −78° C. under an atmosphere of nitrogen. n-Butyllithium (1.6 mol in hexanes) (9.8 mL, 15.69 mmol) was added over 15 mins. The resulting solution was stirred at −78° C. for 2 hours. Iodine (3.621 g, 14.27 mmol) was dissolved in THF (10 mL) and added over 10 mins, maintaining a temperature below −60 C. The reaction mixture was stirred cold for a further 10 minutes and then allowed to warm slowly to ambient temperature over a period of 1 hour. 2M Hydrochloric acid was added to quench the reaction. Dichloromethane was added and the layers separated. The aqueous layer was extracted three times with dichloromethane. The combined organics washed with saturated aqueous sodium metabisulfite, dried over MgSO$_4$ and concentrated in vacuo to brown oil. Chromatography on silica gel gave a white solid (2.952 g, 69%). $^1$H NMR (CDCl$_3$) δ 6.34 (1H,s), 5.86 (2H,s), 3.96 (3H, s), 2.11 (6H,s).

Preparation of 5-iodo-1-methyl-pyrazol-3-amine (Step 2)

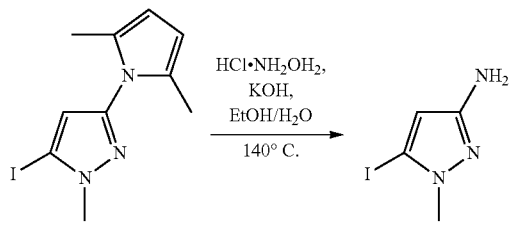

To a stirred solution of 3-(2,5-dimethylpyrrol-1-yl)-5-iodo-1-methyl-pyrazole (1.00 g, 3.32 mmol) and hydroxylamine hydrochloride (1.17 g, 16.6 mmol) in ethanol (10 mL), was added potassium hydroxide (0.466 g, 8.30 mmol) dissolved in water (5 mL). The solution was heated with stirring at 140° C. for one hour under microwave irradiation. Water and dichloromethane were added and the layers separated. The aqueous layer was extracted three times with dichloromethane. The combined organics washed with water, dried over MgSO$_4$ and concentrated in vacuo to a brown oil. Chromatography on silica gel gave an orange solid (0.348 g, 47%). $^1$H NMR (CDCl$_3$) δ 5.77 (s,1H), 3.74 (s, 3H), 3.63 (br. s, 2H).

Preparation of 3-chloro-1-(5-iodo-1-methyl-pyrazol-3-yl)-4-methyl-pyrrole-2,5-dione (Step 3)

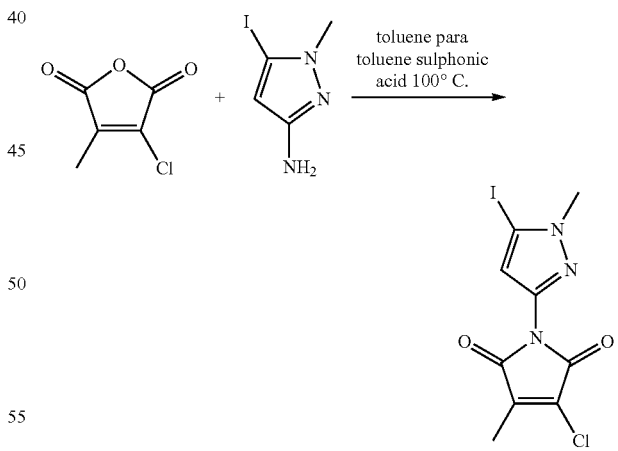

To a stirred solution of 5-iodo-1-methyl-pyrazol-3-amine (0.878 g, 3.94 mmol) and p-toluene sulphonic acid (0.136 g, 0.79 mmol) in toluene (40 mL), was added 3-chloro-4-methyl-furan-2,5-dione (0.635 g, 4.33 mmol.) The solution was heated at 110 C for one hour and then allowed to cool to ambient temperature. The solution was then concentrated in vacuo to brown oil. Chromatography on silica gel gave an orange solid (0.890 g, 64%). $^1$H NMR (CDCl$_3$) δ 6.49 (s, 1H), 3.96 (s, 3H), 2.15 (s, 3H).

Preparation of 3-chloro-2-hydroxy-1-(5-iodo-1-methyl-pyrazol-3-yl)-4-methyl-2H-pyrrol-5-one and 4-chloro-2-hydroxy-1-(5-iodo-1-methyl-pyrazol-3-yl)-3-methyl-2H-pyrrol-5-one (B8) (Step 4)

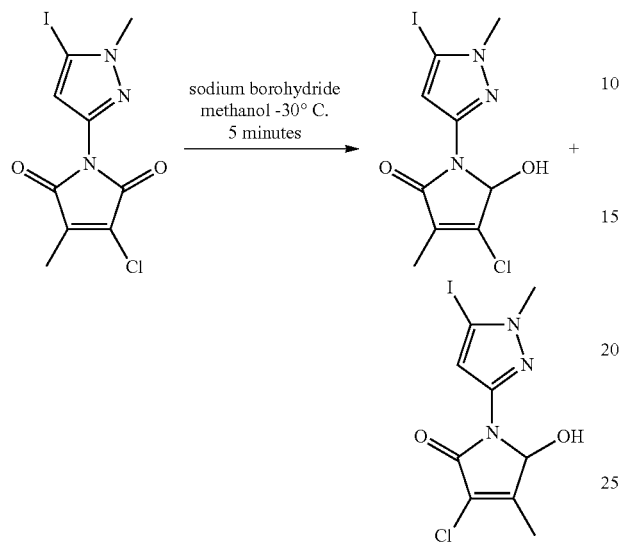

To 3-chloro-1-(5-iodo-1-methyl-pyrazol-3-yl)-4-methyl-pyrrole-2,5-dione (0.850 g, 2.42 mmol) in methanol (10 mL) and tetrahydrofuran (5 mL) at −30 C, was added sodium borohydride (0.103 g, 2.66 mmol). The solution was stirred for one hour. Water and ethyl acetate were added and the layers separated. The aqueous layer was extracted three times with ethyl acetate. The combined organics were washed with water, dried over MgSO$_4$ and concentrated in vacuo to afford a white solid. Chromatography on silica gel gave 3-chloro-2-hydroxy-1-(5-iodo-1-methyl-pyrazol-3-yl)-4-methyl-2H-pyrrol-5-one (B8) (0.220 g, 26%) and 4-chloro-2-hydroxy-1-(5-iodo-1-methyl-pyrazol-3-yl)-3-methyl-2H-pyrrol-5-one (0.459 g, 54%). 3-chloro-2-hydroxy-1-(5-iodo-1-methyl-pyrazol-3-yl)-4-methyl-2H-pyrrol-5-one $^1$H NMR (CDCl$_3$) δ 6.89 (s, 1H), 5.87 (m, 1H), 4.54 (d, 1H), 3.86 (s, 3H), 1.96 (s, 3H). 4-chloro-2-hydroxy-1-(5-iodo-1-methyl-pyrazol-3-yl)-3-methyl-2H-pyrrol-5-one $^1$H NMR (CDCl$_3$) δ 6.93 (s, 1H), 5.86 (d, 1H), 4.56 (d, 1H), 3.86 (s, 3H), 2.15 (s, 3H).

Example 5

Preparation of 4-chloro-2-hydroxy-3-methyl-1-[1-methyl-5-(2-methylprop-1-enyl)pyrazol-3-yl]-2H-pyrrol-5-one (B7)

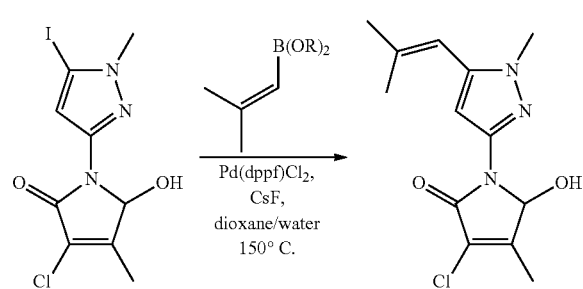

4-chloro-2-hydroxy-1-(5-iodo-1-methyl-pyrazol-3-yl)-3-methyl-2H-pyrrol-5-one (0.300 g, 0.85 mmol) 4,4,5,5-tetramethyl-2-(2-methylprop-1-enyl)-1,3,2-dioxaborolane (0.154 g, 0.85 mmol), cesium fluoride (0.258 g, 1.70 mmol) and [1,1'-Bis(diphenylphosphino)ferrocene]dichloropalladium (II) (0.031 g, 0.042 mmol) combined in 1,4-dioxane (3 mL) and water (1 mL). The stirred solution heated to 150 C for 20 minutes under microwave irradiation. Water and dichloromethane were added and the layers separated. The aqueous layer was extracted three times with dichloromethane. The combined organics washed with water, dried over MgSO$_4$ and concentrated in vacuo to brown oil. Chromatography on silica gel gave a white solid (0.137 g, 57%, mpt 139-142 C). $^1$H NMR CDCl$_3$ δ 6.65 (s, 1H), 5.97 (m, 1H), 5.88 (d, 1H), 4.92 (d, 1H), 3.71 (s, 3H), 2.15 (s, 3H), 1.96 (d, 3H), 1.90 (d, 3H).

Example 6

Preparation of 4-chloro-2-hydroxy-3-methyl-1-[1-methyl-5-(3-methylbut-2-enyl)pyrazol-3-yl]-2H-pyrrol-5-one (B10)

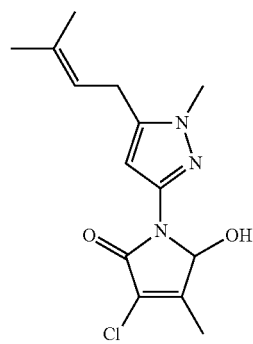 [SMILES: CC(C)=CCc1cc(N2C(=O)C(Cl)=C(C)C2O)nn1C]

Preparation of 3-(2,5-dimethylpyrrol-1-yl)-1-methyl-5-(3-methylbut-2-enyl)pyrazole (Step 1)

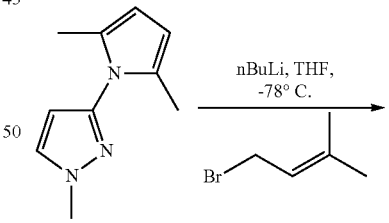

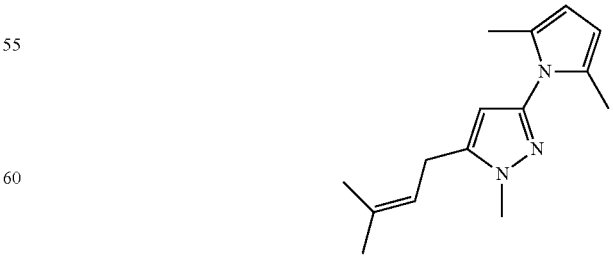

A stirred solution of 3-(2,5-dimethylpyrrol-1-yl)-1-methyl-pyrazole (2.000 g, 11.41 mmol) in tetrahydrofuran (15 mL) was cooled to −78° C. under an atmosphere of nitrogen. Butyllithium (1.6 mol in hexanes) (7.8 mL, 12.55 mmol) was then added over 15 mins. The resulting solution was stirred at −78° C. for 2 hours. 1-bromo-3-methyl-but-2-ene (1.701 g, 11.41 mmol) dissolved in THF (5 mL) was then added over 10 mins, maintaining a temperature below −60° C. The reaction mixture was stirred cold for a further 10 minutes and then allowed to warm slowly to ambient temperature over a period of 1 hour. Saturated aqueous ammonium chloride was added to quench the reaction. Ethyl acetate was then added and the layers separated. The aqueous layer was extracted three times with ethyl acetate. The combined organics washed with water, dried over MgSO$_4$ and concentrated in vacuo to brown oil. Chromatography on silica gel gave yellow oil 1.728 g (62%). $^1$H NMR (CDCl$_3$) δ 5.90 (s, 1H), 5.83 (s, 2H), 5.30-5.25 (m, 1H), 3.79 (s, 3H), 3.36-3.32 (m, 2H), 2.11 (s, 6H), 1.78 (s, 3H), 1.73 (s, 3H).

Preparation of 1-methyl-5-(3-methylbut-2-enyl)pyrazol-3-amine (Step 2)

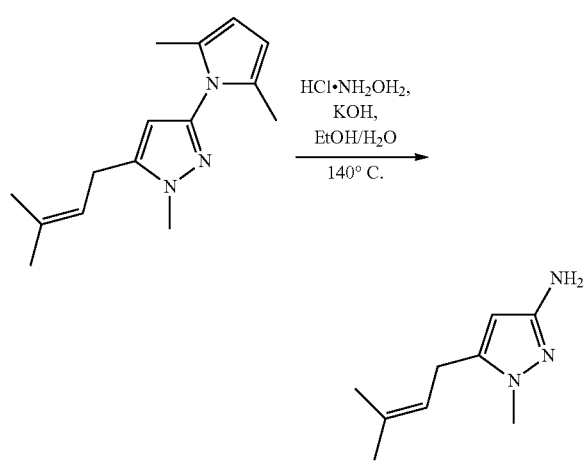

To a stirred solution of 3-(2,5-dimethylpyrrol-1-yl)-1-methyl-5-(3-methylbut-2-enyl)pyrazole (1.316 g, 5.41 mmol) and hydroxylamine hydrochloride (1.898 g, 27.03 mmol,) in ethanol (10 mL), was added potassium hydroxide (0.758 g, 13.52 mmol) dissolved in water (5 mL). The solution was heated with stirring at 140° C. for one hour under microwave irradiation. Water and dichloromethane were added and the layers separated. The aqueous layer was extracted three times with dichloromethane. The combined organics washed with water, dried over MgSO$_4$ and concentrated in vacuo to orange oil. Chromatography on silica gel gave yellow oil (0.642 g, 71%)
$^1$H NMR (CDCl$_3$) δ 5.38 (s, 1H), 5.24-5.18 (m, 1H), 3.58 (s, 3H), 3.55-3.46 (br. s, 2H), 3.20-3.17 (m, 2H), 1.75 (s, 3H), 1.69 (s, 3H)

Preparation of 3-chloro-4-methyl-1-[1-methyl-5-(3-methylbut-2-enyl)pyrazol-3-yl]pyrrole-2,5-dione (Step

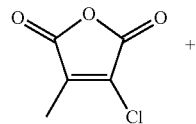

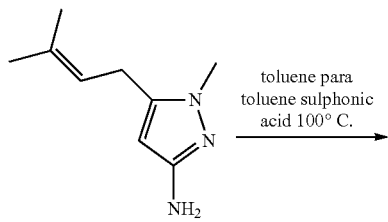

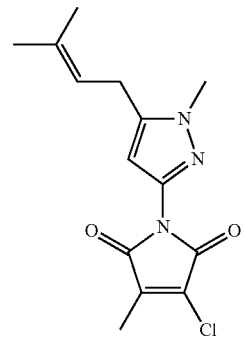

To a stirred solution of 1-methyl-5-(3-methylbut-2-enyl)pyrazol-3-amine (0.321 g, 1.94 mmol) and p-toluene sulphonic acid (0.067 g, 0.39 mmol) in toluene (10 mL) was added 3-chloro-4-methyl-furan-2,5-dione (0.285 g, 1.94 mmol.) The solution was heated at 85° C. for two hours and then allowed to cool to ambient temperature. The solution was then concentrated in vacuo to an orange oil. Chromatography on silica gel gave a yellow solid (0.399 g, 70%). $^1$H NMR (CDCl$_3$) δ 6.05 (s, 1H), 5.27-5.23 (m, 1H), 3.79 (s, 3H), 3.33-3.29 (m, 2H), 2.14 (s, 3H), 1.76 (s, 3H), 1.70 (s, 3H).

Preparation of 3-chloro-2-hydroxy-4-methyl-1-[1-methyl-5-(3-methylbut-2-enyl)pyrazol-3-yl]-2H-pyrrol-5-one and 4-chloro-2-hydroxy-3-methyl-1-[1-methyl-5-(3-methylbut-2-enyl)pyrazol-3-yl]-2H-pyrrol-5-one (B10) (Step 4)

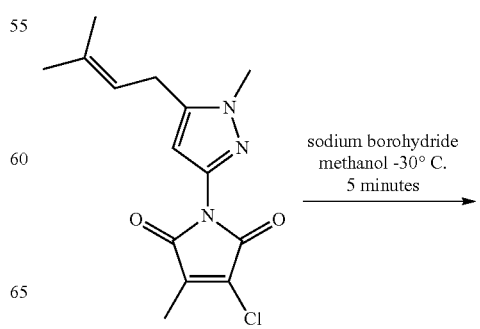

-continued

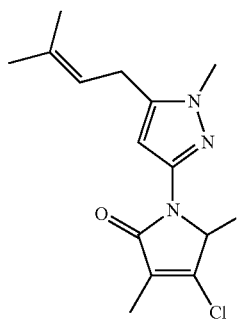 + 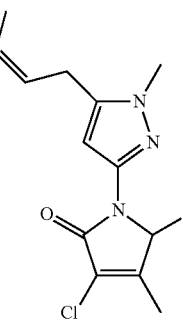

To 3-chloro-4-methyl-1-[1-methyl-5-(3-methylbut-2-enyl)pyrazol-3-yl]pyrrole-2,5-dione (0.374 g, 1.27 mmol) in methanol (10 mL) and tetrahydrofuran (5 mL) at −15° C., was added sodium borohydride (0.054 g, 1.40 mmol). The solution was stirred for two hours. Water and dichloromethane were added and the layers separated. The aqueous layer was extracted three times with dichloromethane. The combined organics washed with water, dried over MgSO$_4$ and concentrated in vacuo to afford a colourless oil. Chromatography on silica gel gave 3-chloro-2-hydroxy-4-methyl-1-[1-methyl-5-(3-methylbut-2-enyl)pyrazol-3-yl]-2H-pyrrol-5-one (0.087 g, 23%) and 4-chloro-2-hydroxy-3-methyl-1-[1-methyl-5-(3-methylbut-2-enyl)pyrazol-3-yl]-2H-pyrrol-5-one (0.171 g, 45%) (B10). 3-chloro-2-hydroxy-4-methyl-1-[1-methyl-5-(3-methylbut-2-enyl)pyrazol-3-yl]-2H-pyrrol-5-one $^1$H NMR (CDCl$_3$) δ 6.45 (s, 1H), 5.87-5.85 (m, 1H), 5.26-5.20 (m, 1H), 4.92 (d, 1H), 3.69 (s, 3H), 3.31-3.25 (m, 2H), 1.95 (s, 3H), 1.79 (s, 3H), 1.71 (s, 3H). 4-chloro-2-hydroxy-3-methyl-1-[1-methyl-5-(3-methylbut-2-enyl)pyrazol-3-yl]-2H-pyrrol-5-one $^1$H NMR (CDCl$_3$) δ 6.49 (s, 1H), 5.86-5.84 (m, 1H), 5.26-5.20 (m, 1H), 4.94 (d, 1H), 3.69 (s, 3H), 3.30-3.27 (m, 2H), 2.14 (s, 3H), 1.76 (s, 3H), 1.71 (s, 3H)

Example 7

Preparation of 1-(5-tert-butyl-1-methyl-pyrazol-3-yl)-2-hydroxy-4-methoxy-3-methyl-2H-pyrrol-5-one (H1)

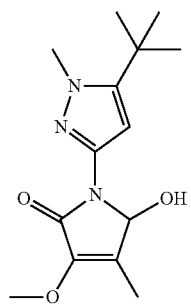 [SMILES: COC1=C(C)C(O)N(c2cc(C(C)(C)C)n(C)n2)C1=O]

Preparation of 2-dimethoxyphosphoryl-2-methoxy-acetic acid (Step 1)

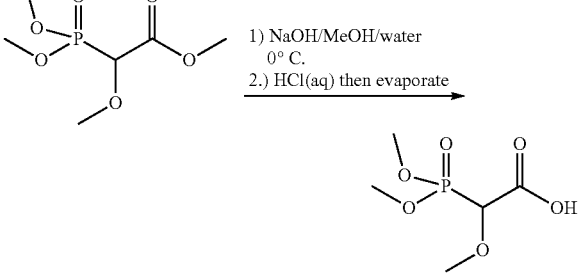

Methyl 2-dimethoxyphosphoryl-2-methoxy-acetate (2 g, 9.43 mM) was dissolved in methanol (15 ml) and THF (5 ml), cooled to 0° C. then 2N NaOH (aq, 5.19 ml, 10.4 mM) was added over 5 mins, and the reaction was stirred at 0° C. After 2 hours the reaction was acidified with 2N HCl(aq) and the solvent was evaporated and the residue azeotroped with 2×20 ml toluene to give tacky white gum. This gum was dissolved in 25 ml DCM and filtered through celite. The filtrate was evaporated to give a colourless gum (1.665 g, 89%).
$^1$H NMR (CDCl$_3$): 3.55s (3H, Methoxy), 3.97d (6H, 2×Me ester), 4.30d (1H, j=19 Hz, CH—P) 10.37 broad s (1H , acid)

Preparation of 2-dimethoxyphosphoryl-2-methoxy-acetyl chloride (Step 2)

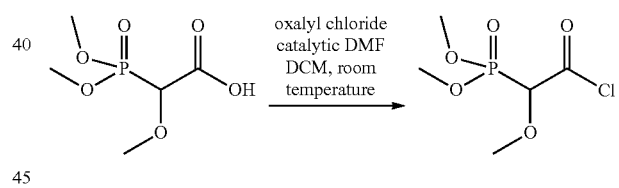

2-dimethoxyphosphoryl-2-methoxy-acetic acid (0.730 g, 3.68 mM) was dissolved in dichloromethane (15 ml) and DMF (0.029 ml) was added, followed by dropwise addition of oxalyl chloride (0.379 ml, 4.42 mM) over 15 minutes. The reaction was stirred at room temperature for 1 hour, then was evaporated to dryness to give a gum, which was reacted in step 3.

Preparation of N-(5-tert-butyl-1-methyl-pyrazol-3-yl)-2-dimethoxyphosphoryl-2-methoxy-acetamide (Step 3)

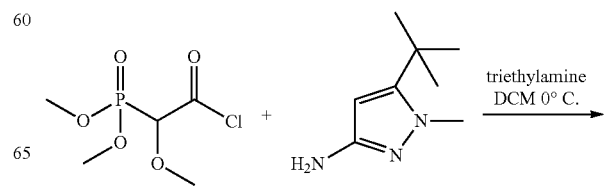

53

-continued

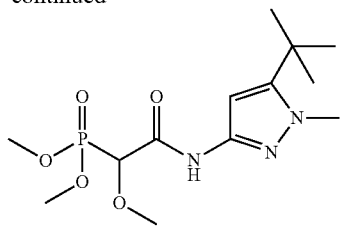

5-tert-butyl-1-methyl-pyrazol-3-amine (0.564 g, 3.68 mM) was dissolved in dichloromethane (8 ml), then triethylamine (0.570 ml, 4.05 mM) was added and the reaction was cooled to 0° C. A solution of 2-dimethoxyphosphoryl-2-methoxy-acetyl chloride (0.797 g, 3.68 mM) in dichloromethane (4 ml) was added dropwise over 15 mins to the reaction. After 90 minutes at 0° C. the reaction was allowed to warm to room temperature, then stirred at room temperature for 1 hour, then water (20 ml) and dichloromethane (20 ml) were added. The mixture was shaken then the layers separated, and the aqueous layer extracted a further 3×20 ml dichloromethane. The combined dichloromethane extracts were dried with $Na_2SO_4$, filtered and evaporated to give a pale yellow waxy solid (1.117 g) which was chromatographed to give a white solid (0.357 g, 29%)

$^1$H NMR (CDCl$_3$) 8.68 (br s, 1H), 6.55 (s, 1H), 4.14 (d, 1H), 3.88 (d, 3H), 3.86 (d, 3H), 3.63 (s, 3H), 1.38 (s, 9H)

(Step 4)

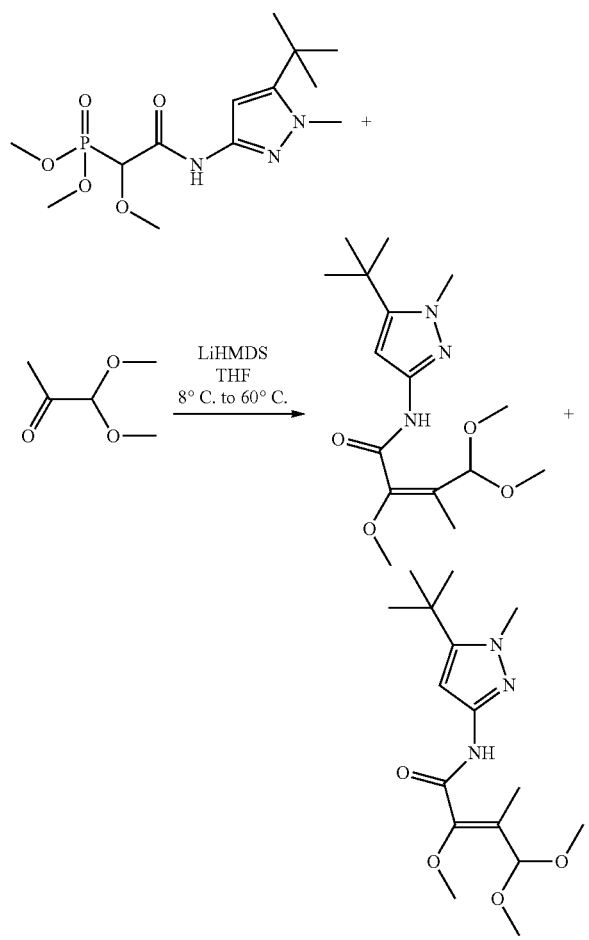

54

N-(5-tert-butyl-1-methyl-pyrazol-3-yl)-2-dimethoxyphosphoryl-2-methoxy-acetamide (338 mg, 1.014 mM) was dissolved in dry THF (2 ml) then was cooled to 8° C. and Lithium bis (trimethylsilyl)amide (LiHMDS, 1M in THF, 1.12 ml, 1.12 mM) was added dropwise over 1 minute to give a yellow solution which was stirred at room temperature for 5 minutes. 1,1-dimethoxypropan-2-one (0.147 ml, 1.217 mM) was added dropwise over 1 minute and the reaction was stirred at room temperature for 25 mins, then was heated to 60° C. for 2 hours and 15 minutes. The reaction was evaporated to remove the bulk of the THF. Water (2 ml), brine (2 ml) and diethyl ether (7 ml) were added, shaken vigorously, and the ether layer was separated. The aqueous layer was extracted a further 3 ×3 ml diethyl ether, the combined ether extracts were dried with $Na_2SO_4$, filtered, and evaporated to give an amber gum (315 mg) This was chromatographed to give 2 products:

1$^{st}$ product was a white crystalline solid for (E)-N-(5-tert-butyl-1-methyl-pyrazol-3-yl)-2,4,4-trimethoxy-3-methyl-but-2-enamide (145 mg, 44%)

$^1$H NMR (CDCl$_3$) 8.69 (br s, 1H), 6.55 (s, 1H), 6.02 (s, 1H), 3.88 (s, 3H), 3.61 (s, 3H), 3.43 (s, 3H), 1.85 (s, 3H), 1.40 (s, 9H).

2$^{nd}$ product was a waxy solid for (Z)—N-(5-tert-butyl-1-methyl-pyrazol-3-yl)-2,4,4-trimethoxy-3-methyl-but-2-enamide (109 mg, 33%)

$^1$H NMR (CDCl$_3$) 8.65 (br s, 1H), 6.61 (s, 1H), 5.17 (s, 1H), 3.87 (s, 3H), 3.61 (s, 3H), 3.40 (s, 3H), 2.07 (s, 3H), 1.40 (s, 9H)

(Step 5)

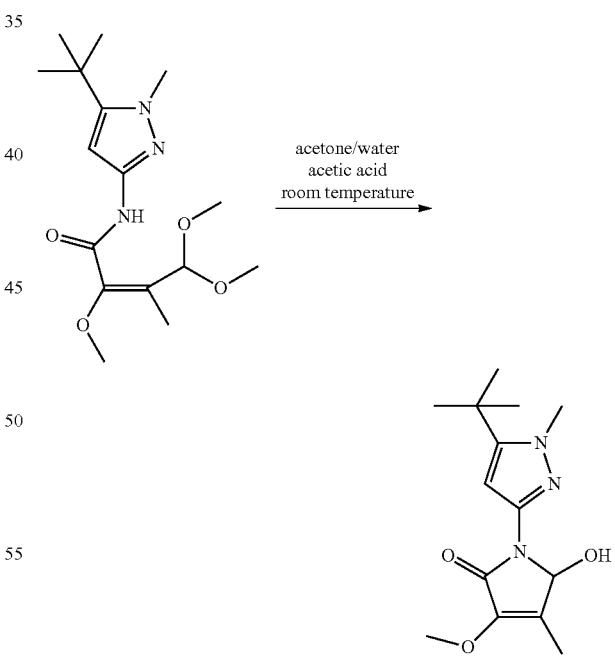

(E)-2,4,4-trimethoxy-3-methyl-N-[4-(trifluoromethyl)-2-pyridyl]but-2-enamide (134 mg, 0.4118 mM) was dissolved in acetone (1.4 ml) and water (0.35 ml), then acetic acid (0.35 ml) was added and the reaction was stirred at room temperature. After 1 hour the reaction was evaporated to give a colourless gum that was combined with the crude product from step 6 and chromatographed.

(Step 6)

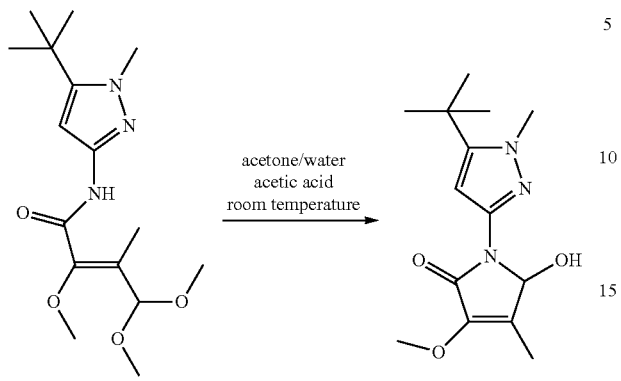

(Z)-2,4,4-trimethoxy-3-methyl-N-[4-(trifluoromethyl)-2-pyridyl]but-2-enamide (60 mg, 0.1844 mM) was dissolved in acetone (0.60 ml) and water (0.15 ml), then acetic acid (0.15 ml) was added and the reaction was stirred at room temperature. After 1 hour the reaction was evaporated to give a colourless gum that was combined with the crude product from step 5 and chromatographed to give a colourless gum (150 mg, 90%). $^1$H NMR (CDCl$_3$) 6.50 (s, 1H), 5.71 (m, 1H), 4.87 (m, 1H), 4.04 (s, 3H), 3.87 (s, 3H), 2.03 (s, 3H), 1.38 (s, 9H)

Table 1 lists compounds of the general formula

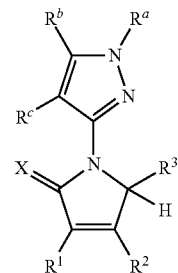

wherein $R^a$, $R^b$, $R^c$, $R^1$, $R^2$ and $R^3$ are as defined in the table. It is noted that, when $R^a$ and $R^b$ or $R^b$ and $R^c$ form a ring structure, the whole of the substituted pyrazole ring is shown in the table for clarity.

These compounds were made by the general methods of Examples 1 to 7.

TABLE 1

Compounds of the Invention

| Compound Number | $R^1$ | $R^2$ | $R^3$ | $R^a$ | $R^b$ | $R^c$ | 1H NMR (measured in CDCl$_3$ unless otherwise indicated) δ |
|---|---|---|---|---|---|---|---|
| A1 | Cl | Me | OH | H | tBu | H | 6.47 (s, 1H); 5.88 (s, 1H); 2.13 (s, 3H); 1.32 (s, 9H) - no OH or NH detected |
| A2 | Cl | Me | OH | H | CF3 | H | 6.58 (br s, 1H); 5.63 (br s, 1H); 3.54 (br s, 2H); 2.07 (s, 3H) |
| A3 | Cl | Me | OH | H | iPr | H | 6.30 (br s, 1H); 5.83 (br s, 1H); 2.97 (hept, 1H); 2.08 (s, 3H); 1.27 (d, 6H) - in CD3OD, no OH or NH detected |
| A4 | Cl | Me | OH | H | cyPr | H | 6.21 (br s, 1H); 5.74 (br s, 1H); 2.04 (s, 3H); 1.74-1.82 (m, 1H); 0.85-0.92 (m, 2H); 0.64-0.70 (m, 2H) - no OH or NH detected |
| A5 | Cl | Me | OH | H | Me | H | 6.32 (br s, 1H); 5.86 (br s, 1H); 2.31 (s, 3H); 2.12 (s, 3H); - in CD3OD, no OH or NH detected |
| A6 | Cl | Me | OH | H | CF2CF3 | H | 6.52 (br s, 1H); 5.64 (br s, 1H); 2.15 (s, 3H) - no OH or NH in CDCl$_3$ + a few drops of CD$_3$OD |
| A7 | Cl | Me | OH | H | C(CH3)(C2H5)2 | H | 6.46 (br s, 1H), 5.92 (s, 1H), 2.13 (s, 3H), 1.66 (m, |

TABLE 1-continued

Compounds of the Invention

| Compound Number | R¹ | R² | R³ | Rᵃ | Rᵇ | Rᶜ | 1H NMR (measured in CDCl₃ unless otherwise indicated) δ |
|---|---|---|---|---|---|---|---|
| B1 | Cl | Me | OH | Me | Me | H | 2H), 1.58 (m, 2H), 1.24 (s, 3H), 0.74 (t, 6H) 6.29 (s, 1H); 5.82 (s, 1H); 3.72 (s, 3H); 2.28 (s, 3H); 2.10 (s, 3H) - in CD3OD, no OH detected |
| B2 | Cl | Me | OH | Me | tBu | H | 6.51 (s, 1H); 5.85 (br s, 1H); 5.07 (br s, 1H); 3.86 (s, 3H); 2.14 (s, 3H); 1.38 (s, 9H) |
| B3 | Cl | Me | OH | Me | CF3 | H | 7.08 (s, 1H); 5.88 (br s, 1H); 4.47 (br s, 1H); 3.92 (s, 3H); 2.14 (s, 3H) |
| B4 | Cl | Me | OH | Me | CF2CF3 | H | 7.13 (s, 1H); 5.90 (br s, 1H); 4.39 (br s, 1H); 3.94 (s, 3H); 2.16 (s, 3H) |
| B5 | Cl | Me | OH | Me | iPr | H | 6.48 (s, 1H), 5.84 (s, 1H), 5.15 (bs, 1H) 3.68 (s, 3H), 2.88 (m, 1H), 2.11 (s, 3H), 1.25 (d, 6H). |
| B6 | Cl | Me | OH | Me | C(CH3)2CH2CH=CH2 | H | 6.52 (s, 1H), 5.84 (m, 1H), 5.59 (m, 1H), 5.07 (m, 1H), 5.03 (m, 1H), 4.95 (d, 1H), 3.88 (s, 3H), 2.44 (d, 2H), 2.14 (s, 3H), 1.37 (s, 6H). |
| B7 | Cl | Me | OH | Me | CH=C(CH3)2 | H | 6.65 (s, 1H), 5.97 (m, 1H), 5.88 (d, 1H), 4.92 (d, 1H), 3.71 (s, 3H), 2.15 (s, 3H), 1.96 (d, 3H), 1.90 (d, 3H) |
| B8 | Cl | Me | OH | Me | I | H | 6.93 (s, 1H), 5.86 (d, 1H), 4.56 (d, 1H), 3.86 (s, 3H), 2.15 (s, 3H). |
| B9 | Cl | Me | OH | Me | Cl | H | 6.72 (s, 1H), 5.88 (d, 1H), 4.55 (d, 1H), 3.78 (s, 3H), 2.15 (s, 3H). |
| B10 | Cl | Me | OH | Me | CH2CH=C(CH3)2 | H | 6.49 (s, 1H), 5.86-5.84 (m, 1H), 5.26-5.20 (m, 1H), 4.94 (d, 1H), 3.69 (s, 3H), 3.30-3.27 (m, 2H), 2.14 (s, 3H), 1.76 (s, 3H), 1.71 (s, 3H) |
| B11 | Cl | Me | OH | Me | CH=CHC(CH3)3 trans | H | 6.75 (s, 1H), 6.34 (d, 1H), 6.10 (d, 1H), 5.86 (d, 1H), 4.91 (d, 1H), 3.76 (s, 3H), 2.15 (s, 3H), 1.13 (s, 9H). |

TABLE 1-continued

Compounds of the Invention

| Compound Number | R¹ | R² | R³ | Rᵃ | Rᵇ | Rᶜ | 1H NMR (measured in CDCl₃ unless otherwise indicated) δ |
|---|---|---|---|---|---|---|---|
| B12 | Cl | Me | OH | Me | 4,4-dimethylcyclohex-1-enyl | H | 6.58 (s, 1H), 5.87 (d, 1H), 5.86-5.82 (m, 1H), 4.93 (d, 1H), 3.76 (s, 3H), 2.33-2.27 (m, 2H), 2.15 (s, 3H), 2.03-1.99 (m, 2H), 1.51 (t, 2H), 0.99 (s, 6H) |
| B13 | Cl | Me | OH | Me | C2F5 | H | 7.13 (s, 1H), 5.90 (br s, 1H), 4.39 (br s, 1H), 3.94 (s, 3H), 2.16 (s, 3H) |
| B14 | Cl | Me | OH | Me | i-Pr | H | 6.48 (s, 1H), 5.84 (s, 1H), 5.15 (br s, 1H), 3.68 (s, 3H), 2.9 (m, 1H), 2.1 (s, 3H), 1.26 (d, 6H) |
| B15 | Cl | Me | OH | Me | H | H | 7.30 (d, 1H), 6.71 (d, 1H), 5.88 (d, 1H), 4.82 (d, 1H), 3.82 (s, 3H), 2.15 (s, 3H) |
| B16 | Cl | Me | OH | Me | I | H | 6.93 (s, 1H), 5.86 (d, 1H), 4.56 (d, 1H), 3.86 (s, 3H), 2.15 (s, 3H) |
| B17 | Cl | Me | OH | Me | 3,3-dimethylbut-1-enyl | H | 6.75 (s, 1H), 6.34 (d, 1H), 6.10 (d, 1H), 5.86 (d, 1H), 4.91 (d, 1H), 3.76 (s, 3H), 2.15 (s, 3H), 1.13 (s, 9H) |
| B18 | Cl | Me | OH | Me | Cl | H | 6.72 (s, 1H), 5.88 (d, 1H), 4.55 (d, 1H), 3.78 (s, 3H), 2.15 (s, 3H) |
| B20 | Cl | Me | OH | Me | 2-methylbut-2-enyl | H | 6.65 (s, 1H), 5.97 (m, 1H), 5.88 (d, 1H), 4.92 (d, 1H), 3.71 (s, 3H), 2.15 (s, 3H), 1.96 (d, 3H), 1.90 (d, 3H) |
| B21 | Cl | Me | OH | Me | buta-1,3-dienyl | H | 6.73 (s, 1 H), 6.09-6.46 (m, 2 H), 5.86 (d, 1 H), 4.93 (d, 1 H), 3.74 (s, 3 H), 2.13 (s, 3 H), 1.91 (dd, 3 H) |
| B22 | Cl | Me | OH | Me | 4-methylpent-3-enyl | H | 6.49 (s, 1H), 5.86-5.84 (m, 1H), 5.26-5.20 (m, 1H), 4.94 (d, 1H), 3.69 (s, 3H), 3.30-3.27 (m, 2H), 2.14 (s, 3H), 1.76 (s, 3H), 1.71 (s, 3H) |

TABLE 1-continued

Compounds of the Invention

| Compound Number | R¹ | R² | R³ | $R^a$ | $R^b$ | $R^c$ | 1H NMR (measured in CDCl₃ unless otherwise indicated) δ |
|---|---|---|---|---|---|---|---|
| B23 | Cl | Me | OH | Me | (structure) | H | 6.52 (s,1H), 5.84 (m, 1H), 5.59 (m, 1H), 5.07 (m, 1H), 5.03 (m, 1H), 4.59 (d, 1H), 3.88 (s, 3H), 2.44 (d, 2H), 2.14 (s, 3H), 1.37 (s, 6H) |
| B24 | Cl | Me | OH | Me | Benzyl | H | 7.35-7.23 (m, 3H), 7.19-7.14 (m, 2H), 6.57 (s, 1H), 5.87 (m, 1H), 4.99 (br. s, 1H), 3.97 (s, 2H), 3.61 (s, 3H), 2.14 (s, 3H) |
| B25 | Cl | Me | OH | Me | (structure) | H | 6.76 (s, 1H), 5.87 (m, 1H), 4.72 (d, 1H), 3.80 (s, 3H), 2.14 (s, 3H), 1.34 (s, 9H) |
| B27 | Cl | Me | OH | Me | (structure) | H | 6.50 (s, 1H), 5.85 (m, 1H), 4.96 (d, 1H), 3.70 (s, 3H), 2.60-2.53 (m, 2H), 2.14 (s, 3H), 1.69-1.61 (m, 1H), 1.59-1.52 (m, 2H), 0.96 (d, 6H) |
| B28 | Cl | Et | OH | Me | H | H | 7.31 (d, 1H), 6.41 (d, 1H), 5.99 (s, 1H), 3.85 (s, 3H), 2.86 (br s, 1H), 2.70-2.48 (m, 2H), 1.23 (t, 3H) |
| B29 | Cl | Me | OH | Me | (structure) | H | 6.77 (s, 1H), 5.87 (m, 1H), 4.73 (d, 1H), 3.81 (s, 3H), 2.87-2.79 (m, 1H), 2.14 (s, 3H), 1.29 (d, 6H) |
| B30 | Cl | Me | OH | Me | (structure) | H | 6.78 (m, 1H), 5.88 (m, 1H), 4.72 (d, 1H), 3.82 (s, 3H), 2.36 (m, 2H), 2.14 (s, 3H), 2.00-1.90 (m, 1H), 1.05 (m, 6H) |
| B31 | Cl | Me | OH | Me | (structure) | H | 6.59 (s, 1H), 5.89-5.85 (m, 1H), 5.00 (t, 1H, OH), 3.90 (s, 3H, NMe), 3.08 (s, 3H, MeO), 2.14 (s, 3H, Me), 1.97-1.78 (m, 2H, |

TABLE 1-continued

Compounds of the Invention

| Compound Number | R¹ | R² | R³ | $R^a$ | $R^b$ | $R^c$ | 1H NMR (measured in CDCl₃ unless otherwise indicated) δ |
|---|---|---|---|---|---|---|---|
| | | | | | | | CH2CH3), 1.52 (s, 3H, Me), 0.93-0.81 (m, 3H, CH3CH2). |
| B32 | Cl | Me | OH | Me | (structure) | H | 6.57 (s, 1H), 5.88-5.84 (m, 1H), 4.97 (d, 1H), 3.92 (s, 3H), 3.35-3.26 (m, 1H), 3.18-3.08 (m, 1H), 2.14 (s, 3H), 2.00-1.80 (m, 2H), 1.53-1.51 (m, 3H), 1.17 (t, 3H), 0.88-0.79 (m, 3H). |
| B33 | Cl | Me | OH | Me | (structure) | H | 6.50 (s, 1H), 5.85 (m, 1H), 4.97 (d, 1H), 3.72 (s, 3H), 2.74-2.66 (m, 1H), 2.14 (s, 3H), 1.73-1.57 (m, 2H), 1.27-1.22 (m, 3H), 0.96-0.88 (m, 3H) |
| B34 | Cl | Me | OH | Me | (structure) | H | mixture of diastereoisomers (~1:1 ratio) 6.60 (s, 0.5H), 6.59 (s, 0.5H), 5.88 (pseudo t, 1H), 4.97 (br d, 0.5H), 4.88 (br d, 0.5H), 4.06 (pseudo d, 1H), 3.81 (pseudo d, 3H), 3.46-3.36 (m, 1H), 3.30-3.21 (m, 1H), 2.15 (s, 3H), 1.17 (t, 3H), 0.96 (s, 9H) |
| B35 | Cl | Me | OH | Me | (structure) | H | 6.77 (s, 1H), 5.87 (m, 1H), 4.70 (d, 1H), 3.82 (s, 3H), 2.14 (s, 3H), 2.12 (s, 3H) |
| B36 | Cl | Me | OH | Me | SMe | H | 6.71 (s, 1H), 5.87 (m, 1H), 4.74 (m, 1H), 3.78 (s, 3H), 2.47 (s, 3H), 2.15 (s, 3H) |
| B37 | Cl | Me | OH | Me | (structure) | H | mixture of diastereoisomers (~1:1 ratio) 6.73 (s, 1H), 5.88 (pseudo t, 1H), 5.19 (d, 1H), 4.86 (br s, 0.5H), 4.78 (br s, 0.5H), 3.81 (s, 3H), 2.15 (s, 3H), 1.06 (s, 9H) |

TABLE 1-continued

Compounds of the Invention

| Compound Number | R¹ | R² | R³ | Rᵃ | Rᵇ | Rᶜ | 1H NMR (measured in CDCl₃ unless otherwise indicated) δ |
|---|---|---|---|---|---|---|---|
| B38 | Cl | Me | OH | Me | SO2Me | H | 7.32 (s, 1H), 5.91 (m, 1H), 4.30 (d, 1H), 4.11 (s, 3H), 3.21 (s, 3H), 2.17 (s, 3H) |
| B39 | Cl | Me | OH | Me | –CF₂CH(CH₃)– (CHF₂CH(Me)) | H | 6.79 (s, 1H), 5.87 (m, 1H), 4.77 (d, 0.5H), 4.68 (d, 0.5H), 3.79 (s, 3H), 3.59-3.50 (m, 1H), 2.15 (s, 3H), 1.58-1.53 (m, 3H) |
| B40 | Cl | Me | OH | Me | CH(Me)C(Me)₂F (tBu-CHF) | H | mixture of diastereoisomers (~1:1 ratio) 6.49 (br s, 1H), 5.88 (br s, 1H), 4.92 (br s, 1H), 3.92 (pseudo d, 3H), 2.14 (s, 3H), 1.71 (d, 1.5H), 1.65 (d, 1.5H), 1.03 (pseudo d, 9H) |
| B41 | Cl | Me | OH | Me | CH(CH3)(Ph) | H | 7.32-7.26 (m, 2H), 7.24-7.19 (m, 1H), 7.16-7.11 (m, 2H), 6.76 (s, 1H), 5.86 (d, 1H), 5.02 (d, 1H), 4.04-3.98 (m, 1H), 3.44 (s, 3H), 2.13 (s, 3H), 1.62 (d, 3H) |
| B42 | Cl | Me | OH | Me | C(Me)₂CN | H | 6.65 (s, 1H), 5.87 (s, 1H), 4.66 (br s, 1H), 3.99 (s, 3H), 2.14 (s, 3H), 1.79 (s, 3H), 1.78 (s, 3H) |
| B43 | Cl | Me | OH | Me | CH(Me)CH=CHMe | H | 6.75 (s, 1H), 6.22-6.17 (m, 1H), 6.03-5.95 (m, 1H), 5.89 (m, 1H), 4.96 (m, 1H), 3.73 (s, 3H), 2.15 (s, 3H), 1.91 (d, 3H) |
| B45 | Cl | Me | OH | Me | C(=CH₂)Me | H | 6.67 (s, 1H), 5.88 (d, 1H), 5.38 (s, 1H), 5.17 (s, 1H), 4.87 (d, 1H), 3.82 (s, 3H), 2.15 (s, 3H), 2.10 (s, 3H) |
| B46 | Cl | Me | OH | Me | S(O)Me | H | 7.06 (s, 1H), 5.91 (m, 1H), 4.43 (d, 1H), 4.07 (s, 3H), 3.03 (s, 3H), 2.17 (s, 3H) |

TABLE 1-continued

Compounds of the Invention

| Compound Number | R¹ | R² | R³ | Rᵃ | Rᵇ | Rᶜ | 1H NMR (measured in CDCl₃ unless otherwise indicated) δ |
|---|---|---|---|---|---|---|---|
| B48 | Cl | Me | OH | Me | (2-methylbut-2-en-2-yl) | H | 6.46 (s, 1H), 5.88 (d, 1H), 5.11-5.05 (m, 1H), 3.58 (s, 3H), 2.14 (s, 3H), 1.88 (s, 3H), 1.83 (s, 3H), 1.56 (s, 3H) |
| B49 | Cl | Me | OH | Me | (1-ethoxybut-1-en-3-yl) | H | 7.01 (s, 1H), 6.34 (d, 1H), 5.86 (m, 1H), 5.15 (d, 1H), 5.00 (d, 1H), 4.04 (q, 2H), 3.72 (s, 3H), 2.14 (s, 3H), 1.37 (t, 3H) |
| C1 | Cl | Me | OH | Et | CF3 | H | 7.08 (s, 1H); 5.92 (br d, 1H); 4.47 (d, 1H); 4.21 (q, 2H); 2.15 (s, 3H); 1.47 (t, 3H) |
| C2 | Cl | Me | OH | Et | tBu | H | 6.47 (s, 1H); 5.88 (d, 1H); 5.08 (d, 1H); 4.16 (q, 2H); 2.15 (s, 3H); 1.42 (t, 3H); 1.37 (s, 9H) |
| C3 | Cl | Me | OH | | (1-ethyl-5,5-dimethyl-4,5,6-tetrahydrocyclopenta[c]pyrazol-3-yl) | | 5.83 (br d, 1H); 5.28 (d, 1H); 3.96 (q, 2H); 2.96-2.79 (m, 2H); 2.36-2.25 (m, 2H); 2.14 (s, 3H); 1.41 (t, 3H); 1.35 (s, 3H); 1.34 (s, 3H) |
| C4 | Cl | Me | OH | iPr | CF3 | H | 7.07 (s, 1H); 5.93 (br d, 1H); 4.61 (hept, 1H); 4.51 (d, 1H); 2.16 (s, 3); 1.51 (d, 3H); 1.48 (d, 3H) |
| C5 | Cl | Me | OH | CH2CF3 | CF3 | H | 7.29 (s, 1H); 5.96 (d, 1H); 4.72 (q, 2H); 4.26 (d, 1H); 2.18 (s, 3H) |
| C6 | Cl | Me | OH | Et | CF3 | H | 7.08 (s, 1H), 5.92 (br d, 1H), 4.47 (d, 1H), 4.21 (q, 2H), 2.15 (s, 3H), 1.47 (t, 3H) |
| C7 | Cl | Me | OH | i-Pr | CF3 | H | 7.07 (s, 1H), 5.93 (br d, 1H), 4.61 (hept, 1H), 4.51 (d, 1H), 2.16 (s, 3H), 1.51 (d, 3H), 1.48 (d, 3H) |
| C8 | Cl | Me | OH | Et | tert-Bu | H | 6.47 (s, 1H), 5.88 (d, 1H), 5.08 (d, 1H), 4.16 (q, 2H), 2.15 (s, 3H), 1.42 (t, 3H), 1.37 (s, 9H) |
| C9 | Cl | Me | OH | CH2CF3 | CF3 | H | 7.29 (s, 1H), 5.96 (d, 1H), 4.72 (q, 2H), 4.26 (d, 1H), 2.18 (s, 3H) |

TABLE 1-continued

Compounds of the Invention

| Compound Number | R¹ | R² | R³ | Rᵃ | Rᵇ | Rᶜ | 1H NMR (measured in CDCl₃ unless otherwise indicated) δ |
|---|---|---|---|---|---|---|---|
| C10 | Cl | Me | OH | (ethyl-substituted dihydropyrrolopyrazole group) | | | mixture of diastereoiosmers (~1:1 ratio); 6.48 (s, 1H), 5.88-5.85 (m, 1H), 5.22-5.19 (m, 1H), 4.10-4.02 (m, 1H), 4.00-3.92 (m, 1H), 3.17-3.08 (m, 1H), 2.78-2.65 (m, 1H), 2.23-2.14 (m, 1H), 2.14 (s, 3H), 1.78-1.52 (m, 2H), 1.14 (dt, 3H) |
| C11 | Cl | Me | OH | CH2CF3 | CN | H | DMSO d6: 7.44 (s, 1H), 6.89 (d, 1H), 5.93 (d, 1H), 5.36 (m, 2H), 2.05 (s, 3H) |
| C12 | Cl | Me | OH | CHF2 | Me | H | 7.06 (t, 1H), 6.73 (s, 1H), 5.89 (d, 1H), 4.43 (d, 1H), 2.47 (s, 3H), 2.16 (s, 3H) |
| C13 | Cl | Me | OH | CF3 | Me | H | 6.79 (s, 1H), 5.97 (d, 1H), 4.52 (br d, 1H), 2.46 (s, 3H), 2.16 (s, 3H) |
| D1 | Cl | Me | OH | Me | tBu | CN | 5.84 (s, 1H), 3.96 (s, 3H), 2.14 (s, 3H), 1.57 (s, 9H). |
| D2 | Cl | Me | OH | Me | t-Bu | CN | 5.8 (s, 1H), 3.96 (s, 3H), 3.48 (br s, 1H), 2.14 (s, 3H), 1.57 (s, 9H) |
| D3 | Cl | Me | OH | Me | t-Bu | Cl | 5.63 (s, 3H), 3.97 (s, 3H), 2.15 (s, 3H), 1.52s (s, 9H) 5.53 (s, 3 H), 3.98 (s, 3H), 1.95 (s, 3H), 1.52s (s, 9 H) |
| D4 | Cl | Me | OH | Me | (ClCH2-C(Me)2- group) | Cl | 5.65 (s, 1H), 4.02 (d, 3H), 3.83 (dq, 2H), 2.13 (d, 3H), 1.65 (s, 6H) |
| D5 | Cl | Me | OH | Me | SMe | CN | [DMSOd6] 7.92(d, 1H), 5.83 (d, 1H), 3.71 (s, 3H), 2.55 (s, 3H), 2.11 (s, 3H) |
| D6 | Cl | Me | OH | CH2CF3 | Me | CN | 5.92 (d, 1H), 4.62 (m, 2H), 3.94 (d, 1H), 2.5 (s, 3H), 2.15 (s, 3H) |
| E1 | Cl | Me | OH | (dimethyl-substituted dihydrocyclopenta-pyrazole with N-ethyl group) | | | 5.83 (br d, 1H), 5.28 (d, 1H), 3.96 (q, 2H), 2.96-2.79 (m, 2H), 2.36-2.25 (m, 2H), 2.14 (s, 3H), 1.41 (t, 3H), 1.35 (s, 3H), 1.34 (s, 3H) |

TABLE 1-continued

Compounds of the Invention

| Compound Number | R¹ | R² | R³ | Rᵃ | Rᵇ | Rᶜ | 1H NMR (measured in CDCl₃ unless otherwise indicated) δ |
|---|---|---|---|---|---|---|---|
| E2 | Cl | Me | OH | | *7,7-dimethyl-1-ethyl-4,5,6,7-tetrahydro-1H-cyclopenta[c]pyrazol-3-yl* | | 5.82 (br s, 1H), 5.18 (br s, 1H), 3.68 (s, 3H), 2.95-2.78 (m, 2H), 2.29 (dt, 2H), 2.13 (s, 3H), 1.33 (s, 3H), 1.32 (s, 3H) |
| E3 | Cl | Me | OH | | *8,8-dimethyl-1-methyl cycloheptapyrazolyl* | | 5.63 (br s, 1H), 4.24 (br s, 1H), 3.83 (s, 3H), 2.47-2.33 (m, 2H), 2.13 (s, 3H), 1.88-1.75 (m, 4H), 1.70-1.63 (m, 2H), 1.48 (s, 3H), 1.47 (s, 3H) |
| E4 | Cl | Me | OH | | *bicyclic pyrazole* | | 5.81 (d, 1H), 5.22 (br s, 1H), 3.83 (br d, 1H), 3.68 (s, 3H), 3.32 (br s, 1H), 2.12 (s, 3H), 2.03-1.86 (m, 6H), 1.61 (d, 1H), 1.38-1.08 (m, 2H) |
| E5 | Cl | Me | OH | | *7,7-dimethyl-1-methyl-4,5,6,7-tetrahydroindazolyl* | | 5.72 (br s, 1H), 5.06 (br s, 1H), 3.79 (s, 3H), 2.61-2.42 (m, 2H), 2.12 (s, 3H), 1.71-1.59 (m, 4H), 1.43 (s, 3H), 1.42 (s, 3H) |
| F1 | Cl | Me | —OC(O)OCH₂CH(CH₃)₂ | Me | tBu | H | 6.91 (s, 1H), 6.46 (s, 1H), 4.05 (m, 2H), 3.83 (s, 3H), 2.10 (s, 3H), 2.03 (septet, 1H), 1.36 (s, 9H), 0.96 (d, 6H) |
| F2 | Cl | Me | —OC(O)OC₆H₅ | Me | tBu | H | 7.42 (m, 2H), 7.25 (m, 3H), 6.98 (s, 1H), 6.50 (s, 1H), 3.88 (s, 3H), 2.16 (s, 3H), 1.39 (s, 9H) |
| F3 | Cl | Me | *phenyl carbonate of tBu* | Me | t-Bu | H | 7.42 (m, 2H), 7.25 (m, 3H), 6.98 (s, 1H), 6.50 (s, 1H), 3.88 (s, 3H), 2.16 (s, 3H), 1.39 (s, 9H) |
| F4 | Cl | Me | *isobutyl carbonate of tBu* | Me | t-Bu | H | 6.91 (s, 1H), 6.46 (s, 1H), 4.05 (m, 2H), 3.83 (s, 3H), 2.10 (s, 3H), 2.03 (sept, 1H), 1.36 (s, 9H), 0.96 (d, 6H) |

TABLE 1-continued

Compounds of the Invention

| Compound Number | R¹ | R² | R³ | Rᵃ | Rᵇ | Rᶜ | 1H NMR (measured in CDCl₃ unless otherwise indicated) δ |
|---|---|---|---|---|---|---|---|
| G1 | Cl | Me | OH | | (4-methyl-5,6-dihydro-4H-pyrrolo[1,2-b]pyrazol-2-yl) | | mixture of diastereoisomers (~1:1 ratio): 6.48 (s, 1H); 5.87 (br s, 1H); 4.95 (br s, 1H); 4.18-4.09 (m, 1H); 4.05-3.95 (m, 1H); 3.34-3.24 (m, 1H); 2.80-2.68 (m, 1H); 2.19-2.09 (m, 1H); 2.15 (s, 3H); 1.33 (d, 1.5 H); 1.32 (d, 1.5 H) |
| G2 | Cl | Me | OH | | (4,4-dimethyl-5,6-dihydro-4H-pyrrolo[1,2-b]pyrazol-2-yl) | | 6.41 (s, 1H); 5.87 (d, 1H); 4.91 (d, 1H); 4.16-4.06 (m, 2H); 2.38 (dd, 2); 2.14 (s, 3H); 1.36 (s, 3H); 1.35 (s, 3H) |
| G3 | Cl | Me | OH | | (4-ethyl-5,6-dihydro-4H-pyrrolo[1,2-b]pyrazol-2-yl) | | mixture of diastereoiosmers (~1:1 ratio): 6.48 (s, 1H); 5.88-5.85 (m, 1H); 5.22-5.19 (m, 1H); 4.10-4.02 (m, 1H); 4.00-3.92 (m, 1H); 3.17-3.08 (m, 1H); 2.78-2.65 (m, 1H); 2.23-2.14 (m, 1H); 2.14 (s, 3H); 1.78-1.52 (m, 2H); 1.14 (dt, 3H) |
| G4 | Cl | Me | OH | | (4,4-dimethyl-4,5,6,7-tetrahydropyrazolo[1,5-a]pyridin-2-yl) | | 6.51 (s, 1H); 5.83 (br s, 1H); 5.12 (br s, 1H); 3.95 (pseudo t, 1H); 2.14 (s, 3H); 2.10-2.02 (m, 2H); 1.71-1.67 (m, 2H); 1.32 (s, 3H); 1.31 (s, 3H) |
| G5 | Cl | Me | OH | | (4-ethyl-4,5,6,7-tetrahydropyrazolo[1,5-a]pyridin-2-yl) | | mixture of diastereoisomers (~1:1 ratio): 6.52 (s, 1H); 5.86 (br d, 1H); 5.9 (br s, 0.5H (A)); 5.02, (br s, 0.5H (B)); 4.10-4.00 (m, 1H); 3.97-3.86 (m, 1H); 2.80-2.69 (m, 1H); 2.19-2.09 (m, 1H); 2.14 (s, 3H); 2.08-1.99 (m, 1H); 1.98-1.83 (m, 1H); 1.60-1.40 (m, 3H); 1.00 (t, 1.5H (B)), 0.99 (t, 1.5H (A)) |

TABLE 1-continued

Compounds of the Invention

| Compound Number | R¹ | R² | R³ | Rᵃ | Rᵇ | Rᶜ | 1H NMR (measured in CDCl₃ unless otherwise indicated) δ |
|---|---|---|---|---|---|---|---|
| G6 | Cl | Me | OH | | | | mixture of diastereoisomers (~1:1 ratio): 6.48 (s, 1H), 5.87 (br s, 1H), 4.95 (br s, 1H), 4.18-4.09 (m, 1H), 4.05-3.95 (m, 1H), 3.34-3.24 (m, 1H), 2.80-2.68 (m, 1H), 2.19-2.09 (m, 1H), 2.15 (s, 3H), 1.33 (d, 1.5 H), 1.32 (d, 1.5 H) |
| G7 | Cl | Me | OH | | | | mixture of diastereoisomers (~1:1 ratio): 6.52 (s, 1H), 5.86 (br d, 1H), 5.9 (br s, 0.5H), 5.02, (br s, 0.5H), 4.10-4.00 (m, 1H), 3.97-3.86 (m, 1H), 2.80-2.69 (m, 1H), 2.19-2.09 (m, 1H), 2.14 (s, 3H), 2.08-1.99 (m, 1H), 1.98-1.83 (m, 1H), 1.60-1.40 (m, 3H), 1.00 (t, 1.5H), 0.99 (t, 1.5H) |
| G8 | Cl | Me | OH | | | | 6.51 (s, 1H), 5.87 (d, 1H), 4.91 (d, 1H), 4.16-4.06 (m, 2H), 2.36 (dd, 2H), 2.14 (s, 3H), 1.36 (s, 3H), 1.35 (s, 3H) |
| G9 | Cl | Me | OH | | | | 6.51 (s, 1H), 5.83 (br s, 1H), 5.12 (br s, 1H), 3.95 (pseudo t, 1H), 2.14 (s, 3H), 2.10-2.02 (m, 2H), 1.71-1.67 (m, 2H), 1.32 (s, 3H), 1.31 (s, 3H) |
| G10 | Cl | Me | OH | | | | 6.59 (s, 1H), 5.86 (d, 1H), 4.87 (d, 1H), 4.27-4.18 (m, 2H), 3.17-3.10 (m, 2H), 2.15 (s, 3H), 1.70 (s, 3H), 1.69 (s, 3H) |
| G11 | Cl | Me | OH | | | | 6.70 (s, 1H), 5.87 (br s, 1H), 4.62 (br s, 1H), 4.58 (t, 2H), 3.60-3.46 (m, 2H), 2.14 (s, 3H), 1.76 (s, 3H), 1.75 (s, 3H) |

TABLE 1-continued

Compounds of the Invention

| Compound Number | R$^1$ | R$^2$ | R$^3$ | R$^a$ | R$^b$ | R$^c$ | 1H NMR (measured in CDCl$_3$ unless otherwise indicated) δ |
|---|---|---|---|---|---|---|---|
| G12 | Cl | Me | OH | (structure: pyrazoline fused with S=O ring, gem-dimethyl) | | | mixture of diastereoisomers (~1:2 ratio) 6.62 (s, 1H), 5.90 (s, 0.34H), 5.87 (s, 0.66H), 5.02 (br s, 1H), 4.61-4.49 (m, 1H), 4.30-4.20 (m, 1H), 3.40 (br t, 0.34H), 3.36 (s, 0.66H), 3.29-3.17 (m, 1H), 2.15 (s, 3H), 1.74 (s, 3H), 1.52 (s, 3H) |
| H1 | OMe | Me | OH | Me | tBu | H | 6.50 (s, 1H), 5.71 (m, 1H), 4.87 (m, 1H), 4.04 (s, 3H), 3.87 (s, 3H), 2.03 (s, 3H), 1.38 (s, 9H) |
| H2 | OMe | Me | OH | Me | t-Bu | H | 6.50 (s, 1H), 5.71 (m, 1H), 4.87 (m, 1H), 4.04 (s, 3H), 3.86 (s, 3H), 2.03 (s, 3H), 1.38 (s, 9H) |
| H3 | OMe | Me | OH | Me | t-Bu | CN | 5.66 (d, 1H), 4.04 (s, 3H), 3.97 (s, 3H), 3.15 (br s, 1H), 2.0 (s, 3H), 1.54 (s, 9H) |
| H4 | OMe | Me | OH | Me | CF3 | H | 7.11 (s, 1H), 5.75 (d, 1H), 4.29 (d, 1H), 4.05 (s, 3H), 3.92 (s, 3H), 2.05 (s, 3H) |
| I1 | Br | Me | OH | H | tBu | H | 6.33 (s, 1H); 5.86 (s, 1H); 2.10 (s, 3H); 1.33 (s, 9H) - in CD3OD, no OH or NH detected |
| J1 | Br | Me | OH | Me | tBu | H | 6.51 (s, 1H); 5.86 (br d, 1H); 5.18 (br d, 1H); 3.84 (s, 3H); 2.12 (s, 3H); 1.38 (s, 9H) |
| J2 | Br | Me | OH | Me | t-Bu | H | 6.51 (s, 1H); 5.86 (br d, 1H); 5.18 (br d, 1H); 3.84 (s, 3H), 2.12 (s, 3H), 1.38 (s, 9H) |
| J3 | Br | Me | OH | Me | (structure: CH2-CH=C(Me)2 prenyl group) | H | 6.49 (s, 1H), 5.85 (d, 1H), 5.24 (m, 1H), 4.92 (d, 1H), 3.69 (s, 3H), 3.28 (m, 2H), 2.13 (s, 3H), 1.76 (s, 3H), 1.71 (s, 3H) |
| J4 | Br | Me | OH | Me | CF3 | H | 7.11 (s, 1H), 5.90 (d, 1H), 4.39 (d, 1H), 3.92 (s, 3H), 2.15 (s, 3H) |
| L1 | Br | Me | OH | Me | t-Bu | CN | 5.8 (d, 1H), 3.96 (s, 3H), 3.81 (d, 1H), 2.13 (s, 3H), 1.55 (s, 9H) |

TABLE 1-continued

Compounds of the Invention

| Compound Number | R¹ | R² | R³ | Rᵃ | Rᵇ | Rᶜ | 1H NMR (measured in CDCl₃ unless otherwise indicated) δ |
|---|---|---|---|---|---|---|---|
| L2 | Br | Et | OH | Me | t-Bu | CN | 5.9 (d, 1H), 3.97 (s, 3H), 3.52 (d, 1H), 2.56 (m, 2H), 1.56 (s, 9H) 1.23 (t, 3H) |
| L3 | Br | n-Pr | OC(O)Et | Me | t-Bu | CN | 6.98 (s, 1H), 3.95 (s, 3H), 2.43 (m, 4H), 1.56 (m, 2H), 1.53 (s, 9H), 1.12 (t, 3H), 1.0 (t, 3H) |
| L4 | Br | n-Pr | OH | Me | t-Bu | CN | 5.86 (d, 1H), 3.96 (s, 3H), 3.63 (d, 1H), 2.5 (m, 2H), 1.7 (m, 2H), 1.54 (s, 9H), 1.0 (t, 3H). |
| M1 | Br | Me | OH | (pyrazole-fused pyrrolidine, gem-dimethyl) | | | 6.41 (s, 1H), 5.870 (br s, 1H), 4.98 (br s, 1H), 4.06 (t, 2H), 2.39 (t, 2H), 2.12 (s, 3H), 1.33 (s, 3H), 1.32 (s, 3H) |
| M2 | Br | Me | OH | (pyrazole-fused piperidine, gem-dimethyl) | | | 6.51 (s, 1H), 5.86 (s, 1H), 5.37 (br s, 1H), 3.99-3.86 (m, 2H), 2.12 (s, 3H), 2.08-2.02 (m, 2H), 1.71-1.66 (m, 2H), 1.32 (s, 3H), 1.31 (s, 3H) |
| M3 | Br | Me | OH | (pyrazole-fused thiomorpholine, gem-dimethyl) | | | 6.88 (s, 1H), 5.13 (br s, 1H), 4.92 (br d, 1H), 4.22-4.10 (m, 2H), 3.12 (t, 2H), 2.14 (s, 3H), 1.68 (s, 3H), 1.67 (s, 3H) |
| M4 | Br | Me | OH | (pyrazole-fused thiomorpholine S,S-dioxide, gem-dimethyl) | | | 6.72 (br s, 1H), 5.86 (br s, 1H), 4.60-4.52 (m, 3H), 3.60-3.48 (m, 2H), 2.14 (s, 3H), 1.78 (s, 3H), 1.77 (s, 3H) |
| M5 | Br | Me | OH | (pyrazole-fused thiomorpholine S-oxide, gem-dimethyl) | | | mixture of diastereoisomers (~1:1 ratio) 6.73 (br s, 1H), 5.90 (br s, 0.5H), 5.87 (br s, 0.5H), 5.08 (br s, 1H), 4.61-4.45 (m, 1H), 4.30-4.18 (m, 1H), 3.40-3.17 (m, 2H), 2.16 (s, 3H), 1.72 (s, 3H), 1.51 (s, 3H) |
| N1 | Br | Me | OH | (N-methyl pyrazole-fused cyclopentane, gem-dimethyl) | | | 6.81 (d, 1H), 5.20 (br d, 1H), 3.68 (s, 3H), 2.94-2.80 (m, 2H), 2.28 (t, 2H), 2.13 (s, 3H), 1.32 (s, 3H), 1.31 (s, 3H) |

TABLE 1-continued

Compounds of the Invention

| Compound Number | $R^1$ | $R^2$ | $R^3$ | $R^a$ | $R^b$ | $R^c$ | 1H NMR (measured in CDCl$_3$ unless otherwise indicated) δ |
|---|---|---|---|---|---|---|---|
| O1 | Br | OMe | OH | Me | t-Bu | Br | 5.68 (d, 1H); 4.27 (s, 3H); 3.99 (s, 3H); 3.38 (d, 1H); 1.53 (s, 9H) |
| R1 | OMe | Me | OH | (pyrazole-fused ring structure) | | | 6.39 (s, 1H), 5.71 (m, 1H), 5.00 (m, 1H), 4.07-4.00 (m, 2H), 4.02 (s, 3H), 2.37-2.30 (m, 2H), 2.01 (s, 3H), 1.32 (app. d, 6H) |
| R2 | OMe | Me | OH | (pyrazole-fused ring structure) | | | 6.51 (s, 1H), 5.70 (s, 1H), 4.96 (br s, 1H), 4.04 (s, 3H), 3.98-3.92 (m, 2H), 2.09-2.04 (m, 2H), 2.03 (s, 3H), 1.70-1.65 (m, 2H), 1.32 (br s, 6H) |
| T1 | OMe | OMe | OH | Me | t-Bu | H | 6.45 (s, 1H), 5.79 (br s, 1H), 5.12 (br s, 1H), 4.12 (s, 3H), 3.92 (s, 3H), 3.84 (s, 3H), 1.38 (s, 9H) |
| T2 | OMe | OMe | OH | Me | CF3 | H | 6.41 (s, 1H), 5.42 (d, 1H), 4.13 (s, 3H), 3.89 (s, 3H), 3.77 (s, 3H) (no OH peak) |
| W1 | OMe | OMe | OH | (pyrazole-fused ring structure) | | | 6.39 (s, 1H), 5.80 (s, 1H), 5.04 (br s, 1H), 4.11 (s, 3H), 4.05 (t, 2H), 3.93 (s, 3H), 2.37 (t, 2H), 1.32 (s, 3H), 1.31 (s, 3H) |
| W2 | OMe | OMe | OH | (pyrazole-fused ring structure) | | | 6.48 (s, 1H), 5.81 (s, 1H), 5.84 (br s, 1H), 4.12 (s, 3H), 3.98-3.87 (m, 5H), 2.07-2.01 (m, 2H), 1.69-1.64 (m, 2H), 1.32 (s, 3H), 1.31 (s, 3H) |

Example 8

Herbicidal Action

Example 8a

Pre-emergence Herbicidal Activity

Seeds of a variety of test species were sown in standard soil in pots. After cultivation for one day (pre-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Table 2.

TABLE 2

| | | Application pre-emergence | | | | | |
|---|---|---|---|---|---|---|---|
| Compound Number | Rate (g/ha) | ABUTH | AMARE | SETFA | ALOMY | ECHCG | ZEAMX |
| A1 | 1000 | 5 | 5 | 5 | 3 | 5 | 2 |
| A2 | 1000 | 5 | 5 | 0 | 0 | 3 | 2 |
| A3 | 1000 | 5 | 5 | 5 | 3 | 5 | 1 |
| A4 | 1000 | 5 | 5 | 5 | 4 | 5 | 2 |
| A5 | 1000 | 5 | 5 | 4 | 3 | 5 | 2 |
| A6 | 1000 | 5 | 5 | 4 | 3 | 4 | 1 |
| A7 | 1000 | 5 | 5 | 5 | 3 | 5 | 3 |
| B1 | 1000 | 5 | 5 | 4 | 3 | 4 | 3 |
| B2 | 1000 | 5 | 5 | 5 | 4 | 5 | 2 |
| B3 | 1000 | 5 | 4 | 4 | 4 | 5 | 2 |
| B4 | 1000 | 5 | 5 | 5 | 4 | 5 | 2 |
| B5 | 1000 | 5 | 5 | 4 | 3 | 5 | 2 |
| B6 | 1000 | 5 | 5 | 5 | 4 | 4 | 4 |
| B7 | 1000 | 4 | 4 | 4 | 2 | 4 | 2 |
| B8 | 1000 | 4 | 5 | 5 | 4 | 4 | 3 |
| B9 | 1000 | 4 | 5 | 5 | 3 | 4 | 2 |
| B10 | 1000 | 0 | — | 0 | 0 | 0 | 0 |
| B11 | 1000 | 2 | 4 | 3 | 2 | 4 | 2 |
| B12 | 1000 | 4 | 1 | 2 | 0 | 0 | 1 |
| B13 | 1,000 | 5 | 5 | 5 | 4 | 5 | 2 |
| B14 | 1,000 | 5 | 5 | 4 | 3 | 5 | 2 |
| B15 | 1,000 | 4 | 5 | 4 | 3 | 4 | 2 |
| B16 | 1,000 | 4 | 5 | 5 | 4 | 4 | 3 |
| B17 | 1,000 | 2 | 4 | 3 | 2 | 4 | 2 |
| B18 | 1,000 | 4 | 5 | 5 | 3 | 4 | 2 |
| B20 | 1,000 | 4 | 4 | 4 | 2 | 4 | 2 |
| B21 | 1,000 | 2 | 4 | 3 | 3 | 4 | 0 |
| B22 | 1,000 | 0 | — | 0 | 0 | 0 | 0 |
| B23 | 1,000 | 5 | 5 | 5 | 4 | 4 | 4 |
| B24 | 1,000 | 3 | 3 | 3 | 3 | 3 | 0 |
| B25 | 1,000 | 0 | 2 | 0 | 0 | 0 | 0 |
| B27 | 1,000 | 3 | 5 | 3 | 1 | 4 | 2 |
| B28 | 1,000 | 0 | 0 | 0 | 0 | 0 | 0 |
| B29 | 1,000 | 0 | 2 | 0 | 0 | 0 | 0 |
| B30 | 1,000 | 0 | 2 | 0 | 0 | 0 | 0 |
| B31 | 1,000 | 5 | 5 | 5 | 4 | 5 | 4 |
| B32 | 1,000 | 5 | 5 | 5 | 4 | 5 | 4 |
| B33 | 1,000 | 5 | 5 | 5 | 4 | 5 | 4 |
| B34 | 1,000 | 4 | 2 | 1 | 2 | 3 | 1 |
| B35 | 1,000 | 3 | 5 | 3 | 1 | 4 | 0 |
| B36 | 1,000 | 5 | 5 | 5 | 3 | 5 | 2 |
| B37 | 1,000 | 4 | 5 | 4 | 3 | 3 | 3 |
| B38 | 1,000 | 5 | 5 | 5 | 4 | 5 | 4 |
| B39 | 1,000 | 5 | 5 | 5 | 4 | 5 | 4 |
| B40 | 1,000 | 5 | 3 | 3 | 1 | 2 | 0 |
| B41 | 1,000 | 4 | 2 | 4 | 3 | 4 | 2 |
| B42 | 1,000 | 5 | 5 | 5 | 4 | 5 | 2 |
| B43 | 1,000 | 5 | 5 | 4 | 2 | 4 | 1 |
| B45 | 1000 | 5 | 5 | 5 | 4 | 5 | 3 |
| B46 | 1000 | 5 | 5 | 4 | 3 | 4 | 1 |
| B48 | 1000 | 4 | 5 | 3 | 4 | 4 | 1 |
| B49 | 1000 | 0 | 0 | 0 | 0 | 0 | 0 |
| C1 | 1000 | 5 | 5 | 4 | 4 | 5 | 4 |
| C2 | 1000 | 4 | 5 | 5 | 4 | 4 | 2 |
| C3 | 1000 | 5 | 5 | 4 | 4 | 5 | 2 |
| C4 | 1000 | 4 | 4 | 4 | 3 | 4 | 3 |
| C5 | 1000 | 2 | 3 | 4 | 3 | 4 | 2 |
| C6 | 1000 | 5 | 5 | 4 | 4 | 5 | 4 |
| C7 | 1000 | 4 | 4 | 4 | 3 | 4 | 3 |
| C8 | 1000 | 4 | 5 | 5 | 4 | 4 | 2 |
| C9 | 1000 | 2 | 3 | 4 | 3 | 4 | 2 |
| C10 | 1000 | 4 | 5 | 5 | 4 | 4 | 2 |
| C11 | 1000 | 5 | 2 | 1 | 0 | 1 | 1 |
| C12 | 1000 | 5 | 5 | 3 | 3 | 4 | 2 |
| C13 | 1000 | 3 | 2 | 2 | 2 | 2 | 0 |
| D1 | 1000 | 5 | 5 | 4 | 4 | 4 | 2 |
| D2 | 1000 | 5 | 5 | 4 | 4 | 4 | 2 |
| D3 | 1000 | 5 | 5 | 5 | 3 | 5 | 4 |
| D4 | 1000 | 5 | 2 | 2 | 3 | 4 | 2 |
| D5 | 1000 | 0 | 0 | 0 | 0 | 0 | 0 |
| E1 | 1000 | 5 | 5 | 4 | 4 | 5 | 2 |
| E2 | 1000 | 5 | 5 | 5 | 3 | 5 | 3 |
| E3 | 1000 | 4 | 5 | 2 | 2 | 4 | 1 |
| E4 | 1000 | 5 | 5 | 5 | 3 | 4 | 2 |
| E5 | 1000 | 5 | 5 | 5 | 3 | 5 | 2 |

TABLE 2-continued

Application pre-emergence

| Compound Number | Rate (g/ha) | ABUTH | AMARE | SETFA | ALOMY | ECHCG | ZEAMX |
|---|---|---|---|---|---|---|---|
| F1 | 1000 | 5 | 5 | 4 | 3 | 5 | 2 |
| F2 | 1000 | 5 | 5 | 4 | 3 | 5 | 3 |
| F3 | 1000 | 5 | 5 | 4 | 3 | 5 | 3 |
| F4 | 1000 | 5 | 5 | 4 | 3 | 5 | 2 |
| G1 | 1000 | 5 | 5 | 4 | 4 | 5 | 3 |
| G2 | 1000 | 5 | 5 | 5 | 4 | 5 | 4 |
| G3 | 1000 | 4 | 5 | 5 | 4 | 4 | 2 |
| G4 | 1000 | 5 | 5 | 5 | 4 | 5 | 3 |
| G5 | 1000 | 5 | 5 | 4 | 3 | 5 | 1 |
| G6 | 1000 | 5 | 5 | 4 | 4 | 5 | 3 |
| G7 | 1000 | 5 | 5 | 4 | 3 | 5 | 1 |
| G8 | 1000 | 5 | 5 | 5 | 4 | 5 | 4 |
| G9 | 1000 | 5 | 5 | 5 | 4 | 5 | 3 |
| G10 | 1000 | 5 | 5 | 4 | 3 | 5 | 4 |
| G11 | 1000 | 5 | 5 | 5 | 4 | 5 | 4 |
| G12 | 1000 | 4 | 4 | 3 | 3 | 4 | 3 |
| H1 | 1000 | 5 | 5 | 5 | 4 | 5 | 4 |
| H2 | 1000 | 5 | 5 | 5 | 4 | 5 | 4 |
| H3 | 1000 | 4 | 4 | 4 | 4 | 5 | 1 |
| H4 | 1000 | 5 | 5 | 5 | 4 | 5 | 4 |
| I1 | 1000 | 5 | 5 | 4 | 4 | 5 | 3 |
| J1 | 1000 | 5 | 5 | 4 | 3 | 5 | 2 |
| J2 | 1000 | 5 | 5 | 4 | 3 | 5 | 2 |
| J3 | 1000 | 0 | 0 | 0 | 0 | 0 | 0 |
| J4 | 1000 | 5 | 5 | 5 | 4 | 4 | 4 |
| L1 | 1000 | 5 | 5 | 5 | 4 | 5 | 3 |
| L2 | 1000 | 4 | 3 | 3 | 3 | 4 | 0 |
| L3 | 1000 | 4 | 3 | 3 | 3 | 4 | 2 |
| L4 | 1000 | 4 | 3 | 4 | 4 | 5 | 2 |
| M1 | 1000 | 5 | 5 | 5 | 4 | 5 | 4 |
| M2 | 1000 | 5 | 5 | 4 | 4 | 5 | 3 |
| M3 | 1000 | 4 | 5 | 2 | 3 | 3 | 0 |
| M4 | 1000 | 5 | 5 | 2 | 2 | 2 | 1 |
| M5 | 1000 | 2 | 2 | 1 | 1 | 2 | 1 |
| N1 | 1000 | 5 | 5 | 5 | 4 | 4 | 4 |
| O1 | 1000 | 0 | 0 | 0 | 0 | 0 | 0 |
| R1 | 1000 | 5 | 5 | 5 | 4 | 5 | 4 |
| R2 | 1000 | 5 | 5 | 5 | 4 | 5 | 4 |
| T1 | 1000 | 5 | 5 | 4 | 4 | 5 | 2 |
| T2 | 1000 | 5 | 4 | 5 | 4 | 5 | 4 |
| W1 | 1000 | 5 | 5 | 5 | 4 | 4 | 3 |
| W2 | 1000 | 5 | 5 | 5 | 4 | 4 | 4 |

Example 8b

Post-emergence Herbicidal Activity

Seeds of a variety of test species were sown in standard soil in pots. After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Table 3.

TABLE 3

Application post-emergence

| Compound Number | Rate (g/ha) | ABUTH | AMARE | SETFA | ALOMY | ECHCG | ZEAMX |
|---|---|---|---|---|---|---|---|
| A1 | 1000 | 5 | 5 | 5 | 5 | 5 | 5 |
| A2 | 1000 | 5 | 3 | 5 | 4 | 4 | 1 |
| A3 | 1000 | 5 | 5 | 5 | 5 | 5 | 5 |
| A4 | 1000 | 5 | 5 | 5 | 5 | 5 | 5 |
| A5 | 1000 | 5 | 3 | 5 | 4 | 5 | 3 |
| A6 | 1000 | 5 | 5 | 4 | 5 | 5 | 4 |
| A7 | 1000 | 5 | 5 | 5 | 5 | 5 | 5 |
| B1 | 1000 | 5 | 5 | 5 | 4 | 5 | 5 |
| B2 | 1000 | 5 | 5 | 5 | 5 | 5 | 5 |
| B3 | 1000 | 5 | 5 | 5 | 5 | 5 | 4 |
| B4 | 1000 | 5 | 5 | 5 | 5 | 5 | 3 |

TABLE 3-continued

Application post-emergence

| Compound Number | Rate (g/ha) | ABUTH | AMARE | SETFA | ALOMY | ECHCG | ZEAMX |
|---|---|---|---|---|---|---|---|
| B5 | 1000 | 5 | 5 | 4 | 4 | 5 | 5 |
| B6 | 1000 | 5 | 5 | 5 | 5 | 5 | 4 |
| B7 | 1000 | 5 | 5 | 5 | 4 | 5 | 2 |
| B8 | 1000 | 5 | 5 | 5 | 5 | 5 | 4 |
| B9 | 1000 | 5 | 5 | 5 | 5 | 5 | 5 |
| B10 | 1000 | 3 | 0 | 5 | 0 | 2 | 2 |
| B11 | 1000 | 5 | 5 | 5 | 3 | 5 | 1 |
| B12 | 1000 | 1 | 2 | 1 | 1 | 1 | 1 |
| B13 | 1000 | 5 | 5 | 5 | 5 | 5 | 3 |
| B14 | 1000 | 5 | 5 | 4 | 4 | 5 | 5 |
| B15 | 1000 | 4 | 4 | 2 | 3 | 4 | 1 |
| B16 | 1000 | 5 | 5 | 5 | 5 | 5 | 4 |
| B17 | 1000 | 5 | 5 | 5 | 3 | 5 | 1 |
| B18 | 1000 | 5 | 5 | 5 | 5 | 5 | 5 |
| B20 | 1000 | 5 | 5 | 5 | 4 | 5 | 2 |
| B21 | 1000 | 4 | 4 | 5 | 2 | 4 | 0 |
| B22 | 1000 | 3 | 0 | 5 | 0 | 2 | 2 |
| B23 | 1000 | 5 | 5 | 5 | 5 | 5 | 4 |
| B24 | 1000 | 5 | 5 | 5 | 4 | 5 | 1 |
| B25 | 1000 | 3 | 3 | 1 | 1 | 1 | 0 |
| B27 | 1000 | 3 | 2 | 5 | 1 | 5 | 0 |
| B28 | 1000 | 0 | 0 | 0 | 0 | 0 | 0 |
| B29 | 1000 | 0 | 0 | 2 | 0 | 2 | 0 |
| B30 | 1000 | 3 | 3 | 2 | 0 | 0 | 0 |
| B31 | 1000 | 5 | 5 | 5 | 5 | 5 | 4 |
| B32 | 1000 | 5 | 5 | 5 | 5 | 5 | 4 |
| B33 | 1000 | 5 | 5 | 5 | 5 | 5 | 5 |
| B34 | 1000 | 5 | 2 | 3 | 3 | 3 | 0 |
| B35 | 1000 | 4 | 1 | 4 | 1 | 4 | 0 |
| B36 | 1000 | 5 | 5 | 5 | 4 | 5 | 5 |
| B37 | 1000 | 4 | 5 | 5 | 5 | 5 | 4 |
| B38 | 1000 | 5 | 5 | 5 | 5 | 5 | 5 |
| B39 | 1000 | 5 | 5 | 5 | 5 | 5 | 5 |
| B40 | 1000 | 5 | 5 | 5 | 4 | 5 | 1 |
| B41 | 1000 | 5 | 4 | 5 | 5 | 5 | 2 |
| B42 | 1000 | 5 | 5 | 5 | 5 | 5 | 5 |
| B43 | 1000 | 5 | 4 | 5 | 4 | 5 | 2 |
| B45 | 1000 | 5 | 5 | 5 | 5 | 5 | 4 |
| B46 | 1000 | 5 | 5 | 5 | 4 | 5 | 4 |
| B48 | 1000 | 5 | 5 | 4 | 4 | 5 | 1 |
| B49 | 1000 | 2 | 4 | 3 | 0 | 0 | 1 |
| C1 | 1000 | 5 | 5 | 4 | 5 | 5 | 3 |
| C2 | 1000 | 5 | 4 | 5 | 5 | 5 | 3 |
| C3 | 1000 | 5 | 5 | 5 | 4 | 5 | 4 |
| C4 | 1000 | 4 | 4 | 4 | 4 | 5 | 2 |
| C5 | 1000 | 4 | 5 | 5 | 5 | 5 | 3 |
| C6 | 1000 | 5 | 5 | 4 | 5 | 5 | 3 |
| C7 | 1000 | 4 | 4 | 4 | 4 | 5 | 2 |
| C8 | 1000 | 5 | 4 | 5 | 5 | 5 | 3 |
| C9 | 1000 | 4 | 5 | 5 | 5 | 5 | 3 |
| C10 | 1000 | 5 | 5 | 5 | 4 | 5 | 4 |
| C11 | 1000 | 5 | 1 | 3 | 2 | 4 | 2 |
| C12 | 1000 | 5 | 5 | 5 | 4 | 5 | 3 |
| C13 | 1000 | 1 | 1 | 2 | 1 | 1 | 1 |
| D1 | 1000 | 5 | 5 | 5 | 4 | 5 | 3 |
| D2 | 1000 | 5 | 5 | 5 | 4 | 5 | 3 |
| D3 | 1000 | 5 | 4 | 5 | 4 | 5 | 4 |
| D4 | 1000 | 5 | 4 | 4 | 4 | 5 | 0 |
| D5 | 1000 | 0 | 0 | 0 | 0 | 0 | 0 |
| E1 | 1000 | 5 | 5 | 5 | 4 | 5 | 4 |
| E2 | 1000 | 5 | 5 | 5 | 5 | 5 | 5 |
| E3 | 1000 | 4 | 5 | 4 | 4 | 5 | 2 |
| E4 | 1000 | 5 | 5 | 5 | 4 | 5 | 4 |
| E5 | 1000 | 5 | 5 | 5 | 5 | 5 | 4 |
| F1 | 1000 | 5 | 5 | 5 | 5 | 5 | 5 |
| F2 | 1000 | 5 | 5 | 5 | 5 | 5 | 5 |
| F3 | 1000 | 5 | 5 | 5 | 5 | 5 | 5 |
| F4 | 1000 | 5 | 5 | 5 | 5 | 5 | 5 |
| G1 | 1000 | 5 | 5 | 5 | 5 | 5 | 5 |
| G2 | 1000 | 5 | 5 | 5 | 5 | 5 | 4 |
| G3 | 1000 | 5 | 5 | 5 | 4 | 5 | 4 |
| G4 | 1000 | 5 | 5 | 5 | 5 | 5 | 5 |
| G5 | 1000 | 5 | 5 | 5 | 4 | 5 | 5 |
| G6 | 1000 | 5 | 5 | 5 | 5 | 5 | 5 |
| G7 | 1000 | 5 | 5 | 5 | 4 | 5 | 5 |

TABLE 3-continued

Application post-emergence

| Compound Number | Rate (g/ha) | ABUTH | AMARE | SETFA | ALOMY | ECHCG | ZEAMX |
|---|---|---|---|---|---|---|---|
| G8 | 1000 | 5 | 5 | 5 | 5 | 5 | 4 |
| G9 | 1000 | 5 | 5 | 5 | 5 | 5 | 5 |
| G10 | 1000 | 5 | 5 | 5 | 5 | 5 | 4 |
| G11 | 1000 | 5 | 5 | 5 | 5 | 5 | 3 |
| G12 | 1000 | 4 | 4 | 3 | 3 | 4 | 1 |
| H1 | 1000 | 5 | 5 | 5 | 5 | 5 | 4 |
| H2 | 1000 | 5 | 5 | 5 | 5 | 5 | 4 |
| H3 | 1000 | 5 | 4 | 5 | 5 | 5 | 3 |
| H4 | 1000 | 5 | 5 | 5 | 5 | 5 | 5 |
| I1 | 1000 | 5 | 5 | 5 | 4 | 5 | 5 |
| J1 | 1000 | 5 | 5 | 5 | 5 | 5 | 4 |
| J2 | 1000 | 5 | 5 | 5 | 5 | 5 | 4 |
| J3 | 1000 | 4 | 2 | 4 | 1 | 2 | 0 |
| J4 | 1000 | 5 | 5 | 5 | 5 | 5 | 5 |
| L1 | 1000 | 5 | 5 | 5 | 5 | 5 | 3 |
| L2 | 1000 | 5 | 5 | 5 | 5 | 5 | 1 |
| L3 | 1000 | 5 | 4 | 5 | 4 | 5 | 2 |
| L4 | 1000 | 5 | 5 | 5 | 5 | 5 | 2 |
| M1 | 1000 | 5 | 5 | 5 | 5 | 5 | 4 |
| M2 | 1000 | 5 | 5 | 5 | 5 | 5 | 3 |
| M3 | 1000 | 5 | 5 | 5 | 5 | 5 | 1 |
| M4 | 1000 | 5 | 5 | 4 | 4 | 5 | 0 |
| M5 | 1000 | 4 | 2 | 1 | 2 | 2 | 0 |
| N1 | 1000 | 5 | 5 | 5 | 5 | 5 | 4 |
| O1 | 1000 | 0 | 0 | 0 | 0 | 0 | 0 |
| R1 | 1000 | 5 | 5 | 5 | 5 | 5 | 5 |
| R2 | 1000 | 5 | 5 | 5 | 5 | 5 | 4 |
| T1 | 1000 | 5 | 5 | 5 | 5 | 5 | 3 |
| T2 | 1000 | 5 | 5 | 5 | 5 | 5 | 5 |
| W1 | 1000 | 5 | 5 | 5 | 5 | 5 | 5 |
| W2 | 1000 | 5 | 5 | 5 | 5 | 5 | 5 |

ABUTH = *Abutilon theophrasti*;;
AMARE = *Amaranthus retroflexus*;
SETFA = *Setaria faberi*;
ALOMY = *Alopecurus myosuroides*;
ECHCG = *Echinochloa crus-galli*;
ZEAMX = *Zea mays*.

The invention claimed is:
1. A herbicidal compound of formula (I)

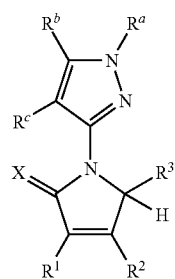

wherein
X is selected from S and O;
$R^a$ is selected from hydrogen, $C_1$-$C_6$ alkyl and $C_1$-$C_6$ haloalkyl;
$R^b$ is selected from hydrogen, formyl, hydroxyl, halogen, nitro, cyano, $C_1$-$C_6$ alkyl, $C_1$-$C_6$ cyanoalkyl, $C_3$-$C_6$ cycloalkyl, $C_3$-$C_6$ cyanocycloalkyl, $C_1$-$C_6$ haloalkyl, $C_1$-$C_6$ alkylthio, $C_1$-$C_6$ alkoxy, $C_1$-$C_6$ alkoxy $C_1$-$C_6$ alkyl, $C_1$-$C_6$ alkthio $C_1$-$C_6$ alkyl, $C_1$-$C_6$ cyanoalkoxy, $C_1$-$C_6$ haloalkoxy, $C_1$-$C_6$ alkoxy $C_1$-$C_6$ alkoxy, $C_2$-$C_6$ alkenyl, $C_2$-$C_6$ alkynyl, $C_2$-$C_6$ cyanoalkenyl, $C_2$-$C_6$ cyanoalkynyl, $C_2$-$C_6$ alkenyloxy, $C_2$-$C_6$ alkynyloxy, $C_2$-$C_6$ haloalkenyl, $C_2$-$C_6$ haloalkynyl, $C_2$-$C_6$ haloalkenyloxy, $C_2$-$C_6$ haloalkynyloxy, $C_1$-$C_6$ alkoxy $C_2$-$C_6$ alkenyl, $C_1$-$C_6$ alkoxy $C_2$-$C_6$ alkynyl, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylsulfonyloxy, $C_1$-$C_6$ alkylcarbonyl, $C_1$-$C_6$ haloalkylcarbonyl, $C_2$-$C_6$ alkenylcarbonyl, $C_2$-$C_6$ alkynylcarbonyl, $C_2$-$C_6$ haloalkenylcarbonyl, $C_2$-$C_6$ haloalkynylcarbonyl, tri $C_1$-$C_6$ alkylsilyl $C_2$-$C_6$ alkynyl, a group $R^5R^6N$—, a group $R^5C(O)N(R^6)$—, a group $R^5S(O_2)N(R^6)$—, a group $R^5R^6NSO_2$—, a $C_6$-$C_{10}$ aryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ aryloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ benzyl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ benzyloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_3$-$C_6$ heterocyclyl group optionally substituted by from 1 to 3 groups independently selected from $C_1$-$C_4$ alkyl, a $C_3$-$C_6$ cycloalkyl group optionally substituted with from 1 to 3 groups independently selected from halogen or $C_1$-$C_6$ alkyl and a $C_3$-$C_6$ cycloalkenyl group optionally substituted with from 1 to 3 groups independently selected from halogen or $C_1$-$C_6$ alkyl; and wherein when $R^b$ is $C_2$-$C_6$ alkynyl, $C_2$-$C_6$ cyanoalkynyl, $C_2$-$C_6$ haloalkynyl or $C_1$-$C_6$ alkoxy $C_2$-$C_6$ alkynyl, the alkynyl group is not directly attached to the pyrazole ring;

$R^c$ is selected from hydrogen, halogen, cyano, $C_1$-$C_6$ alkyl or $C_1$-$C_6$ haloalkyl;

or $R^a$ and $R^b$ together with the nitrogen and carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl;

or $R^b$ and $R^c$ together with the carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl;

$R^1$ is halogen or $C_1$-$C_3$ alkoxy;
$R^2$ is $C_1$-$C_6$ alkyl or $C_1$-$C_3$ alkoxy;
$R^3$ is selected from halogen, hydroxyl, or any one of the following groups

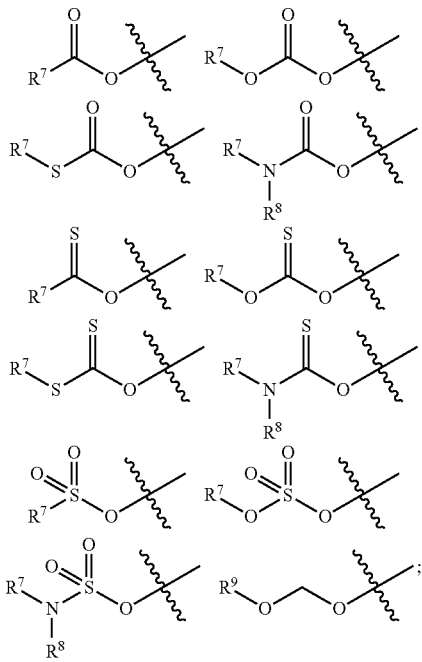

$R^5$ and $R^6$ are independently selected from hydrogen, $C_1$-$C_6$ alkyl, $C_1$-$C_6$ haloalkyl, $C_2$-$C_6$ alkenyl, $C_2$-$C_6$ alkynyl, or $R^5$ and $R^6$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen or $C_1$-$C_6$ alkyl;

$R^7$ and $R^8$ are independently selected from hydrogen, $C_1$-$C_6$ alkyl, $C_1$-$C_6$ haloalkyl, $C_2$-$C_6$ alkenyl, $C_2$-$C_6$ alkynyl, a $C_5$-$C_{10}$ heteroaryl group which can be monoor bicyclic comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy, a $C_6$-$C_{10}$ aryl group optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, or $R^7$ and $R^8$ together with the atoms to which they are attached form a 3-6 membered saturated or partially unsaturated ring optionally comprising from 1 to 3 heteroatoms independently selected from S, O and N and optionally substituted with from 1 to 3 groups independently selected from halogen or $C_1$-$C_6$ alkyl;

$R^9$ is selected from $C_1$-$C_6$ alkyl or benzyl optionally substituted with 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy;

or an N-oxide or salt form thereof.

2. The compound of claim 1, wherein X is O.

3. The compound of claim 1, wherein $R^a$ is selected from hydrogen, methyl, ethyl, iso-propyl or $C_1$-$C_3$ haloalkyl or $R^a$ and $R^b$ together with the nitrogen and carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl.

4. The compound of claim 1, wherein $R^b$ is selected from hydrogen, halogen, cyano, $C_1$-$C_6$ alkyl, $C_3$-$C_6$ cycloalkyl, $C_1$-$C_6$ haloalkyl, $C_2$-$C_6$ alkenyl, $C_1$-$C_6$ cyanoalkyl, $C_1$-$C_6$ alkylthio, $C_1$-$C_6$ alkylsulfinyl, $C_1$-$C_6$ alkylsulfonyl, $C_1$-$C_6$ alkoxy $C_1$-$C_6$ alkyl, $C_2$-$C_6$ alkynyl, $C_1$-$C_6$ alkoxy $C_2$-$C_6$ alkenyl, a $C_6$-$C_{10}$ benzyl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ aryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_3$-$C_6$ heteroaryl group optionally substituted by from 1 to 3 groups independently selected from $C_1$-$C_4$ alkyl, a $C_3$-$C_6$ cycloalkenyl group optionally substituted with from 1 to 3 groups independently selected from halogen or $C_1$-$C_6$ alkyl, or $R^a$ and $R^b$ together with the nitrogen and carbon atoms to which they are attached form a 3-7 membered saturated or partially unsaturated ring optionally comprising 1 to 3 heteroatoms independently selected from S, O and N and optionally substituted with 1 to 3 groups independently selected from $C_1$-$C_6$ alkyl or $R^b$ and $R^c$ together with the carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl.

5. The compound of claim 1, wherein $R^c$ is selected from hydrogen, methyl, chloro, bromo or cyano or $R^b$ and $R^c$ together with the carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl.

6. The compound of claim 1, wherein $R^1$ is bromo, chloro, methoxy or ethoxy.

7. The compound of claim 1, wherein $R^2$ is methyl, ethyl, methoxy or ethoxy.

8. The compound of claim 1, wherein $R^3$ is selected from halogen, hydroxyl, $C_1$-$C_6$ alkoxycarbonyloxy or aryloxycarbonyloxy wherein the aryl group may be substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy.

9. A herbicidal composition comprising a compound of formula I as defined in claim 1 together with at least one agriculturally acceptable adjuvant or diluent.

10. A composition according to claim 9 which comprises a further herbicide in addition to the compound of formula I.

11. A composition according to claim 9 which comprises a safener.

12. A method of controlling weeds in crops of useful plants, comprising applying to said weeds or to the locus of said weeds, or to said useful plants or to the locus of said useful plants, a compound of formula I as defined in claim 1.

* * * * *